US009492400B2

(12) United States Patent
Jon et al.

(10) Patent No.: US 9,492,400 B2
(45) Date of Patent: *Nov. 15, 2016

(54) COATED CONTROLLED RELEASE POLYMER PARTICLES AS EFFICIENT ORAL DELIVERY VEHICLES FOR BIOPHARMACEUTICALS

(75) Inventors: Sangyong Jon, Gwangju (KR); Omid C. Farokhazd, Chestnut Hill, MA (US); Robert S. Langer, Newton, MA (US); Jianjun Cheng, Champaign, IL (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 620 days.

This patent is subject to a terminal disclaimer.

(21) Appl. No.: 11/666,908

(22) PCT Filed: Nov. 4, 2005

(86) PCT No.: PCT/US2005/040100
§ 371 (c)(1),
(2), (4) Date: Feb. 26, 2008

(87) PCT Pub. No.: WO2007/001448
PCT Pub. Date: Jan. 4, 2007

(65) Prior Publication Data
US 2008/0268063 A1    Oct. 30, 2008

Related U.S. Application Data

(60) Provisional application No. 60/625,001, filed on Nov. 4, 2004.

(51) Int. Cl.
A61K 9/16   (2006.01)
A61K 9/50   (2006.01)
A61K 9/51   (2006.01)
A61K 9/00   (2006.01)

(52) U.S. Cl.
CPC ........... *A61K 9/5153* (2013.01); *A61K 9/5192* (2013.01); *A61K 9/0043* (2013.01); *A61K 9/0065* (2013.01); *A61K 9/5036* (2013.01)

(58) Field of Classification Search
CPC ............. A61K 9/5153; A61K 9/0043; A61K 9/0065; A61K 9/5036; A61K 9/5192
See application file for complete search history.

(56) References Cited

U.S. PATENT DOCUMENTS

| | | | |
|---|---|---|---|
| 3,766,774 A | 10/1973 | Clark | |
| 4,270,537 A | 6/1981 | Romaine | |
| 4,446,122 A | 5/1984 | Chu et al. | |
| 4,596,556 A | 6/1986 | Morrow et al. | |
| 4,631,211 A | 12/1986 | Houghten | |
| 4,638,045 A | 1/1987 | Kohn et al. | |
| 4,790,824 A | 12/1988 | Morrow et al. | |
| 4,795,436 A | 1/1989 | Robinson | |
| 4,806,621 A | 2/1989 | Kohn et al. | |
| 4,818,542 A | 4/1989 | DeLuca | |
| 4,839,416 A | 6/1989 | Orenstein | |
| 4,862,851 A | 9/1989 | Washino et al. | |
| 4,886,499 A | 12/1989 | Cirelli et al. | |
| 4,902,615 A | 2/1990 | Freeman et al. | |
| 4,904,479 A | 2/1990 | Illum | |
| 4,940,460 A | 7/1990 | Casey et al. | |
| 4,941,880 A | 7/1990 | Burns | |
| 4,946,929 A | 8/1990 | D'Amore et al. | |
| 4,959,219 A | 9/1990 | Chow | |
| RE33,405 E | 10/1990 | Chu et al. | |
| 4,970,299 A | 11/1990 | Bazinet et al. | |
| 4,976,968 A | 12/1990 | Steiner | |
| 5,010,167 A | 4/1991 | Ron et al. | |
| 5,015,235 A | 5/1991 | Crossman | |
| 5,019,379 A | 5/1991 | Domb et al. | |
| 5,055,404 A | 10/1991 | Ueda et al. | |

(Continued)

FOREIGN PATENT DOCUMENTS

| | | |
|---|---|---|
| CA | 2453959 | 1/2003 |
| CA | 2649149 | 10/2007 |

(Continued)

OTHER PUBLICATIONS

Chandy, T., G.S. Das, and G.H.R. Rao. 2000. 5-Fluorouracil-loaded chitosan coated polylactic acid microspheres as biodegradable drug carriers for cerebral tumours. J. Microencapsulation. 17(5): 625-638.*

(Continued)

*Primary Examiner* — Johann R Richter
*Assistant Examiner* — David Browe
(74) *Attorney, Agent, or Firm* — Pabst Patent Group LLP

(57) ABSTRACT

A composition for delivering an active agent to a patient. The composition includes a polymer core encapsulating the active agent and a mucoadhesive coating disposed about the core. The polymer may include covalently linked poly (ethylene glycol) chains, and the mucoadhesive coating may be selected to facilitate transfer of the particle through the intestinal mucosa. A molecular weight and cross-link density of the polymer may be selected such that the polymer core will decompose in a predetermined time interval. The fraction of the dose of the drug entering the system at circulation during the predetermined time interval may be between about 0.25% and about 25%. The composition may be formulated as a plurality of nanoparticles or microparticles that are combined with a pharmaceutically acceptable carrier to produce an edible or inhalable drug product.

52 Claims, 3 Drawing Sheets

(56) References Cited

U.S. PATENT DOCUMENTS

| | | |
|---|---|---|
| 5,064,413 A | 11/1991 | McKinnon et al. |
| 5,069,936 A | 12/1991 | Yen |
| 5,093,246 A | 3/1992 | Cech et al. |
| 5,118,528 A | 6/1992 | Fessi et al. |
| 5,141,496 A | 8/1992 | Dalto et al. |
| 5,162,504 A | 11/1992 | Horoszewicz |
| 5,174,930 A | 12/1992 | Stainmesse |
| 5,175,296 A | 12/1992 | Gerster |
| 5,190,521 A | 3/1993 | Hubbard et al. |
| 5,200,181 A | 4/1993 | Soltys |
| 5,240,963 A | 8/1993 | Domb |
| 5,270,163 A | 12/1993 | Gold et al. |
| 5,312,335 A | 5/1994 | McKinnon et al. |
| 5,328,483 A | 7/1994 | Jacoby |
| 5,334,144 A | 8/1994 | Alchas et al. |
| 5,334,497 A | 8/1994 | Inaba et al. |
| 5,339,163 A | 8/1994 | Homma et al. |
| 5,342,781 A | 8/1994 | Su |
| 5,383,851 A | 1/1995 | McKinnon, Jr. et al. |
| 5,389,640 A | 2/1995 | Gerster |
| 5,399,665 A | 3/1995 | Barrera et al. |
| 5,403,750 A | 4/1995 | Braatz |
| 5,417,662 A | 5/1995 | Hjertman et al. |
| 5,449,513 A | 9/1995 | Yokoyama |
| 5,466,220 A | 11/1995 | Brenneman |
| 5,472,704 A * | 12/1995 | Santus et al. .......... 424/435 |
| 5,480,381 A | 1/1996 | Weston |
| 5,500,161 A | 3/1996 | Andrianov et al. |
| 5,503,627 A | 4/1996 | McKinnon et al. |
| 5,512,600 A | 4/1996 | Mikos et al. |
| 5,514,378 A | 5/1996 | Mikos et al. |
| 5,520,639 A | 5/1996 | Peterson et al. |
| 5,527,288 A | 6/1996 | Gross et al. |
| 5,543,158 A | 8/1996 | Gref et al. |
| 5,567,588 A | 10/1996 | Gold et al. |
| 5,569,189 A | 10/1996 | Parsons |
| 5,578,325 A * | 11/1996 | Domb et al. .......... 424/501 |
| 5,595,877 A | 1/1997 | Gold et al. |
| 5,599,302 A | 2/1997 | Lilley et al. |
| 5,622,699 A | 4/1997 | Ruoslahti |
| 5,649,912 A | 7/1997 | Peterson |
| 5,660,985 A | 8/1997 | Pieken et al. |
| 5,686,113 A | 11/1997 | Speaker |
| 5,696,175 A | 12/1997 | Mikos et al. |
| 5,696,249 A | 12/1997 | Gold et al. |
| 5,704,911 A | 1/1998 | Parsons |
| 5,716,404 A | 2/1998 | Vacanti et al. |
| 5,733,925 A | 3/1998 | Kunz et al. |
| 5,736,372 A | 4/1998 | Vacanti et al. |
| 5,744,155 A | 4/1998 | Friedman |
| 5,763,177 A | 6/1998 | Gold et al. |
| 5,766,635 A | 6/1998 | Spenleuhauer |
| 5,770,417 A | 6/1998 | Vacanti et al. |
| 5,786,204 A | 7/1998 | He et al. |
| 5,789,163 A | 8/1998 | Drolet et al. |
| 5,804,178 A | 9/1998 | Vacanti et al. |
| 5,817,785 A | 10/1998 | Gold et al. |
| 5,820,879 A | 10/1998 | Fernandez et al. |
| 5,837,752 A | 11/1998 | Shastri et al. |
| 5,843,653 A | 12/1998 | Gold et al. |
| 5,843,732 A | 12/1998 | Davis et al. |
| 5,853,984 A | 12/1998 | Davis et al. |
| 5,869,103 A * | 2/1999 | Yeh et al. .......... 424/501 |
| 5,871,747 A | 2/1999 | GengouxSedlik |
| 5,874,218 A | 2/1999 | Drolet et al. |
| 5,876,727 A | 3/1999 | Swain |
| 5,879,712 A | 3/1999 | Bomberger |
| 5,893,397 A | 4/1999 | Peterson et al. |
| 5,898,031 A | 4/1999 | Crooke |
| 5,902,599 A | 5/1999 | Anseth et al. |
| 5,916,539 A | 6/1999 | Pilgrimm |
| 5,928,647 A | 7/1999 | Rock |
| 5,942,252 A | 8/1999 | Tice |
| 5,958,691 A | 9/1999 | Pieken et al. |
| 5,977,089 A | 11/1999 | Arimilli et al. |
| 5,993,412 A | 11/1999 | Deily et al. |
| 6,001,577 A | 12/1999 | Gold et al. |
| 6,005,087 A | 12/1999 | Cook et al. |
| 6,007,845 A | 12/1999 | Domb et al. |
| 6,030,613 A | 2/2000 | Blumberg |
| 6,031,086 A | 2/2000 | Switzer |
| 6,039,969 A | 3/2000 | Tomai |
| 6,043,224 A | 3/2000 | Lee |
| 6,060,306 A | 5/2000 | Flatt |
| 6,083,505 A | 7/2000 | Miller |
| 6,095,148 A | 8/2000 | Shastri et al. |
| 6,107,094 A | 8/2000 | Crooke |
| 6,110,462 A | 8/2000 | Barbas et al. |
| 6,120,666 A | 9/2000 | Jacobson |
| 6,123,727 A | 9/2000 | Vacanti et al. |
| 6,127,533 A | 10/2000 | Cook et al. |
| 6,139,870 A | 10/2000 | Verrecchia |
| 6,184,364 B1 | 2/2001 | Pieken et al. |
| 6,190,913 B1 | 2/2001 | Singh |
| 6,197,346 B1 | 3/2001 | Mathiowitz |
| 6,225,460 B1 | 5/2001 | Bischofberger et al. |
| 6,235,313 B1 | 5/2001 | Mathiowitz |
| 6,238,705 B1 | 5/2001 | Liu et al. |
| 6,242,246 B1 | 6/2001 | Gold et al. |
| 6,245,776 B1 | 6/2001 | Skwierczynski |
| 6,254,890 B1 | 7/2001 | Hirosue et al. |
| 6,265,608 B1 | 7/2001 | Sumner, Jr. |
| 6,288,040 B1 | 9/2001 | Muller |
| 6,291,673 B1 | 9/2001 | Fuchs |
| 6,344,318 B1 | 2/2002 | Gold et al. |
| 6,348,462 B1 | 2/2002 | Gerster |
| 6,365,187 B2 | 4/2002 | Mathiowitz et al. |
| 6,376,190 B1 | 4/2002 | Gold et al. |
| 6,395,718 B1 | 5/2002 | Slusher |
| 6,399,754 B1 | 6/2002 | Cook |
| 6,403,779 B1 | 6/2002 | Kawasaki et al. |
| 6,429,200 B1 | 8/2002 | Monahan et al. |
| 6,444,782 B1 | 9/2002 | Hamlin |
| 6,451,527 B1 | 9/2002 | Larocca et al. |
| 6,458,539 B1 | 10/2002 | Gold et al. |
| 6,458,543 B1 | 10/2002 | Gold et al. |
| 6,482,594 B2 | 11/2002 | Gold et al. |
| 6,492,554 B2 | 12/2002 | Dalton et al. |
| 6,506,559 B1 | 1/2003 | Fire et al. |
| 6,506,577 B1 | 1/2003 | Deming et al. |
| 6,528,499 B1 | 3/2003 | Kozikowski |
| 6,558,951 B1 | 5/2003 | Tomai |
| 6,569,896 B2 | 5/2003 | Dalton et al. |
| 6,589,562 B1 | 7/2003 | Shefer et al. |
| 6,589,563 B2 | 7/2003 | Prokop |
| 6,608,201 B2 | 8/2003 | Gerster |
| 6,610,319 B2 | 8/2003 | Tomai |
| 6,610,713 B2 | 8/2003 | Tracey |
| 6,632,922 B1 | 10/2003 | Deming et al. |
| 6,656,469 B1 | 12/2003 | Svensson |
| 6,686,446 B2 | 2/2004 | Deming et al. |
| 6,686,472 B2 | 2/2004 | Gerster |
| 6,696,076 B2 | 2/2004 | Tomai |
| 6,699,474 B1 | 3/2004 | Cerny |
| 6,716,583 B2 | 4/2004 | Gold et al. |
| 6,723,429 B2 | 4/2004 | Bengs |
| 6,737,056 B1 | 5/2004 | Presta |
| 6,747,156 B2 | 6/2004 | Johansson |
| 6,767,702 B2 | 7/2004 | Mirkin |
| 6,818,732 B2 | 11/2004 | Deming et al. |
| 6,838,484 B2 | 1/2005 | Steiner et al. |
| 6,875,605 B1 | 4/2005 | Ma |
| 6,875,886 B2 | 4/2005 | Frangioni |
| 6,902,743 B1 | 6/2005 | Setterstrom |
| 6,932,971 B2 | 8/2005 | Bachmann |
| 6,984,393 B2 | 1/2006 | Amsden |
| 6,995,284 B2 | 2/2006 | Dalton et al. |
| 6,998,500 B2 | 2/2006 | Dalton et al. |
| 7,008,411 B1 | 3/2006 | Mandrusov et al. |
| 7,022,870 B2 | 4/2006 | Dalton et al. |
| 7,026,500 B2 | 4/2006 | Dalton et al. |
| 7,029,859 B2 | 4/2006 | Thompson |
| 7,030,228 B1 | 4/2006 | Schmitz |
| 7,056,704 B2 | 6/2006 | Tuschl et al. |

(56) References Cited

U.S. PATENT DOCUMENTS

| | | |
|---|---|---|
| 7,078,196 B2 | 7/2006 | Tuschl et al. |
| 7,097,837 B2 | 8/2006 | Nielsen |
| 7,149,574 B2 | 12/2006 | Yun |
| 7,163,680 B2 | 1/2007 | Bander |
| 7,247,502 B2 | 7/2007 | Ennifar |
| 7,250,499 B2 | 7/2007 | Mirkin |
| 7,335,744 B2 | 2/2008 | Liu |
| 7,363,076 B2 | 4/2008 | Yun |
| 7,375,180 B2 | 5/2008 | Gorden |
| 7,387,271 B2 | 6/2008 | Noelle |
| 7,422,902 B1 | 9/2008 | Wheeler |
| 7,427,629 B2 | 9/2008 | Kedl |
| 7,488,792 B2 | 2/2009 | Ruoslahti |
| 7,550,441 B2 | 6/2009 | Farkhzad et al. |
| 7,727,969 B2 | 6/2010 | Farokhzad |
| 7,762,803 B2 | 7/2010 | Nakazato |
| 7,767,803 B2 | 8/2010 | Diener |
| 8,277,812 B2 | 10/2012 | Iannacone |
| 8,343,497 B2 | 1/2013 | Shi |
| 8,343,498 B2 | 1/2013 | Alexis |
| 8,562,998 B2 | 10/2013 | Shi |
| 8,574,564 B2 | 11/2013 | Renner |
| 8,637,028 B2 | 1/2014 | Alexis |
| 2001/0012890 A1 | 8/2001 | Thompson |
| 2002/0009466 A1 | 1/2002 | Brayden |
| 2002/0064780 A1 | 5/2002 | Gold et al. |
| 2002/0068091 A1 | 6/2002 | Davis et al. |
| 2002/0086356 A1 | 7/2002 | Tuschl et al. |
| 2002/0099036 A1 | 7/2002 | Dalton et al. |
| 2002/0099096 A1 | 7/2002 | Dalton et al. |
| 2002/0102613 A1 | 8/2002 | Hoogenboom |
| 2002/0106647 A1 | 8/2002 | Segal |
| 2002/0116054 A1 | 8/2002 | Lundell |
| 2002/0119473 A1 | 8/2002 | Lupold |
| 2002/0119916 A1 | 8/2002 | Hassan |
| 2002/0150578 A1 | 10/2002 | He et al. |
| 2002/0151004 A1 | 10/2002 | Craig |
| 2002/0153251 A1 | 10/2002 | Sassi et al. |
| 2002/0156125 A1 | 10/2002 | Broder et al. |
| 2002/0173495 A1 | 11/2002 | Dalton et al. |
| 2003/0003103 A1 | 1/2003 | Thompson |
| 2003/0003114 A1 | 1/2003 | Pan |
| 2003/0009029 A1 | 1/2003 | Buchholz et al. |
| 2003/0022868 A1 | 1/2003 | Dalton et al. |
| 2003/0035804 A1 | 2/2003 | D'Amico et al. |
| 2003/0054360 A1 | 3/2003 | Gold et al. |
| 2003/0087301 A1 | 5/2003 | Smith et al. |
| 2003/0099668 A1 | 5/2003 | Bachmann |
| 2003/0108611 A1 | 6/2003 | Bosch et al. |
| 2003/0108923 A1 | 6/2003 | Tuschl et al. |
| 2003/0133988 A1 | 7/2003 | Fearon |
| 2003/0134810 A1 | 7/2003 | Springate et al. |
| 2003/0138557 A1 | 7/2003 | Allison |
| 2003/0143184 A1 | 7/2003 | Seo |
| 2003/0162761 A1 | 8/2003 | Steiner et al. |
| 2003/0165478 A1 | 9/2003 | Sokoll |
| 2003/0175950 A1 | 9/2003 | McSwiggen |
| 2003/0219766 A1 | 11/2003 | Raitano et al. |
| 2003/0225040 A1 | 12/2003 | Dalton et al. |
| 2003/0228603 A1 | 12/2003 | Cload |
| 2003/0232013 A1 | 12/2003 | Sieckman et al. |
| 2003/0232792 A1 | 12/2003 | Dalton et al. |
| 2003/0235619 A1 | 12/2003 | Allen |
| 2004/0014789 A1 | 1/2004 | Lau |
| 2004/0014975 A1 | 1/2004 | Dalton et al. |
| 2004/0022727 A1 | 2/2004 | Stanton |
| 2004/0022840 A1 | 2/2004 | Nagy et al. |
| 2004/0029913 A1 | 2/2004 | Dalton et al. |
| 2004/0043923 A1 | 3/2004 | Parma et al. |
| 2004/0052727 A1 | 3/2004 | Dalton et al. |
| 2004/0054190 A1 | 3/2004 | Pomper |
| 2004/0059094 A1 | 3/2004 | Bachmann et al. |
| 2004/0067196 A1 | 4/2004 | Brunke et al. |
| 2004/0067503 A1 | 4/2004 | Tan et al. |
| 2004/0067979 A1 | 4/2004 | Dalton et al. |
| 2004/0072234 A1 | 4/2004 | Parma et al. |
| 2004/0086544 A1 | 5/2004 | Bezemer |
| 2004/0087810 A1 | 5/2004 | Dalton et al. |
| 2004/0092470 A1 | 5/2004 | Leonard et al. |
| 2004/0136961 A1 | 7/2004 | Prokop et al. |
| 2004/0141958 A1 | 7/2004 | Steinaa |
| 2004/0147489 A1 | 7/2004 | Dalton et al. |
| 2004/0147550 A1 | 7/2004 | Dalton et al. |
| 2004/0156846 A1 | 8/2004 | Daum et al. |
| 2004/0167103 A1 | 8/2004 | Dalton et al. |
| 2004/0192626 A1 | 9/2004 | McSwiggen et al. |
| 2004/0241790 A1 | 12/2004 | Eriksen et al. |
| 2004/0247680 A1 | 12/2004 | Farokhzad |
| 2004/0248088 A1 | 12/2004 | Raitano et al. |
| 2004/0260092 A1 | 12/2004 | Miller et al. |
| 2004/0260108 A1 | 12/2004 | Dalton et al. |
| 2004/0266688 A1 | 12/2004 | Nayak |
| 2005/0017667 A1 | 1/2005 | Yamamoto |
| 2005/0019870 A1 | 1/2005 | Afar et al. |
| 2005/0019872 A1 | 1/2005 | Afar et al. |
| 2005/0020525 A1 | 1/2005 | McSwiggen et al. |
| 2005/0032733 A1 | 2/2005 | McSwiggen et al. |
| 2005/0033074 A1 | 2/2005 | Dalton et al. |
| 2005/0037075 A1 | 2/2005 | Farokhzad et al. |
| 2005/0048063 A1 | 3/2005 | Ruoslahti et al. |
| 2005/0069910 A1 | 3/2005 | Turner et al. |
| 2005/0079152 A1 | 4/2005 | Bot |
| 2005/0079533 A1 | 4/2005 | Samuelson |
| 2005/0079553 A1 | 4/2005 | Ayyoub |
| 2005/0080128 A1 | 4/2005 | Tsukamoto et al. |
| 2005/0100877 A1 | 5/2005 | Xu et al. |
| 2005/0107322 A1 | 5/2005 | OHagan |
| 2005/0122550 A1 | 6/2005 | Plewa et al. |
| 2005/0136258 A1 | 6/2005 | Nie |
| 2005/0142582 A1 | 6/2005 | Doyle |
| 2005/0158390 A1 | 7/2005 | Rana et al. |
| 2005/0191294 A1 | 9/2005 | Arap et al. |
| 2005/0207940 A1 | 9/2005 | Butler |
| 2005/0214378 A1 | 9/2005 | Hoarau |
| 2005/0233948 A1 | 10/2005 | D'Amico et al. |
| 2005/0239134 A1 | 10/2005 | Gorenstein |
| 2005/0244863 A1 | 11/2005 | Mir |
| 2005/0249799 A1 | 11/2005 | Jacob et al. |
| 2005/0256071 A1 | 11/2005 | Davis |
| 2005/0260186 A1 | 11/2005 | Bookbinder et al. |
| 2006/0002852 A1 | 1/2006 | Saltzman et al. |
| 2006/0002971 A1 | 1/2006 | Saltzman |
| 2006/0004042 A1 | 1/2006 | Dalton et al. |
| 2006/0009529 A1 | 1/2006 | Dalton et al. |
| 2006/0035966 A1 | 2/2006 | Dalton et al. |
| 2006/0057219 A1 | 3/2006 | Nagasaki |
| 2006/0062787 A1 | 3/2006 | Hitraya |
| 2006/0083711 A1 | 4/2006 | Berry et al. |
| 2006/0110460 A1 | 5/2006 | Ferret |
| 2006/0111271 A1 | 5/2006 | Cerny |
| 2006/0165987 A1 | 7/2006 | Hildgen |
| 2006/0173170 A1 | 8/2006 | Chamberlian et al. |
| 2006/0183931 A1 | 8/2006 | Dalton et al. |
| 2006/0228371 A1 | 10/2006 | Raso |
| 2006/0239907 A1 | 10/2006 | Luzzi et al. |
| 2006/0240093 A1 | 10/2006 | Maclachlan et al. |
| 2006/0241180 A1 | 10/2006 | Dalton et al. |
| 2006/0258628 A1 | 11/2006 | Steiner et al. |
| 2006/0269557 A1 | 11/2006 | Sherman et al. |
| 2006/0276540 A1 | 12/2006 | Dalton et al. |
| 2006/0287547 A1 | 12/2006 | Dalton et al. |
| 2007/0014807 A1 | 1/2007 | Maida |
| 2007/0041901 A1 | 2/2007 | Diener |
| 2007/0043066 A1 | 2/2007 | Sum |
| 2007/0053845 A1 | 3/2007 | Sengupta |
| 2007/0116768 A1 | 5/2007 | Chorny |
| 2007/0184068 A1 | 8/2007 | Renner |
| 2007/0224225 A1 | 9/2007 | IracheGarreta |
| 2007/0225213 A1 | 9/2007 | Kosak |
| 2008/0019908 A1 | 1/2008 | Akitsu |
| 2008/0026000 A1 | 1/2008 | Ennifar |
| 2008/0031899 A1 | 2/2008 | Reddy |
| 2008/0057102 A1 | 3/2008 | Roorda |
| 2008/0081074 A1 | 4/2008 | Gu et al. |

(56) References Cited

U.S. PATENT DOCUMENTS

| | | |
|---|---|---|
| 2008/0124400 A1 | 5/2008 | Liggins |
| 2008/0171059 A1 | 7/2008 | Howland |
| 2008/0193381 A1 | 8/2008 | Babich |
| 2008/0213377 A1 | 9/2008 | Bhatia |
| 2008/0268063 A1 | 10/2008 | Jon |
| 2008/0299177 A1 | 12/2008 | Hardy |
| 2009/0004118 A1 | 1/2009 | Nie |
| 2009/0028910 A1 | 1/2009 | DeSimone et al. |
| 2009/0061010 A1 | 3/2009 | Zale |
| 2009/0074828 A1 | 3/2009 | Alexis |
| 2009/0117549 A1 | 5/2009 | Tan |
| 2009/0192100 A1 | 7/2009 | Vater |
| 2009/0298710 A1 | 12/2009 | Farokhzad et al. |
| 2010/0022680 A1 | 1/2010 | Kamik et al. |
| 2010/0068285 A1 | 3/2010 | Zale |
| 2010/0068286 A1 | 3/2010 | Troiano |
| 2010/0069426 A1 | 3/2010 | Zale |
| 2010/0092425 A1 | 4/2010 | Von Andrian et al. |
| 2010/0104655 A1 | 4/2010 | Zale |
| 2010/0129392 A1 | 5/2010 | Shi et al. |
| 2010/0129439 A1 | 5/2010 | Alexis et al. |
| 2010/0144845 A1 | 6/2010 | Farokhzad et al. |
| 2010/0183727 A1 | 7/2010 | Iannaconna et al. |
| 2010/0196482 A1 | 8/2010 | Radovic-Moreno et al. |
| 2010/0203142 A1 | 8/2010 | Zhang et al. |
| 2010/0216804 A1 | 8/2010 | Zale |
| 2010/0226986 A1 | 9/2010 | Grayson |
| 2010/0233251 A1 | 9/2010 | Von Andrian et al. |
| 2010/0266491 A1 | 10/2010 | Farokhzad |
| 2010/0297233 A1 | 11/2010 | Moretti |
| 2010/0303723 A1 | 12/2010 | Farokhzad |
| 2011/0052697 A1 | 3/2011 | Farokhzad |

FOREIGN PATENT DOCUMENTS

| | | |
|---|---|---|
| DK | 0418187 | 3/1991 |
| EP | 0333523 | 9/1989 |
| EP | 1279404 | 1/2003 |
| EP | 1752141 | 2/2007 |
| EP | 1872793 | 1/2008 |
| EP | 1932538 | 6/2008 |
| EP | 2106806 | 10/2009 |
| JP | 2006528954 | 5/2006 |
| KR | 0418916 | 3/2002 |
| KR | 0041712 | 6/2004 |
| WO | WO 88/04300 | 6/1988 |
| WO | WO 90/11364 | 3/1990 |
| WO | 9006430 | 6/1990 |
| WO | 9006433 | 6/1990 |
| WO | 9106286 | 5/1991 |
| WO | 9106287 | 5/1991 |
| WO | 9503357 | 2/1995 |
| WO | WO 97/04747 | 2/1997 |
| WO | WO 97/13537 | 4/1997 |
| WO | WO 97/37705 | 10/1997 |
| WO | WO 98/08856 | 3/1998 |
| WO | 98/51325 | 11/1998 |
| WO | WO-99/01498 A2 | 1/1999 |
| WO | WO 99/34850 | 7/1999 |
| WO | WO 00/21572 | 4/2000 |
| WO | WO 00/27363 | 5/2000 |
| WO | 0032239 | 6/2000 |
| WO | WO 00/44895 | 8/2000 |
| WO | 0059538 | 10/2000 |
| WO | WO 01/75164 | 10/2001 |
| WO | WO 02/18477 | 3/2002 |
| WO | WO 02/076469 | 10/2002 |
| WO | WO-02/076603 A1 | 10/2002 |
| WO | WO 02/100442 | 12/2002 |
| WO | WO 03/000777 | 1/2003 |
| WO | WO 03/004654 | 1/2003 |
| WO | 03033592 | 4/2003 |
| WO | WO-03/028657 A3 | 4/2003 |
| WO | WO-03/030941 A1 | 4/2003 |
| WO | WO-03/051304 A2 | 6/2003 |
| WO | 03074679 | 9/2003 |
| WO | WO 03/072637 | 9/2003 |
| WO | WO 03/102708 | 12/2003 |
| WO | 2004009116 | 1/2004 |
| WO | 2004030608 | 4/2004 |
| WO | WO 2004/030608 | 4/2004 |
| WO | WO 2004/071493 | 8/2004 |
| WO | 2004096140 | 11/2004 |
| WO | WO 2004/096998 | 11/2004 |
| WO | 2004105782 | 12/2004 |
| WO | WO 2005/012407 | 2/2005 |
| WO | WO 2005/028539 | 3/2005 |
| WO | 2005046572 | 5/2005 |
| WO | WO 2005/042573 | 5/2005 |
| WO | WO 2005/072710 | 8/2005 |
| WO | 2005105056 | 11/2005 |
| WO | WO 2005/111192 | 11/2005 |
| WO | 2005112885 | 12/2005 |
| WO | 2005112886 | 12/2005 |
| WO | WO 2005/121181 | 12/2005 |
| WO | 2006025627 | 3/2006 |
| WO | WO 2006/037979 | 4/2006 |
| WO | WO 2006/042146 | 4/2006 |
| WO | WO 2006/066158 | 6/2006 |
| WO | WO 2006/078278 | 7/2006 |
| WO | WO 2006/090924 | 8/2006 |
| WO | 2006093991 | 9/2006 |
| WO | 2006099445 | 9/2006 |
| WO | WO 2006/096754 | 9/2006 |
| WO | WO 2006/117217 | 11/2006 |
| WO | WO 2006/133271 | 12/2006 |
| WO | WO 2006/138463 | 12/2006 |
| WO | 2007001448 A2 | 1/2007 |
| WO | 2007052058 | 1/2007 |
| WO | WO 2007/021142 | 2/2007 |
| WO | 2007024026 | 3/2007 |
| WO | 2007034479 | 3/2007 |
| WO | 2007131972 | 5/2007 |
| WO | WO 2007/070682 | 6/2007 |
| WO | WO 2007/076371 | 7/2007 |
| WO | WO 2007/084797 | 7/2007 |
| WO | 2007098254 | 8/2007 |
| WO | WO 2007/109364 | 9/2007 |
| WO | WO 2007/118653 | 10/2007 |
| WO | 9503356 | 11/2007 |
| WO | 2008043157 | 11/2007 |
| WO | WO 2007/150030 | 12/2007 |
| WO | 9955715 | 4/2008 |
| WO | 2008041703 | 4/2008 |
| WO | 2008058192 | 5/2008 |
| WO | WO 2008/051291 | 5/2008 |
| WO | 2008105772 | 9/2008 |
| WO | 2008121949 | 10/2008 |
| WO | WO 2009/051837 | 4/2009 |
| WO | 2009109428 | 9/2009 |
| WO | WO 2009/109428 | 9/2009 |
| WO | 2010005721 | 1/2010 |
| WO | 2010005723 | 1/2010 |
| WO | 2010005725 | 1/2010 |
| WO | 2010005726 | 1/2010 |
| WO | 2010068866 | 6/2010 |
| WO | 2010075072 | 7/2010 |
| WO | 2010114768 | 10/2010 |
| WO | 2010114770 | 10/2010 |
| WO | 2011072218 | 6/2011 |

OTHER PUBLICATIONS

Ermak, T.H., and P.J. Giannasca. 1998. Microparticle targeting to M cells. Advanced Drug Delivery Reviews. 34: 261-283.*

Farokhzad, O.M., S. Jon, A. Khademhosseini, T.T. Tran, D.A. LaVan, and R. Langer. 2004. Nanoparticle-Aptamer Bioconjugates: A New Approach for Targeting Prostate Cancer Cells. Cancer Research. 64: 7668-7672.*

Coppi, G., V. Iannuccelli, E. Leo, M. T. Bernabei, and R. Cameroni. 2001. Chitosan-Alginate Microparticles as a Protein Carrier. Drug Development and Industrial Pharmacy. 27(5): 393-400.*

(56) References Cited

OTHER PUBLICATIONS

Kawashima Y, et al. Mucoadhesive DL-Lactide/Glycolide Copolymer Nanospheres Coated with Chitosan to Improve Oral Delivery of Elcatonin. Pharm. Dev. Tech. 2000; 5(1): 77-85.*
Bies et al., "Lectin-medicated drug targeting: history and applications," Advanced Drug Delivery Reviews, 56:425-435 (2004).
Brooking et al., "Transport of Nanoparticles Across the Rat Nasal Mucosa," Journal of Drug Targeting, 9(4):267-279 (2001).
Chandy et al., "5-Fluorouracil-loaded chitosan coated polylactic acid microshperes as biodegradable drug carriers for cerebral tumours," J. Mircroencapsulation, 17(5):625-638 (2000).
Chandy et al., "Development of Poly(Lactic Acid)/Chitosan Co-Matrix Microspheres: Controlled Release of Taxol-Heparin for Preventing Restenosis," Drug Delivery, 8:77-86 (2001).
Coppi et al., "Chitosan-Alginate Microparticles as a Protein Carrier," Drug Development and Industrial Pharmacy, 27(5):393-400.
Farokhzad et al., "Nanoparticle-Aptamer Bioconjugates. A new Approach for Targeting Prostate Cancer Cells," Cancer Research, 64:7668-7672 (2004).
Filipovic-Grcic et al., "Mucoadhesive chitosan-coated liposomes: characteristics and stability," J. Microencapsulation, 18(1):3-12 (2001).
Gaserod et al., "The enhancement of the bioadhesive properties of calcium alginate gel beads by coating with chitosan," International Journal of Pharmaceutics, 175:237-246 (1998).
Hejazi et al., "Stomach-specific anti-H. pylori therapy. I: preparation and characterization of tetracyline-loaded chitosan microshpheres," International Journal of Pharmaceutics, 235:87-94 (2002).
Huang et al., "Microencapsulation of Chlorpheniramine Maleate-Resin Particles with Crosslinked Chitosan for Sustained Release," Pharmaceutical Development and Technology, 4(1):107-115 (1999).
Janes et al., "Chitosan nanoparticles as delivery systems for doxorubicin," Journal of Controlled Release, 73:255-267 (2001).
Jayasena, "Aptamers: An Emerging Class of Molecules That Rival Antibodies in Diagnostics," Clinical Chemistry, 45(9):1628-1650 (1999).
Kawashima, et al., "Mucoadhesive DL-Lactide/Glycolide Copolymer Nanoshperes Coated with Chitosan to Improve Oral Delivery of Elcatonin," Pharmaceutical Development and Technology, 5(1):77-85 (2000).
Lehr, "Lectin-mediated drug delivery: The second generation of bioadhesives," Journal of Controlled Release, 65:19-29 (2000).
Lim et al., "Preparation and evaluation of the in vitro drug release properties and mucoadhesion of novel microspheres of hyaluronic acid and chitosan," Journal of Controlled Release, 66:281-292 (2000).
Mi et al., "Release of Indomethacin from a Novel Chitosan Microsphere Prepared by a Natrually Occurring Crosslinker: Examination of Crosslinking and Polycation-Anionic Drug Interaction," Journal of Applied Polymer Science, 81:1700-1711 (2001).
Ponchel, et al., "Specific and non-specific bioadhesive particulate systems for oral delivery to the gastrointestinal tract," Advanced Drug Delivery Reviews, 34:191-219 (1998).
Shimoda et al., "Bioadhesive Characteristics of Chitosan Mircroshperes to the Mucosa of Rat Small Intestine," Drug Delvelopment and Inustrial Pharmacy, 27(6):567-576 (2001).
Takeuchi et al., "Enteral Absorption of Insulin in Rats from Mucoadhesive Chitosan-Coated Liposomes," Pharmaceutical Research, 13(6):896-901 (1996).
Takeuchi et al., "Mucoashesive Lipsomes Coated With Chitosan or Carbopol for Oral Administration of Peptide Drugs," Proceed. Int'l. Symp. Control. Rel. Bioact. Mater., 26:988-989 (1999).
Takeuchi et al., "Spray-Dried Lactose Composite Particles Containing an Ion Complex of Alginate-Chitosan for Desinging a Dry-Coated Tablet Having a Time-Controlled Releasing Function," Pharmaceutical Research, 17(1):94-99 (2000).
Tavitian, et al., "In vivo imaging with oligonucleotides for diagnosis and drug development," Gut, 52(Suppl IV):40-47 (2003).

Tobio et al., "The role of PEG on the stability in digestive fluids and in vivo fate of PEG-PLA nanoparticles following oral administration," Colloids and Surfaces B: Biointerferences, 18:315-323 (2000).
Vila et al., "Design of biodegradable particles for protein delivery," Journal of Controlled Release, 78:15-24 (2002).
Yamada et al., "In Vitro and in Vivo Evaluation of Sustained Release Chitosan-Coated Ketoprofen Microparticles," Yakugaku Zasshi, 121(3):239-245 (2001).
International Search Report, PCT/US05/40100, date of mailing Jul. 15, 2008.
Written Opinion of the International Searching Authority, PCT/US05/40100, date of mailing Jul. 15, 2008.
U.S. Appl. No. 12/239,136, filed Sep. 26, 2008, Farokhzad, et al.
U.S. Appl. No. 12/301,225, filed Nov. 17, 2008, Farokhzad, et al.
U.S. Appl. No. 12/515,465, filed May 5, 2010, Farokhzad, et al.
U.S. Appl. No. 12/526,300, filed Aug. 11, 2010, Moretti, et al.
Abad, et al., "Comparison of a Monoclonal Antibody-Based Enzyme-Linked Immunosorbent Assay and Gas Chromatography for the Determination of Nicotine in Cigarette Smoke Condensates", Anal. Chem., 65:3227-3231 (1993).
Ackermand & Cresswell, "Cellular mechanisms governing cross-presentation of exogenous antigens", Nat. Immunol., 5(7):678-684 (2004).
Aime, et al., "Lanthanide(III) chelates for NMR biomedical applications", Chemical Society Reviews, 27:19-29 (1998).
Akaishi, et al., "Targeting Chemotherapy Using Antibody-Combined Liposome against Human Pancreatic Cancer Cell-Line", Tohoku J. Exp. Med., 175(1):29-42 (1995).
Allen, et al., "Nano-engineering block copolymer aggregates for drug delivery.", Colloids Surfaces B-Biointerfaces, 16:3-27 (1999).
Allison, et al., "The mode of action of immunological adjuvants.", Dev. Biol. Stand., 92:3-11 (1998).
Altschul, et al., "Basic local alignment search tool.", J. Mol Biol., 215(3):403-10 (1990).
Altschul, et al., "Gapped BLAST and PSI-BLAST: a new generation of protein database search programs.", Nucleic Acids Res., 25(17):3389-3402 (1997).
Angelucci, et al., "Neuroendocrine transdifferentiation induced by VPA is mediated by PPAR☐ activation and confers resistance to antiblastic therapy in prostate carcinoma", The Prostate, 68(6):588-598 (2008).
Astete and Sabliov, "Synthesis and characterization of PLGA nanoparticles", J. Biomat. Sci.,-Polymer Ed., 17:247-289 (2006).
Atkinson, et al., "Conjugation of folate via gelonin carbohydrate residues retains ribosomal-inactivating properties of the toxin and permits targeting to folate receptor positive cells.", J. Biol. Chem., 276(30):27930-27935 (2001).
Baba, et al., "Human neutralizing monoclonal antibodies of the IgG1 subtype protect against mucosal simian-human immunodeficiency virus infection.", Nat. Med., 6(2):200-206 (2000).
Babaian, et al., "Radioimmunological imaging of metastatic prostatic cancer with 111indium-labeled monoclonal antibody PAY 276.", J. Urol., 137(3):439-443 (1987).
Bachmann, et al., "T helper cell-independent neutralizing B cell response against vesicular stomatitis virus: role of antigen patterns in B cell induction?", Eur. J. Immunol., 25(12):3445-3451 (1995).
Bagalkot, et al., "An Aptamer-Doxorubicin Physical Conjugate as a Novel Targeted Drug-Delivery Platform", Angew. Chem. Int. Ed., 45(48):8149-8152 (2006).
Bander, et al., "Targeting metastatic prostate cancer with radiolabeled monoclonal antibody J591 to the extracellular domain of prostate specific membrane antigen.", J. Urol., 170(5):1717-1721 (2003).
Barchet, et al., "Virus-induced interferon alpha production by a dendritic cell subset in the absence of feedback signaling in vivo.", J. Exp. Med., 195(4):507-516 (2002).
Barrera, et al., "Synthesis and RGD peptide modification of a new biodegradable copolymer: poly(lactic acid-co-lysine)", J. Am. Chem. Soc., 115(23):11010-11011 (1993).
Bauer, et al., "SMS 201-995: a very potent and selective octapeptide analogue of somatostatin with prolonged action.", Life Sci., 31(11):1133-1140 (1982).

(56) References Cited

OTHER PUBLICATIONS

Beaureparie, et al., "Functionalized Fluorescent Oxide Nanoparticles: Artificial Toxins for Sodium Channel Targeting and Imaging at the Single-Molecule Level", *Nano Letters*, 4(11):2079-2083 (2004).
Bennett, et al., "Inhibition of the Aminopeptidase from Aeromonas Proteolytica by I-Leucinephosphonic Acid, a Transition State Analogue of Peptide Hydrolysis", *J. Am. Chem. Soc.*, 120(46):12139-12140 (1998).
Binetruy-Tournaire, et al., "Identification of a peptide blocking vascular endothelial growth factor (VEGF)-mediated angiogenesis.", *Embo J.*, 19(7):1525-1533 (2000).
Bjerke, et al., "Comparison of monoclonal and polyclonal antibodies to continine in nonisotopic and isotopic immunoassays", *J. Immunol. Meth.*, 96:239-246 (1987).
Boes, et al., "T-cell engagement of dendritic cells rapidly rearranges MHC class II transport.", *Nature*, 418(6901):983-988 (2002).
Bonifaz, et al., "Efficient targeting of protein antigen to the dendritic cell receptor DEC-205 in the steady state leads to antigen presentation on major histocompatibility complex class I products and peripheral CD8+ T cell tolerance.", *J. Exp. Med.*, 196(12):1627-1638 (2002).
Bottausci, et al., "Mixing in the shear superposition micromixer: three-dimensional analysis", *Philosophical Transactions of the Royal Society of London Series a—Mathematical Physical and Engineering Sciences*, 362:1001-1018 (2004).
Boussif, et al., "A versatile vector for gene and oligonucleotide transfer into cells in culture and in vivo: polyethylenimine.", *Proc. Natl. Acad. Sci., USA*, 1995, 92:7297-7301 (1995).
Bozzacco, et al., "DEC-205 receptor on dendritic cells mediates presentation of HIV gag protein to CD8+ T cells in a spectrum of human MHC I haplotypes.", *Proc. Natl. Acad. Sci., USA*, 104(4):1289-1294 (2007).
Brito, et al., "Nanoparticulate carriers for the treatment of coronary restenosis.", *Int J Nanomedicine*, 2(2):143-161 (2007).
Burmeister, et al., "Direct in vitro selection of a 2'-0-methyl aptamer to VEGF.", *Chem Biol*, 12(1):25-33 (2005).
Carino, et al., "Nanosphere based oral insulin delivery," *J. Control. Release*, 65(1-2):261-9 (2000).
Casola, et al., "B cell receptor signal strength determines B cell fate.", *Nat. Immunol.*, 5(3):317-327 (2004).
Castro & Prieto, "Nicotine Antibody Production: Comparison of two nicotine conjugates in different animal species", *Biochem. Biophys. Res. Comm.*, 67(2):583-589 (1975).
Castro, et al., "Nicotine Antibodies: Comparison of Ligand Specificities of Antibodies Produced against Two Nicotine Conjugates", *Eur. J. Biochem.*, 104:331-340 (1980).
Chacon, et al., "Optimized preparation of poly D,L (lactic•glycolic) microspheres and nanoparticles for oral administration", *Int'l J. Pharmaceutics*, 141:81-91 (1996).
Chaires, et al., "Preferential binding of daunomycin to 5'ATCG and 5'ATGC sequences revealed by footprinting titration experiments.", *Biochemistry*, 29(26):6145-6153 (1990).
Chang, et al., "Five Different Anti-Prostate-specific Membrane Antigen (PSMA) Antibodies Confirm PSMA Expression in Tumor-associated Neovasculature", *Cancer Res.*, 59:3192-3198 (1999).
Cheng, et al., "Formulation of functionalized PLGA-PEG nanoparticles for in vivo targeted drug delivery.", *Biomaterials*, 28(5):869-876 (2007).
Christian, et al., "Nucleolin expressed at the cell surface is a marker of endothelial cells in angiogenic blood vessels.", *J. Cell Biol.*, 163(4):871-878 (2003).
Chu, et al., "Aptamer mediated siRNA delivery", *Nuc. Acid Res.*, 34:e73 (2006).
Chu, et al., "Labeling tumor cells with fluorescent nanocrystal-aptamer bioconjugates.", *Biosens. Bioelectron.*, 21:1859-1866 (2006).
Clark, "The reticulum of lymph nodes in mice studied with the electron microscope.", *Am. J. Anat.*, 110:217-257 (1962).

Connor, et al., "Ex vivo evaluation of anti-EpCAM immunocytokine huKS-IL2 in ovarian cancer.", *J. Immunother.*, 27(3):211-219 (2004).
Croy and Kwon, "Polymeric micells for drug delivery", *Curr. Pharm. Design*, 12:4669-4684 (2006).
D'Antonio, et al., "Longitudinal analysis of androgen deprivation of prostate cancer cells identifies pathways to androgen independence", *The Prostate*, 68(7):698-714 (2008).
Dang and Rock, "Stimulation of B lymphocytes through surface Ig receptors induces LFA-1 and ICAM-1-dependent adhesion.", *J. Immunol.*, 146(10):3273-3279 (1991).
De Graaf, et al., "A fully human anti-Ep-CAM scFv-beta-glucuronidase fusion protein for selective chemotherapy with a glucuronide prodrug.", *Br. J. Cancer*, 86(5):811-818 (2002).
De Jaeghere, et al., "Freeze-drying and lyopreservation of diblock and triblock poly(lactic acid)-poly(ethylene oxide) (PLA-PEO) copolymer nanoparticles.", *Pharm. Dev. Technol.*, 5(4):473-483 (2000).
Delemarre, et al., "Repopulation of macrophages in popliteal lymph nodes of mice after liposome-mediated depletion.", *J. Leukoc. Biol.*, 47(3):251-257 (1990).
Demello and Demello, "Microscale reactors: nanoscale products.", *Lab on a Chip*, 4(2):11N-15N (2004).
Demello, "Control and detection of chemical reactions in microfluidic systems.", *Nature*, 442(7101):394-402 (2006).
Deming, et al., "Facile synthesis of block copolypeptides of defined architecture.", *Nature*, 390(6658):386-389 (1997).
Derfus, et al., "Intracellular Delivery of Quantum Dots for Live Cell Labeling and Organelle Tracking", *Advanced Materials*, 16:961-966 (2004).
Dimarco and Arcamone, "DNA complexing antibiotics: Daunomycin, adriamycin and their derivates.", *Arzneim-Forsch. (Drug Res.)*, 25:368-375 (1975).
Ding, et al., "Syntheses of conformationally constricted molecules as potential NAALADase/PSMA inhibitors.", *Org. Lett.*, 6(11):1805-1808 (2004).
Dinkla, et al., "Identification of a streptococcal octapeptide motif involved in acute rheumatic fever.",*J. Biol. Chem.*, 282(26):18686-18693 (2007).
Dykxhoorn, et al., "Killing the messenger: short RNAs that silence gene expression.", *Nat. Rev. Mol. Cell Biol.*, 4(6):457-467 (2003).
Eklund, et al., "Denileukin diftitox: a concise clinical review.", *Expert Rev. Anticancer Ther.*, 5(1):33-38 (2005).
Elbashir, et al., "RNA interference is mediated by 21- and 22-nucleotide RNAs.", *Genes Dev.*, 15(2):188-200 (2001).
Eldridge, et al., "Biodegradable microspheres as a vaccine delivery system," *Mol. Immunol.*, 28(3):287-94 (1991).
Elsässer-Beile, et al., "A new generation of monoclonal and recombinant antibodies against cell-adherent prostate specific membrane antigen for diagnostic and therapeutic targeting of prostate cancer.", *Prostate*, 66(13):1359-1370 (2006).
Farokhzad, et al., "Nanoparticle-Aptamer Bioconjugates: A New Approach for Targeting Prostate Cancer Cells," *Cancer Research*, 64:7668-7672 (2004).
Farokhzad, et al., "Nanoparticle-aptamer bioconjugates for cancer targeting", *Expert Opin. Drug Delivery*, 3(3):311-324 (2006).
Farokhzad, et al., "Targeted nanoparticle-aptamer bioconjugates for cancer chemotherapy in vivo.", *Proc. Natl. Acad. ScL, USA*, 103(16):6315-6320 (2006).
Farr, et al., "The structure of the sinus wall of the lymph node relative to its endocytic properties and transmural cell passage.", *Am. J. Anat.*, 157(3):265-284 (1980).
Fire, et al., "Potent and specific genetic interference by double-stranded RNA in Caenorhabditis elegans.", *Nature*, 391(6669):806-811 (1998).
Fonseca, et al., "Paclitaxel-loaded PLGA nanoparticles: preparation, physicochemical characterization and in vitro anti-tumoral activity.", *J. Control. Release*, 83(2):273-286 (2002).
Fracasso, et al., "Anti-tumor effects of toxins targeted to the prostate specific membrane antigen.", *Prostate*, 53(1):9-23 (2002).

(56) References Cited

OTHER PUBLICATIONS

Francis, et al., "A phase I trial of antibody directed enzyme prodrug therapy (ADEPT) in patients with advanced colorectal carcinoma or other CEA producing tumours.", *Br. J. Cancer*, 87(6):600-607 (2002).
Frankel, et al., "Phase I trial of a novel diphtheria toxin/granulocyte macrophage colony-stimulating factor fusion protein (DT388GMCSF) for refractory or relapsed acute myeloid leukemia.", *Clin. Cancer Res.*, 8(5):1004-1013 (2002).
Frederick, et al., "Structural comparison of anticancer drug-DNA complexes: adriamycin and daunomycin.", *Biochemistry*, 29(10):2538-2549 (1990).
Froidevaux, et al., "Somatostatin analogs and radiopeptides in cancer therapy.", *Biopolymers*, 66(3):161-183 (2002).
Fujita, et al., "Cytokine profiling of prostatic fluid from cancerous prostate glands identifies cytokines associated with extent of tumor and inflammation", *The Prostate*, 68(8):872-882 (2008).
Gao, et al., "A method for the generation of combinatorial antibody libraries using pIX phage display," *Proc. Natl. Acad. Sci. U.S.A.*, 99(20): 12612-6 (2002).
Gao, et al., "In vivo cancer targeting and imaging with semiconductor quantum dots.", *Nat. Biotechnol.*, 22(8):969-976 (2004).
Gao, et al., "In vivo molecular and cellular imaging with quantum dots.", *Curr. Op. Biotechnol.*, 16:63-72 (2005).
Gershlick, "Treating atherosclerosis: local drug delivery from laboratory studies to clinical trials," *Atherosclerosis*, 160(2): 259-71 (2002).
Gillies, et al., "An anti-CD20-IL-2 immunocytokine is highly efficacious in a SCID mouse model of established human B lymphoma.", *Blood*, 105(10):3972-3978 (2005).
Grauer, et al., "Identification, purification, and subcellular localization of prostate-specific membrane antigen PSM' protein in the LNCaP prostatic carcinoma cell line.", *Cancer Res.*, 58(21):4787-4789 (1998).
Gref, et al., "Biodegradable long-circulating polymeric nanospheres.", *Science*, 263(5153):1600-1603 (1994).
Haensler, et al., "Polyamidoamine cascade polymers mediate efficient transfection of cells in culture", *Bioconjugate Chem.*, 4(5):372-379 (1993).
Haj, et al., "New findings in the study on the intercalation of bisdaunorubicin and its monomeric analogues with naked and nucleus DNA.", *Chem. Biol. Interact.*, 145(3):349-358 (2003).
Hanes, et al., "Polymer microspheres for vaccine delivery.", *Pharm. Biotechnol.*, 6:389-412 (1995).
Hangartner, et al., "Antiviral immune responses in gene-targeted mice expressing the immunoglobulin heavy chain of virus-neutralizing antibodies.", *Proc. Natl. Acad. Sci., USA*, 100:12883-12888 (2003).
Hannon, et al., "Unlocking the potential of the human genome with RNA interference", *Nature*, 431(7006):371-378 (2004).
Harada and Kataoka, "Supramolecular assemblies of block copolymers in aqueous media as nanocontainers relevant to biological applications", *Progress Polymer Sci.*, 31(11):949-982 (2006).
Harper, et al., "Efficacy of a bivalent L1 virus-like particle vaccine in prevention of infection with human papillomavirus types 16 and 18 in young women: a randomised controlled trial.", *Lancet*, 364(9447):1757-1765(2004).
Haseloff and Gerlach, "Simple RNA enzymes with new and highly specific endoribonuclease activities.", *Nature*, 334(6183):585-591 (1988).
Hawiger, et al., "Dendritic cells induce peripheral T cell unresponsiveness under steady state conditions in vivo.", *J. Exp. Med.* 194(6):769-779 (2001).
He, et al., "A microRNA polycistron as a potential human oncogene," *Nature*, 435(7043): 828-833 (2005).
Hélène, "The anti-gene strategy: control of gene expression by triplex-forming-oligonucleotides.", *Anticancer Drug Des.* 6(6):569-584 (1991).

Helene, et al., "Control of gene expression by triple helix-forming oligonucleotides. The antigene strategy.", *Ann, N.Y. Acad. Sci.* 660:27-36 (1992).
Hermann and Patel, "Adaptive recognition by nucleic acid aptamers," *Science*, 287: 820-825 (2000).
Hieda, et al., "Active Immunization Alters the Plasma Nicotine Concentration in Rats", *J. Pharmacol. Exp. Therapeutics*, 283:1076-1081 (1997).
Hieda, et al., "Immunization of rats reduces nicotine distribution to brain", *Psychopharmacology*, 143:150-157 (1999).
Horoszewicz, et al., "Monoclonal antibodies to a new antigenic marker in epithelial prostatic cells and serum of prostatic cancer patients.", *Anticancer Res.*, 7(5B):927-935 (1987).
Hotter, et al., "Targeting of a B7-1 (CD80) immunoglobulin G fusion protein to acute myeloid leukemia blasts increases their costimulatory activity for autologous remission T cells.", *Blood*, 97(10):3138-3145 (2001).
Houghton, "General method for the rapid solid-phase synthesis of large numbers of peptides: Specificity of antigen-antibody interaction at the level of individual amino acids", *Immunol.*, 82:5131-5135 (1985).
Jackson, et al., "Design and pharmacological activity of phosphinic acid based NAALADase inhibitors.", *J. Med. Chem.*, 44(24):4170-4175 (2001).
Jackson, et al., "Design of NAALADase inhibitors: a novel neuroprotective strategy.", *Curr. Med. Chem.*, 8(8):949-957 (2001).
Johnson and Prud'Homme, "Mechanism for rapid self-assembly of block copolymer nanoparticles.", *Phys. Rev. Lett.*, 91(11):118302 (2003).
Jones and Leroux, "Polymeric micelles—a new generation of colloidal drug carriers", *Eur. J. Pharmaceutics Biopharmaceutics*, 48:101-111 (1999).
Jung, et al., "Tetanus Toxoid Loaded Nanoparticles from Sulfobutylated Poly(Vinyl Alcohol)-Graft-Poly(Lactide-co-Glycolide): Evaluation of Antibody Response After Oral and Nasal Application in Mice", *Pharmaceutical Research*, 18(3):352-360 (2001).
Junt, et al., "Subcapsular sinus macrophages in lymph nodes clear lymph-borne viruses and present them to antiviral B cells", *Nature*, 450:110-116 (2007).
Kabanov, et al., "DNA Complexes with Polycations for the Delivery of Genetic Material into Cells", *Bioconjugate Chem.*, 6(1):7-20 (1995).
Kamentsky, "Laser scanning cytometry.", *Methods Cell Biol.*, 63:51-87 (2001).
Kanashiro, et al., "Inhibition of mutant p53 expression and growth of DMS-153 small cell lung carcinoma by antagonists of growth hormone-releasing hormone and bombesin.", *Proc. Natl. Acad. Sci., USA*, 100(26):15836-15841 (2003).
Karlin and Altschul, "Applications and statistics for multiple high-scoring segments in molecular sequences.", *Proc. Natl Acad. Sci. USA*, 90(12):5873-5877 (1993).
Karlin and Altschul, "Methods for assessing the statistical significance of molecular sequence features by using general scoring schemes.", *Proc. Natl Acad Sci. USA*, 87:2264-2268 (1990).
Karrer, et al., "On the key role of secondary lymphoid organs in antiviral immune responses studied in alymphoplastic (aly/aly) and spleenless (Hox11(-)/-) mutant mice.", *J. Exp. Med.*, 185(12):2157-2170 (1997).
Kelly, et al., "The Optical Properties of Metal Nanoparticles: The Influence of Size, Shape, and Dielectric Environment", *J. Phys. Chem. B.*, 107(3):668-677 (2003).
Khademhosseini, et al., "Cell docking inside microwells within reversibly sealed microfluidic channels for fabricating multiphenotype cell arrays," *Lab Chip*, 5(12):1380-6 (2005).
Knight, et al., "Hydrodynamic Focusing on a Silicon Chip: Mixing Nanoliters in Microseconds", *Phys. Rev. Lett.*, 80:3863-3866 (1998).
Köhrer and Rajbhandary, "Proteins carrying one or more unnatural amino acids," in Ibba, et al., (eds.), *Aminoacyl-tRNA Synthetases*, Landes Bioscience, Chapter 31 (2005).
Köhrer, et al., "Complete set of orthogonal 21st aminoacyl-tRNA synthetase-amber, ochre and opal suppressor tRNA pairs: concomi-

(56) References Cited

OTHER PUBLICATIONS tant suppression of three different termination codons in an mRNA in mammalian cells.", *Nucleic Acids Res.*, 32(21):6200-6211 (2004).
Köhrer, et al., "Import of amber and ochre suppressor tRNAs into mammalian cells: a general approach to site-specific insertion of amino acid analogues into proteins.", *Proc. Natl. Acad. Sci., USA*, 98(25):14310-14315 (2001).
Koivunen, et al., "Phage libraries displaying cyclic peptides with different ring sizes: ligand specificities of the RGD-directed integrins.", *Biotechnology (NY)*, 13(3):265-270 (1995).
Koivunen, et al., "Tumor targeting with a selective gelatinase inhibitor", *Nat. Biotechnol.*, 17:768-774 (1999).
Konan, et al., "Preparation and characterization of sterile sub•200 nm meso-tetra(4-hydroxylphenyl)porphyrin-loaded nanoparticles for photodynamic therapy", *Eur. J. Pharmaceutics Biopharmaceutics*, 55:115-124 (2003).
Kozikowski, et al., "Synthesis of urea-based inhibitors as active site probes of glutamate carboxypeptidase II: efficacy as analgesic agents.", *J. Med. Chem.*, 47(7):1729-1738 (2004).
Krieg, et al., "CpG motifs in bacterial DNA trigger direct B-cell activation.", *Nature*, 374(6522):546-549 (1995).
Kreitman, et al, "Efficacy of the anti-CD22 recombinant immunotoxin BL22 in chemotherapy-resistant hairy-cell leukemia.", *N. Engl J. Med.*, 345(4):241-347 (2001).
Kreitman, et al., "Phase I trial of recombinant immunotoxin anti-Tac(Fv)-PE38 (LMB-2) in patients with hematologic malignancies.", *J. Clin. Oncol.*, 18(8):1622-1636 (2000).
Kukowska-Latallo, et al., "Efficient transfer of genetic material into mammalian cells using Starburst polyamidoamine dendrimers", *Proc. Natl. Acad. Sci., USA*, 93(10):4897-4902 (1996).
Kumar, et al., "Inhibition of angiogenesis and tumor growth by SCH221153, a dual alpha(v)beta3 and alpha(v)beta5 integrin receptor antagonist.", *Cancer Res.*, 61(5):2232-2238 (2001).
Kwon, et al., "Pseudopoly(amino acids): A study of the synthesis and characterization of poly(acyl-hydroxyproline-esters)", *Macromolecules*, 22:3250-3255 (1989).
Laakkonen, et al., "Antitumor activity of a homing peptide that targets tumor lymphatics and tumor cells.", *Proc. Natl. Acad. Sci., USA*, 101(25):9381-9386 (2004).
Labhasetwar, et al., "Arterial uptake of biodegradable nanoparticles: Effect of surface modifications," *J. Pharm. Sci.*, 87(10):1229-34 (1998).
Langer, "Biomaterials in drug delivery and tissue engineering: one laboratory's experience.", *Acc. Chem. Res.*, 33(2):94-101 (2000).
Langer, "New methods of drug delivery," *Science*, 249(4976):1527-33 (1990).
Langer, "Selected advances in drug delivery and tissue engineering", *J. Control. Release*, 62:7-11 (1999).
Langone, et al., "Nicotine and its metabolites. Radioimmunoassays for nicotine and cotinine", *Biochem.*, 12(24):5025-5030 (1973).
Langone & Van Vunakis, "Radioimmunoassay of Nicotine, Cotinine, and ☐-(3-Pyridyl)-☐-oxo-N-methylbutyramide", *Met. Enzymol.*, 84:628-640 (1982).
Leamon, et al., "Cytotoxicity of folate-Pseudomonas exotoxin conjugates toward tumor cells. Contribution of translocation domain.", *J. Biol. Chem.*, 268(33):24847-24854 (1993).
Leamon, et al., "Selective targeting of malignant cells with cytotoxin-folate conjugates.", *J. Drug Target.*, 2(2):101-112 (1994).
Leopold, et al., "Fluorescent virions: dynamic tracking of the pathway of adenoviral gene transfer vectors in living cells.", *Human Gene Therapy*, 9(3):367-378 (1998).
Leroy, et al., "Radioimmunodetection of lymph node invasion in prostatic cancer. The use of iodine 123 (123I)-labeled monoclonal anti-prostatic acid phosphatase (PAP) 227 A F(ab')2 antibody fragments in vivo.", *Cancer*, 64(1):1-5 (1989).
Leucuta, et al., "Albumin microspheres as a drug delivery system for epirubicin: pharmaceutical, pharmacokinetic and biological aspects," *International Journal of Pharmaceutics*, 41: 213-7 (1988).

Lim, et al., "A Self-Destroying Polycationic Polymer: Biodegradable Poly(4-hydroxy-l-proline ester)", *J. Am. Chem. Soc.*, 121(24):5633-5639 (1999).
Lim, et al., "Cationic hyperbranched poly(amino ester): a novel class of DNA condensing molecule with cationic surface, biodegradable three-dimensional structure, and tertiary amine groups in the interior.", *J. Am. Chem. Soc*, 123(10):2460-2461 (2001).
Lin, et al., "A microRNA polycistron as a potential human oncogene p828", *Nature*, 435(7043):828-833 (2005).
Lin, et al., "Well-Ordered Mesoporous Silica Nanoparticles as Cell Markers", *Chem. Mater.*, 17:4570-4573 (2005).
Liu, et al., "Cell-Surface labeling and internalization by a fluorescent inhibitor of prostate-specific membrane antigen", *The Prostate*, 68(9):955-964 (2008).
Liu, et al., "Constitutive and antibody-induced internalization of prostate-specific membrane antigen.", *Cancer Res.*, 58(18):4055-4060 (1998).
Liu, et al., "Folate-targeted enzyme prodrug cancer therapy utilizing penicillin-V amidase and a doxorubicin prodrug.", *J. Drug Target.*, 7:43-53 (1999).
Liu, et al., "Hypermethylation of MCAM gene is associated with advanced tumor stage in prostate cancer", *The Prostate*, 68(4):418-426 (2008).
Liu, et al., "Monoclonal antibodies to the extracellular domain of prostate-specific membrane antigen also react with tumor vascular endothelium.", *Cancer Res.*, 57(17):3629-3634 (1997).
Low, et al., "Folate receptor-targeted drugs for cancer and inflammatory diseases.", *Adv. Drug Deliv. Rev.*, 56(8):1055-1058 (2004).
Lu, et al., "MicroRNA expression profiles classify human cancers", *Nature*, 435(7043):834-838 (2005).
Ludewig, et al., "Induction of optimal anti-viral neutralizing B cell responses by dendritic cells requires transport and release of virus particles in secondary lymphoid organs.", *Eur. J. Immunol.*, 30(1):185-196 (2000).
Lupold, et al., "Identification and characterization of nuclease-stabilized RNA molecules that bind human prostate cancer cells via the prostate-specific membrane antigen.", *Cancer Res.*, 62(14):4029-4033 (2002).
Lyu, et al., "The immunocytokine scFv23/TNF sensitizes HER-2/neu-overexpressing SKBR-3 cells to tumor necrosis factor (TNF) via up-regulation of TNF receptor-1.", *Mol. Cancer Ther.*, 4(8):1205-1213 (2005).
Maher, "DNA triple-helix formation: An approach to artificial gene repressors?", *Bioassays* 14:807-815 (1992).
Majer, et al., "Synthesis and biological evaluation of thiol-based inhibitors of glutamate carboxypeptidase II: discovery of an orally active GCP II inhibitor.", *J. Med. Chem.*, 46(10)1989-1996 (2003).
Manolova, et al., "Nanoparticles target distinct dendritic cell populations according to their size", *Eur. J. Immunol.*, 38:1404-1413 (2008).
Manz, et al., "Capillary electrophoresis on a chip", *J. Chromatography*, 593:253-258 (1992).
Mathiowitz, et al., "Polyanhydride Microspheres as Drug Carriers I. Hot Melt Encapsulation", *J. Control. Release*, 5:13-22 (1987).
Mathiowitz, et al., "Novel microcapsules for delivery systems", *Reactive Polymers*, 6:275-283 (1987).
Mathiowitz, et al., "Polyanhydride Microspheres as Drug Carriers. II.Microencapsulation by Solvent Removal", *J. Appl. Polymer Sci.*, 35:755-774 (1988).
Mattheakis, et al., "Optical coding of mammalian cells using semiconductor quantum dots.", *Analytical Biochemistry*, 327(2):200-208 (2004).
Maung, et al., "Probing for a hydrophobic a binding register in prostate-specific membrane antigen with phenylalkylphosphonamidates.", *Bioorg. Med. Chem.*, 12(18):4969-4979 (2004).
McDevitt, et al., "An alpha-particle emitting antibody ([213Bi]J591) for radioimmunotherapy of prostate cancer.", *Cancer Res.*, 60(21):6095-6100 (2000).
McDevitt, et al., "Tumor therapy with targeted atomic nanogenerators.", *Science*, 294(5546):1537-1540 (2001).

(56) References Cited

OTHER PUBLICATIONS

Mead, et al., "Laboratory vector competence of black flies (Diptera:Simuliidae) for the Indiana serotype of vesicular stomatitis virus.", *Ann. N.Y. Acad. Sci.*, 916:437-443 (2000).
Meister, et al., "Mechanisms of gene silencing by double-stranded RNA.", *Nature*, 431(7006):343-349 (2004).
Melani, et al., "Targeting of interleukin 2 to human ovarian carcinoma by fusion with a single-chain Fv of antifolate receptor antibody.", *Cancer Res.*, 58(18):4146-4154 (1998).
Mempel, et al., "T-cell priming by dendritic cells in lymph nodes occurs in three distinct phases.", *Nature*, 427(6970):154-159 (2004).
Metelitsa, et al., "Antidisialoganglioside/granulocyte macrophage-colony-stimulating factor fusion protein facilitates neutrophil antibody-dependent cellular cytotoxicity and depends on FcgammaRII (CD32) and Mac-1 (CD11b/CD18) for enhanced effector cell adhesion and azurophil granule exocytosis.", *Blood*, 99(11):4166-4173 (2002).
Meyers, et al., "Development of monoclonal antibody imaging of metastatic prostatic carcinoma.", *Prostate*, 14(3):209-220 (1989).
Milligan and Uhlenbeck, "Synthesis of small RNAs using T7 RNA polymerase," *Methods in Enzymology*, 180: 51-62 (1989).
Moghimi, et al., "Long-circulating and target-specific nanoparticles: theory to practice," *Pharmacol. Rev.*, 53(2): 283-318 (2001).
Mulligan, "The basic science of gene therapy," *Science*, 260(5110):926-32 (1993).
Murphy, et al., "Isolation and characterization of monoclonal antibodies specific for the extracellular domain of prostate specific membrane antigen.", *J. Urol.*, 160(6 Pt 2):2396-2401 (1998).
Murray, et al., "Synthesis and characterization of monodisperse nanocrystals and close-packed nanocrystal assemblies", *Ann. Rev. Mat. Sci.*, 30:545-610 (2000).
Myers and Miller, *CABIOS* (1988).
Nan, et al., "Dual function glutamate-related ligands: discovery of a novel, potent inhibitor of glutamate carboxypeptidase II possessing mGluR3 agonist activity.", *J. Med. Chem.*, 43(5):772-774 (2000).
Neidle, "The molecular basis for the action of some DNA-binding drugs.", *Prog. Med. Chem.*, 16:151-221 (1979).
Nguyen and Wu, "Micromixers—a review.", *J. Micromechan. Microeng.*, 15:R1 (2005).
Notter, et al., "Targeting of a B7-1 (CD80) immunoglobulin G fusion protein to acute myeloid leukemia blasts increases their costimulatory activity for autologous remission T cells.", *Blood*, 97(10):3138-3145 (2001).
O'Donnell, et al., "c-Myc-regulated microRNAs modulate E2F1 expression", *Nature*, 435(7043):839-843 (2005).
Ochsenbein, et al., "Protective T cell-independent antiviral antibody responses are dependent on complement.", *J. Exp. Med.*, 190(8):1165-1174 (1999).
Ochsenbein, et al., "Control of early viral and bacterial distribution and disease by natural antibodies.", *Science*, 286(5447):2156-2159 (1999).
O'Donnell, et al., "c-Myc-regulated microRNAs modulate E2F1 expression," *Nature*, 435(7043): 839-843 (2005).
Okada, et al., "Antigen-engaged B cells undergo chemotaxis toward the T zone and form motile conjugates with helper T cells.", *PLoS Biol.*, 3(6):e150 (2005).
Oliver, et al., "Conformational and SAR analysis of NAALADase and PSMA inhibitors.", *Bioorg. Med. Chem.*, 11(20):4455-4461 (2003).
Pape, et al., "The humoral immune response is initiated in lymph nodes by B cells that acquire soluble antigen directly in the follicles.", *Immunity*, 26(4):491-502 (2007).
Papisov, "Acyclic Polyacetals from Polysaccharides: Biomimetic Biomedical "Stealth" Polymers", *ACS Symposium Series*, 786:301-314 (2001).
Parekh, et al., "Biomarkers for Prostate Cancer Detection", *The Journal of Urology*, 178(6):2252-2259 (2007).
Pasqualini, et al., "Aminopeptidase N is a receptor for tumor-homing peptides and a target for inhibiting angiogenesis.", *Cancer Res.*, 60(3):722-727 (2000).
Patri, et al., "Synthesis and in Vitro Testing of J591 Antibody—Dendrimer Conjugates for Targeted Prostate Cancer Therapy", *Bioconj. Chem.*, 15:1174-1181 (2004).
Pellegrino, et al., "On the development of colloidal nanoparticles towards multifunctional structures and their possible use for biological applications.", *Small*, 1(1):48-63 (2005).
Pfohl, et al., "Trends in microfluidics with complex fluids.", *Chemphyschem*, 4(12):1291-1298 (2003).
Phillips, et al., "Enhanced antibody response to liposome-associated protein antigens: preferential stimulation of IgG2a/b production.", *Vaccine*, 10(3):151-158 (1992).
Porkka, et al., "A fragment of the HMGN2 protein homes to the nuclei of tumor cells and tumor endothelial cells in vivo.", *Proc. Natl. Acad. Sci., USA*, 99(11):7444-7449 (2002).
Putnam, et al., "Poly(4-hydroxy-l-proline ester): Low-Temperature Polycondensation and Plasmid DNA Complexation", *Macromolecules*, 32(11):3658-3662 (1999).
Qi, et al., "Extrafollicular activation of lymph node B cells by antigen-bearing dendritic cells", *Science*, 312(5780):1672-1676 (2006).
Quintanar-Guerrero, et al., "Preparation Techniques and Mechanisms of Formation of Biodegradable Nanoparticles from Preformed Polymers", *Drug Dev. Industrial Pharmacy*, 24(12):1113-1128 (1998).
Reddy, et al., "Exploiting lymphatic transport and complement activation in nanoparticle vaccines", *Nat. Biotech.*, 25(10):1159-1164 (2007).
Reif, et al., "Balanced responsiveness to chemoattractants from adjacent zones determines B-cell position.", *Nature*, 416(6876):94-99 (2002).
Reiher, et al., "Inhibition of tumor growth by systemic treatment with thrombospondin-1 peptide mimetics.", *Int. J. Cancer*, 98(5):682-689 (2002).
Reubi, et al., "Peptide receptors as molecular targets for cancer diagnosis and therapy.", *Endocr. Rev.*, 24(4):389-427 (2003).
Reynolds, et al., "Rational siRNA design for RNA interference.", *Nat. Biotechnol.*, 22(3):326-330 (2004).
Robbins, et al., "Stable expression of shRNAs in human CD34+ progenitor cells can avoid induction of interferon responses to siRNAs in vitro", *Nature Biotechnology*, 24(5):566-571 (2006).
Robinson, et al., "LEAPT: lectin-directed enzyme-activated prodrug therapy.", *Proc. Natl. Acad. Sci., USA*, 101(40):14527-14532 (2004).
Roost, et al., "Mapping of the dominant neutralizing antigenic site of a virus using infected cells.", *J. Immunol. Methods*, 189(2):233-242 (1996).
Rossbacher and Shlomchik, "The B cell receptor itself can activate complement to provide the complement receptor 1/2 ligand required to enhance B cell immune responses in vivo.", *J. Exp. Med.*, 198(4):591-602 (2003).
Sampson, et al., "Progress report of a Phase I study of the intracerebral microinfusion of a recombinant chimeric protein composed of transforming growth factor (TGF)-alpha and a mutated form of the Pseudomonas exotoxin termed PE•38 (TP•38) for the treatment of malignant brain tumors.", *J. Neurooncol.*, 65(1):27-35 (2003).
Santoyo, et al., "Highly specific and accurate selection of siRNAs for high-throughput functional assays.", *Bioinformatics*, 21(8):1376-1382 (2005).
Sarver, et al., "Ribozymes as potential anti-HIV-1 therapeutic agents.", *Science* 247(4947):1222-1225 (1990).
Schally, et al., "Peptide analogs in the therapy of prostate cancer.", *Prostate*, 45(2):158-166 (2000).
Schultz, "Plasmon resonant particles for biological detection", *Curr. Op. Biotechnol.*, 14:13-22 (2003).
Schultz, et al., "Single-target molecule detection with nonbleaching multicolor optical immunolabels.", *Proc. Natl. Acad. Sci., USA*, 97(3):996-1001(2000).
Shaida, et al., "Expression of BNIP3 correlates with hypoxia-inducible factor (HIF)-1□, HIF-2□ and the androgen receptor in

(56) References Cited

OTHER PUBLICATIONS prostate cancer and is regulated directly by hypoxia but not androgens in cell lines", *The Prostate*, 68(3):336-343 (2008).
Shen, et al., "Enhanced and prolonged cross-presentation following endosomal escape of exogenous antigens encapsulated in biodegradable nanoparticles", *Immunol.*, 117:78-88 (2006).
Shestopalov, et al., "Multi-step synthesis of nanoparticles performed on millisecond time scale in a microfluidic droplet-based system.", *Lab on a Chip*, 4(4):316-321 (2004).
Shiow, et al., "CD69 acts downstream of interferon-alpha/beta to inhibit S1P1 and lymphocyte egress from lymphoid organs.", *Nature*, 440(7083):540-544 (2006).
Silver, et al., "Prostate-specific membrane antigen expression in normal and malignant human tissues.", *Clin. Cancer Res.*, 3(1):81-85 (1997).
Smith-Jones, et al., "In vitro characterization of radiolabeled monoclonal antibodies specific for the extracellular domain of prostate-specific membrane antigen.", *Cancer Res.*, 60(18):5237-5243 (2000).
Sondel, et al., "Preclinical and clinical development of immunocytokines.", *Curr. Opin. Investig. Drugs*, 4(6):696-700 (2003).
Song, et al., "A Microfluidic System for Controlling Reaction Networks in Time", *Angewandte Chemie-Int'l Ed.*, 42:768-772 (2003).
Spooner, et al., "A novel vascular endothelial growth factor-directed therapy that selectively activates cytotoxic prodrugs.", *Br. J. Cancer*, 88(10):1622-1630 (2003).
Stoermer, et al., "Synthesis and biological evaluation of hydroxamate-Based inhibitors of glutamate carboxypeptidase II.", *Bioorg. Med. Chem. Lett.*, 13(13):2097-2100 (2003).
Storm, et al., "Surface Modification of Nanoparticles to Oppose Uptake by the Mononuclear Phagocyte System", *Adv. Drug Deliv. Rev.*, 17:31-48 (1995).
Stroock, et al., "Chaotic mixer for microchannels.", *Science*, 295(5555):647-651 (2002).
Sutcliffe, et al., "Antibodies that react with predetermined sites on proteins", *Science*, 219:660-666 (1983).
Tang, et al., "In Vitro Gene Delivery by Degraded Polyamidoamine Dendrimers", *Bioconjugate Chem.*, 7:703-714 (1996).
Tang, et al., "Prostate targeting ligands based on N-acetylated alpha-linked acidic dipeptidase.", *Biochem. Biophys. Res. Commun.*, 307(1):8-14 (2003).
Taylor, et al., "Macrophage receptors and immune recognition.", *Annu. Rev. Immunol.*, 23:901-944 (2005).
Tindall, et al., "The Rationale for Inhibiting 5☐-Reductase Isoenzymes in the Prevention and Treatment of Prostate Cancer", *The Journal of Urology*, 179(4):1235-1242 (2008).
Trindade, et al., "Nanocrystalline Semiconductors: Synthesis, Properties, and Perspectives", *Chem. Mat.*, 13(11):3843-3858 (2001).
Tsukamoto, et al., "Phosphonate and phosphinate analogues of N-acylated gamma-glutamylglutamate. potent inhibitors of glutamate carboxypeptidase II.", *Bioorg. Med. Chem. Lett.*, 12(16):2189-2192 (2002).
Uhrich, et al., "Polymeric Systems for Controlled Drug Release", *Chem. Rev.*, 99(11):3181-3198 (1999).
Unkeless, et al., "Structure and function of human and murine receptors for IgG.", *Annu. Rev. Immunol.*, 6:251-281 (1998).
Uwatoku, et al., "Application of Nanoparticle Technology for the Prevention of Restenosis After Balloon Injury in Rats," *Circ. Res.*, 92(7): e62-9 (2003).
Valentini, et al., "Association of anthracycline derivatives with DNA: a fluorescence study.", *Farmaco [Sci]*, 40:377-390 (1985).
Vallabhajosula, et al., "Radioimmunotherapy of prostate cancer in human xenografts using monoclonal antibodies specific to prostate specific membrane antigen (PSMA): studies in nude mice.", *Prostate*, 58(2):145-155 (2004).
Vascotto, et al., "Antigen presentation by B lymphocytes: how receptor signaling directs membrane trafficking.", *Curr., Opin., Immunol.*, 19(1):93-98 (2007).

Vihko, et al., "Radioimaging of Prostatic Carcinoma With Prostatic Acid Phosphatase—Specific Antibodies", *Biotechnology in Diagnostics*, 131-134 (1985).
Von Allmen, et al., "V domain of RAGE interacts with AGEs on prostate carcinoma cells", *The Prostate*, 68(7):748-758 (2008).
Von Andrian and Mempel, "Homing and cellular traffic in lymph nodes.", *Nat. Rev. Immunol.*, 3(11):867-878 (2003).
Wang, et al., "A novel biodegradable gene carrier based on polyphosphoester.", *J. Am. Chem. Soc.*, 123(38):9480-9481 (2001).
Wang, et al., "Autoantibody signatures in prostate cancer.", *N Engl J Med*, 353(12):1224-1235 (2005).
Wang, et al., "Identification of prostate specific membrane antigen (PSMA) as the target of monoclonal antibody 107-1A4 by proteinchip; array, surface-enhanced laser desorption/ionization (SELDI) technology.", *Int. J. Cancer*, 92(6):871-876 (2001).
Wang, et al., "Interactions between an anthracycline antibiotic and DNA: molecular structure of daunomycin complexed to d(CpGpTpApCpG) at 1.2-A resolution.", *Biochemistry*, 26(4):1152-1163 (1987).
Weaver, et al., "Transferrin receptor ligand-targeted toxin conjugate (Tf-CRM107) for therapy of malignant gliomas.", *J. Neurooncol.*, 65(1):3-13 (2003).
Wessels, et al., "Studies of group B streptococcal infection in mice deficient in complement component C3 or C4 demonstrate an essential role for complement in both innate and acquired immunity.", *Proc. Natl. Acad. Sci., USA*, 92(25):11490-11494 (1995).
Whelan, et al., "Efficient recovery of infectious vesicular stomatitis virus entirely from cDNA clones.", *Proc. Natl. Acad. Sci., USA*, 92(18):8388-8392 (1995).
Wilson, et al., "The Structure of an Antigenic Determinant in a Protein", *Cell*, 37:767-778 (1984).
Wind, et al., "An integrated confocal and magnetic resonance microscope for cellular research.", *J. Magn. Reson.*, 147(2):371-377 (2000).
Wlotzka, et al., "In vivo properties of an anti-GnRH Spiegelmer: an example of an oligonucleotide-based therapeutic substance class," *Proc. Natl. Acad. Sci. U. S. A.*, 99(13):8898-902 (2002).
Wright, et al., "Cyclophosphamide/granulocyte colony-stimulating factor causes selective mobilization of bone marrow hematopoietic stem cells into the blood after M phase of the cell cycle.", *Blood*, 97(8):2278-2285 (2001).
Wu, "Arming antibodies: prospects and challenges for immunoconjugates.", *Nat. Biotechnol.*, 23(9):1137-1146 (2005).
Wu, et al., "Immunofluorescent labeling of cancer marker Her2 and other cellular targets with semiconductor quantum dots.", *Nat. Biotechnol.*, 21(1):41-46 (2003).
Yang, "Imaging of vascular gene therapy.", *Radiology*, 228:36-249 (2003).
Yoo, et al., "In vitro and in vivo anti-tumor activities of nanoparticles based on doxorubicin-PLGA conjugates.", *J. Control. Release*, 68(3):419-431 (2000).
Yuan, et al., "siRNA Selection Server: an automated siRNA oligonucleotide prediction server.", *Nucl. Acids. Res.*, 32:W130-W134 (2004).
Zamore, et al., "RNAi: double-stranded RNA directs the ATP-dependent cleavage of mRNA at 21 to 23 nucleotide intervals.", *Cell*, 101(1):25-33 (2000).
Zauner, et al., "Polylysine-basedtransfection systems utilizing receptor-mediated delivery.", *Adv. Drug Del. Rev.*, 30:97-113 (1998).
Zhang, et al., "The proliferative effect of estradiol on human prostate stromal cells is mediated through activation of ERK", *The Prostate*, 68(5):508-516 (2008).
Zheng, et al., "Highly fluorescent, water-soluble, size-tunable gold quantum dots.", *Phys. Rev. Lett.*, 93(7):077402 (2004).
Zhou, et al., "Investigation on a novel core-coated microspheres protein delivery system.", *J. Control. Release*, 75(1-2):27-36 (2001).
Zhou, et al., "Preparation of poly(L-serine ester): a structural analog of conventional poly(L-serine)", *Macromolecules*, 23(14):3399-3406 (1990).
Zuker, "Mfold web server for nucleic acid folding and hybridization prediction", *Nuc. Acid. Res.*, 31:3406-3415 (2003).

(56) References Cited

OTHER PUBLICATIONS

Akagi, et al., "Development of vaccine adjuvants using polymeric nanoparticles and their potential applications for anti-HIV vaccine", Yakugaku Zasshi, 127(2):307-17 (2007) English Abstract.

Akagi, et al., "Multifunctional conjugation of proteins on/into bio-nanoparticles prepared by amphiphilic poly(gamma-glutamic acid)", J Biomat Sci Polym Ed., 17(8):875-92 (2006).

Argov-Argaman, et al., "Lactosomes: Structural and compositional classification of unique nanometer-sized protein lipid particles of human milk", J Agric Food Chem., 58:11234-42 (2010).

Avgoustakis, "Pegylated poly(lactide) and poly(lactide-co-glycolide) nanoparticles: preparation, properties and possible applications in drug delivery", Curr Drug Deliv., 1:321-33 (2004).

Chu, et al, "Aptamer:toxin conjugates that specifically target prostate tumor cells", Cancer Res., 66:5989-92 (2006).

Elamanchili, et al., "Pathogen-mimicking" nanoparticles for vaccine delivery to dendritic cells, J Cont. Rel., 30(4):378-95 (2007).

Gorelik, et al., "Scanning surface confocal microscopy for simultaneous topographical and fluorescence imaging: application to single virus-like particle entry into a cell", PNAS, 99(25):16018-23 (2002).

Hallahanm, et al., "Integrin-mediated targeting of drug delivery to irradiated tumor blood vessels", Cancer Cell, 3:63-74 (2003).

Harris, et al., "Proteolytic actuation o nanoparticle self-assembly", Angewandte Chemie, 118:3233-7 (2006).

Hennenfent, et al., "Novel formulations of taxanes: a review. Old wine in a new bottle", Ann Oncol., 17:735-49 (2005).

Jayaprakash, et al., "Design and synthesis of a PSMA inhibitor-doxorubicin conjugate for targeted prostate cancer therapy", Chem Med Chem., 1:299-302 (2006).

Kawamura, et al., "Dendritic cells that endocytosed antigen-containing IgG-liposomes elicit effective antitumor immunity", J Immunother., 29(2):165-74 (2006).

Koenig, et al., "Immunologic factors in human milk: the effects of gestational age and pasteurization", J Human Lactation, 21:439-43 (2002).

Lamalle-Bernard, et al., "Coadsorption of HIV-1 p24 and gp120 proteins to surfactant-free anionic PLA nanoparticles preserves antigenicity and immunogenicity", J Control Rel., 115(1):57-67 (2006).

Martin, et al., "Crystal structure at 2.8 A of an FcRn/heterodimeric Fc complex: mechanism of pH-dependent binding.", Mol Cell, 7:867-77 (2001).

Matsuo, et al., "Efficient generation of antigen-specific cellular immunity by vaccination with poly (gamma-glutamic acid) nanoparticles entrapping endoplasmic reticulum-targeted peptides", Biochem Biophys Res Commun., 362:1069-72 (2007).

McNeil, "Nanotechnology for the biologist", J Leukoc Biol., 78:575-94 (2005).

Moon, et al., "Engineering Nano- and microparticles to tune immunity", Adv Mater., DOI:10.1002/adma.201200446 (2012).

Oyewumi, et al., "Comparison of cell uptake, biodistribution and tumor retention of folate-coated and PEG-coated gadolinium nanoparticles in tumor-bearing mice", J Control Rel., 93:613-26 (2004).

Oyewumi, et al., "Nano-microparticles as immune adjuvants: correlating particle sizes and the resultant immune responses", Exp Rev Vaccines, 9(9):1095-1107 (2010).

Riley, et al., "Colloidal stability and drug incorporation aspects of micellar-like PLA-PEG nanoparticles", Colloids Surfaces B Biointerfaces, 16:147-59 (1999).

Shields, et al., "High resolution mapping of the binding site on human IgG1 for Fc gamma RI, Fc gamma RII, Fc gamma RIII, and FcRn and design of IgG1 variants with improved binding to the Fc gamma R", J Biolo Chem., 276(9):6591-6604 (2001).

Shim, "One target different effects: a comparison of distinct therapeutic antibodies against the same targets", Exp Mole Med. ,43(10):539-49 (2011).

Suzuki, et al., "Development of effective antigen delivery carrier to dendritic cells via Fc receptor in cancer immunotherapy", Yakugaku Zasshi, 127(2):301-6 (2007). English Abstract.

Taylor, et al., "Development of a specific system for targeting protein to metallophilic macrophages", PNAS, 101(7):1963-8 (2004).

Uto, et al., "Targeting of antigen to dendritic cells with poly(gamma-glutamic acid) nanoparticies induces antigen-specific humoral and cellular immunity", J Immunology, 178(5):2979-86 (2007).

Wakita, et al., "An indispensable role of type-1 IFNs for inducing CTL-mediated complete eradication of established tumor tissue by CpG-liposome co-encapsulated with model tumor antigen", Int. Immunol., 18(3):425-34 (2006).

Yu, et al., "Engineered bio-nanocapsules, the selective vector for drug delivery system", IUBMB Like, 58(1):1-6 (2006).

Bocca, et al., "Phagocytic uptake of fluorescent stealth solid lipid nanoparticles", *Int. J. Pharmaceutics*, 175:185-193 (1998).

Elvassore, et al., "Production iof Insulin-Loaded Poly(Ethylene Glycol)/Poly(/-Lactide) (PEG/PLA) Nanoparticles by Gas Antisolvent Techniques", *Journal of Pharmacrutical Sciences*, 90(10)1628-36 (2001).

Heald, et al., "Poly(lactic acid)-poly(ethylene oxide) (PLA-PEG) nanoparticles: NMR studies of the central solidlike PLA core and the liquid PEG corona", *Langmuir*, 18:3669-3675 (2002).

Khandare, et al., "Polymer-drug conjugates: Progress in polymeric prodrugs," *Progress in Polymer Science*, 31(4): 359-397 (2006).

Kim, et al., "Target-specific cellular uptake of PLGA nanoparticles coated with poly(L-lysine)-poly(ethyleneglycol)-folate conjugate", *Langmuir*, 21(19): 8852-8857 (2005).

Olivier, et al., "Drug Transport to Brain with Targeted Nanoparticles", *J. of the Am. Society of Experimental NeuroTherapeutics*, 2:108-119 (2005).

Pimentel, et al., "Peptide nanoparticles as novel immunogens: design and analysis of a prototypic severe acute respiratory syndrome vaccine", *Chemical Biology & Drug Design*, 73(1):53-61 (2009).

Sarkar, et al., "Ligand-DNA interaction in a nanocage of reverse micelle", Biopolymer., 83(6):675-86 (2006).

Simberg, et al., "Biomimetic amplification of nanoparticle homing to tumors", *Nat'l. Acad. Sic. USA*, 104(3):921-936 (2007).

Tomai, et al., "Resiquimod and other immune response modifiers as vaccine adjuvants", Expert Rev Vaccines, 6:835-847 (2007) Abstract Only.

Vila, et al., "PLA-PEG Nanospheres: New Carriers for Transmucosal Delivery of Proteins and Plasmid DNA", *Poly. Adv. Technol.*, 13:851-858 (2002).

Villa, et al., "PLA-PEG particles as nasal protein carriers: the influence of the particle size", *Int. J Pharmaceut.*, 292:43-52 (2005).

Yourong, et al, "Preparation of DHAQ-loaded mPEG-PLGA-mPEG nanoparticles and evaluation of drug release behaviors in vitro/in vivo," *J. Mat. Sci.: Mat. Med.*, 17(6): 509-16 (2006).

Yuan, et al., "Intranasal immunization with chitosan/pCETP nanoparticles inhibits atherosclerosis in a rabbit model of atherosclerosis", *Vaccine, Bitterworth Scientific*, 26:29-30 (2008).

Cerchia, et al. "Neutralizing aptamers from whole-cell SELEX inhibit the RET receptor tyrosine kinase", PLoS Biology, 3(4):849-60 (2005).

Foss, et al., "Radiolabeled small-molecule ligands for prostate-specific membrane antigen: in vivo imaging in experimental models of prostate cancer", Clin. Cancer Res., 11:4022-28 (2005).

Govender, et al., "Defining the drug incorporation properties of PLA-PEG nanoparticles", Intl J of Pharmaceutics, 1999:95-110(2000).

Mitra, et al., "Tumour targeted delivery of encapsulated dextran-doxorubicin conjugate using chitosan nanoparticles as carrier", J Controlled Release, 74:317-23 (2001).

Wu, et al., Selection of oligonucleotide apatamers with enhanced uptake and activation of human leukemia B cells,, Human Gene., 14:849-860 (2003).

Zhou, et al., "NAAG peptidase inhibitors and their potential for diagnosis and therapy", Nature Rev. Drug Disc., 4:1015-26 (2005).

(56) References Cited

OTHER PUBLICATIONS

Beck, et al., "A New Long-acting Injectable Microcapsule System for the Administration of Progesterone," Fertil. & Steril., 31(5):545-55 (1979).
Benita, et al., "Characterization of Drug-Loaded Poly(d,/-lactide) Microspheres," J. Pharm. Sci. 73(12):1721-24 (1984).
Chickering & Mathiowitz, "Bioadhesive microspheres: i. A novel electrobalance-based method to study adhesive interactions between individual microspheres and intestinal mucosa," J. Control. Release 34:251-62 (1995).
Ch'ng, et al., "Bioadhesive Polymers as Platforms for Oral Controlled Drug Delivery II: Synthesis and Evaluation of Some Swelling, Water-Insoluble Bioadhesive Polymers," J. Pharm. Sci. 74: 399-405 (1988).
Duchene, et al., "Pharmaceutical and Medical Aspects of Bioadhesive Systems for Drug Administration," Drug Development &. Ind. Pharm. 14(2&3):283-31 (1988).
Gurney, et al., "Bioadhesive intraoral release systems: design, testing and analysis," Biomaterials 5:336-40 (1984).
Illum, "Bioadhesive Microspheres as Potential Nasal Drug Delivery System," Int'l J. Pharm. 39: 189-99 (1987).
Labat-Robert & Decaens, "Glycoproteines du mucus gastrique: structure, fonctions et pathologie," Pathologie Biologie 24:241 (Paris 1979).
Lehr, et al., "Intestinal transit of bioadhesive microspheres in an in situ loop in the rat—a comparative study with copolymers and blends based on poly(acrylic acid)," J. Controlled Rel. 13:51-62 (1990).
Lehr, et al., "In vitro evaluation of mucoadhesive properties of chitosan and some other natural polymers," International J. Pharmaceutics 78: 43-48 (1992).
Leon-Bay, et al., "Microsphere formation and drug delivery in a series of derivatized amino acids," Winter conference of Medicinal Chemistry (Steamboat Springs, Colarodo 1995).
Mathiowitz, et al., "Morphology of polyanhydride microsphere delivery systems," Scanning Microscopy 4(2):329-340 (1990).
Mikos, et al., "Interaction of Polymer Microspheres with Mucin Gels as a Means of Characterizing Polymer Retention on Mucus," J. Colloid & Interface Sci. 143(2):366-73 (1991).
Scawen, et al., "The Action of Proteolytic Enzymes on the Glycoprotein from Pig Gastric Mucus," Biochemical J. 163:363-68 (1977).
Smart, et al., "An in vitro investigation of mucosa-adhesive materials for use in controlled drug delivery," J. Pharm. & Pharmacol. 36:295-99 (1984).
Spiro, "Glycoproteins," Annual Review of Biochemistry 39:599-638 (Snell, ed. 1970).
Adams, et al., Amphiphilic block copolymers for drug delivery, J. Pharm. Sci., 92(7):1343-55 (2003).
Balenga, et al., "Protective efficiency of dendrosomes as novel nano-sized adjuvants for DNA vaccination against birch pollen allergy", J Biotech., 123(3):602-14 (2006).
Barinka, et al., "Interactions between human glutamate carboxypeptidase II and urea-based inhibitors: Structural characterization", J Med. Chem.,51:7737-43 (2008).
Barinka, et al., "Structural insight into the pharmacophore pocket of human glutamate carboxypoeptidase II", J. Med Chem., 50:3267-73 (2007).
Caliceti, et al. "Effective protein release from PEG/PLA nanoparticles produced by compressed gas anti-solvent precipitation techniques", J of Cont. Release, 94:195-205 (2004).
Chandran, et al, "Characterization of a targeted nanoparticle functionalized with a Urea-based inhibitor of prostate-specific membrane antigen (PSMA)", Cancer Biol & Therapy, 7(4):1-9 (2008).
Chen, et al., "Radiohalogenated prostate-specific membrane antigen (PSMA)-based ureas as imaging agents for prostate cancer", J Med Chem., 51(24):7933-43 (2008).
Dancey, et al., "Therapeutic Targets:MTOR an related pathways", Cancer Biol. Ther., 5(9):1065-73 (2006).

Ewesuedo and Ratain, "Systemically administered drugs", Drug Delivery Systems in Cancer, Humana Press, Chapter 1:3-14 (2004).
Farokhzad, et al., "Cancer nanotechnology: drug encapsulated nanoparticle-aptmer bioconjugates for targeted delivery to prostate cancer cells", 13th Eu. Cancer Conf., Oct. 30-Nov. 3, Paris France (2005).
Gu, et al., "Precise engineering of targeted nanoparticles by using self-assembled biointegrated block copolymers", PNAS, 105(7):2586-91 (2008).
Hamdy, et al., "Co-delivery of cancer-associated antigen and toll-like receptor 4 ligand in PLGA nanoparticles induces potent CD8+ T cell-mediated anti-tumor immunity", Vaccine, 26(39):5046-57 (2008).
Hong, et al., "Enhanced and prolonged cross-presentation following endosomal escape of exogenous antigens encapdulated in biodegradable nanoparticles", Immunol., 117(1):78-88 (2006).
Humblet, et al. "An HPLC/mass spectrometry platform for the development of multimodality contrast agents and targeted therapeutics: prostate-specific membrane antigen small derivatives", Contrast Med. Mol. Imaging, 1:196-211 (2006).
Humblet, et al. "High-affinity near-infrared fluorescent small-molecule contras agents for in vivo imaging of prostate-specific membrane antigen", Molecular Imaging, 4:448-62 (2005).
Igaku, "Intracellular trafficking of lipid antigens and their immune recognition by the CD1 system", Exp. Med., 24(7):936-40 (2006).
Jiang, et al., "Preparation of PLA and PLGA nanoparticles y binary organic solvent diffusion method", J. Cent. South Univ Technol, 10(3):202-06 (2003).
Kozikowski, et al. "Design of remarkably simple, yet potent urea-based inhibitors of glutamate carboxypeptidase II (NAALADase)", J. Med Chem, 44:298-301 (2001).
Lee, et al. "Adaptations of Nanoscale Viruses and Other Protein Cages for Medical Applications" Nanomedicine-Nanotechnology Biology and Medicine. 2(3):137-149 (2006).
Maresca, et al., "A series of halogenated heterodimeric inhibitors of prostate specific membrane antigen (PSMA) as radiolabeled probes for targeting prostate cancer", J. Med Chem., 52(2):347-57 (2009).
Martinez-Pomares, et al., "Fc chimeric protein containing the cysteine-rich domain of the murine mannose receptor binds to macrophages from splenic marginal zone and lymph node subcapsular sinus and to germinal centers", J Experimental Med., 184(5):1927-37 (1996).
Mease, et al., "N-[N-[(S)-1,3-Dicarboxypropyl]carbamoyl]-4-[18F]fluorobenzyl-L-cysteine, [18F]DCFBC: a new imaging probe for prostate cancer", Clin. Cancer Res., 14(10):3036-43 (2008).
Misra, et al., "Production of multimeric prostate-specific membrance antigen small-molecule radiotracers using a solid-phase 99mTc preloading strategy", J Nuclear Medicine, 48(8):1379-89 (2007).
Pomper, et al., "New developments in molecular imaging of prostate cancer", Topical Symposium on Advanced Molecular Imaging Techniques in the detection, diagnosis, therapy and follow-up of Cancer, Palazzo Barberini, Rome Dec. 6, 2005.
Pulkkinen, et al., "Three-step tumor of paclitaxel using biotinylated PLA-PEG nanoparticles and avidin-biolin technology: Formulation developing and in vitro anticancer activity", Eur. J Pharm. Biopharm., 70:66-74 (2008).
Raghuvanshi, et al., "Improved immune response from biodegradable polymer particles entrapping tetanus toxoid by use of different immunization protocol and adjuvants", Int J Pharm., 245(1-2):109-21 (2002).
Riley, et al., "Physicochemical evaluation of nanoparticles assembled from Poly(lactic acid)-Poly(ethylene glycol) (PLAPEG) block copolymers as drug delivery vehicles", Langmuir, 17:3168-74 (2001).
Sapra, et al., "Ligan-targeted liposomal anticancer drugs", Pergamon, Progress in Lipid Research, 42:439-462 (2003).
Surgery Frontier, "What's new in surgery frontier", 13(3):290-3 (2006).
Sweetman, "Entry for Docetaxel", Martindale:the complete drug reference, 33rd ed., p. 534 (2002).
Tobio, et al.,"Stealth PLA-PEG nanoparticlea as protein carriera for nasal administration", Pharm. Res., 15(2):270-75 (1998).

(56) References Cited

OTHER PUBLICATIONS

Walter, et al., "Hydrophillic poly (DL-lactide-co-glycolide) microspheres for the delivery of DNA to human-derived macrophages and dendritic cells", J Control Release, 76(1-2):149-68 (2001).

Yamamoto, et al., "Long-circulation Poly(ethylene glycol)-poly(D,L-lactide) block copolymermicelles with modulated surace chane", J Contl Rel., 77:27-38 (2001).

Yang, et al., "Micelles formed by self-assembling of polylactide/poly(ethylene glyocol) block copolymers in aqueous solutions", J. Colliod and Interface Sci., 314:470-77 (2007).

Akagi, et al., "Preparation and characterization of biodegradable nanoparticles based on poly0gamma-glutamic acid) with L-Phenylalanine as a protein carrier", J Control Release, 108:226-36 (2005).

Akagi, et al., "Protein direct delivery to dendritic cells using nanoparticles based on amphiphilic poly(amino acid) derivatives", Biomaterials, 28:3427-36 (2007).

Akerman, et al., "Nanocrystal targeting in vivo", PNAS, 99(20):12617-21 (2002).

Anderson, et al., "Biodegradation and biocompatibility of PLA and PLGA microspheres", Adv Drug Delivery, 28:5-24 (1997).

Bilati, et al., "Development of a nanoprecipitation method intended for the entrapment of hydrophilic drugs into nanoparticles", Eu J Pharma Sci., 24(1):67-75 (2005).

Cas Reg. No. 1069-79-0, 4 pages, Entered STN: Nov. 16, 1984.

Chen, et al., "Beta-arrestin 2 mediates endocytosis of type II TGF-beta receptor and down-regulation of its signaling", Science, 301:1394-7 (2003).

Deng, et al., Optimization of preparative conditions for poly-DL-lactide-polyetyhlene glycol microspheres with entrapped Vibrino Cholera antigens, J Control Release, 58(2):123-31 (1999).

Diwan, et al., "Biodegradable nanoparticle mediated antigen delivery to human cord blood derived dendritic cells for induction of primary T cell responses", J Drug Targeting, 11(8-10):495-507 (2003).

Drug Delivery Systems, 22(3):289 (2007).

Fahmy, et al., "Targeted for drug delivery", Nano Today, 18-26 (2005).

Farokhzad, "Nanotechnology for drug delivery: the perfect partnership", Exp Opin Drug Deliv., 5(9):927-9 (2008).

Henrickson, et al., "T cell sensing of antigen dose governs interactive behavior wit dendritic cells and sets a threshold for T cell activation", Nat Immunol., 9(3):282-91 (2008).

Journal of Pediatric Practice, 64(9):1389-94 (2001).

Life Technologies, retrieved from the internet http://www.lifetechnologies.com/us/en/home/references/protocols/nucleic-acid-purification-and-analysis/ma-protocal/agarose-gel-electrophoresis-of-ma.html, retrieved May 30, 2014.

Morein, et al., "Current status and potential application of ISCOMs in veterinary medicine", Adv Drug Deliv Rev., 56:1367-82 (2004).

Nobs, et al., "Surface modification of poly(lactic acid) nanoparticles by covalent attachment of thiol groups by means of three methods", Intl J Pharma., 250:327-37 (2003).

Ohuchi, et al., "Selection of RNA aptamers against recombinant transforming growth factor-$^2$ type III receptor displayed on cell surface", Biochimie, 88:897-904 (2006).

Olszewski, et al., "NAAG peptidase inhibition reduces locomotor activity and some stereotypes in the PCP model of schizophrenia via group II mGluR", J Neurochem., 89:876-85 (2004).

Ponchel, et al., "Mucoadhesion of colloidal particulate systems in the gastro-intestinal tract", Eu J Pharma Biopharma., 44:25-31 (1997).

Raghavan, et al., "Fc receptors and their interactions with immunoglobulins", Annu Rev Cell Dev.,12:181-220 (1996) Abstract Only.

Ravetch and Bolland, "IgG Fc Receptors", Ann Rev Immunol., 19:275-90 (2001).

Schiffelers, et al., "Cancer siRNA theraphy by tumor selective delivery with ligand-targeted sterically stabilized nanoparticle", Nucleic Acids Res., 32(19):1-10 (2004).

Scholfield, "Composition of soybean lecithin", J Am Oil Sci Soc., 58(10):889-92 (1981).

Shadidi and Sioud, "Selection of peptides for specific delivery of oligonucleotides into cancer cells", Methods Molecular Biol., 252:569-80 (2004).

Singh, et al., "Nanoparticles and microparticles as vaccine-delivery systems", Expert Rev. Vaccines, 6(5):797-808 (2007).

Suzuki, et al., "Development of effective antigen delivery carrier to dendritic cells via Fc receptor in cancer immunotherapy", Yakugaku Zasshi, 127(2):305-6 (2007).

Tamura, et al., "Regulation of Th2 responses by CpG motifs", Respiration, 121(12):1147-55 (2002).

Truong-Le, et al., "Gene transfer by DNA-Gelation nanospheres", Biochem and Biophy., 381:47-55 (1999).

Van de Winkel, et al., "Human Igl Fc receptor heterogeneity: molecular aspects and clinical implications", Immunology Today, 14(5):215-21 (1993).

Wakita, et a.., "Mechanisms for complete eradication of large tumor mass by liposome-CpG nanoparticle tumor vaccine", Clinical Immunology, 45(5):483-90 (2006).

Wakita, et al., "What\s new in surgery frontier", Surgery Frontier, 13(3):64-7 (2006).

Wei, et al., "Preparation of uniform-sized PELA microspheres with high encapsulation efficiency of antigens by premix membrane emulsification", J Colliod Interface Sci., 323(2):267-73 (2008).

Wu, et al.,"Selection of oligonucleotide apatamers with enhanced uptake and activation of human leukemia B cell", Human Gene, 14:849-60 (2003).

Yamamoto, et al., "Antinociceptive effects of N-acetylaspartylglutamate (NAAG) peptidase inhibitors ZJ-11, ZJ-17 and ZJ-43 in the rat formalin test and in the rat neuropathic pain model", Eur J Neurosci., 20(2):483-94 (2004).

Yoo and Park, "Folate receptor targeted biodegradable polymeric doxorubicin micelles", J Cont. Rel., 96:273-83 (2004).

Zhou, et al., "Poly-D,L-lactide-co-poly(ethylene glycol) microspheres as potential vaccine delivery systems", J Control Release, 86:195-205 (2003).

\* cited by examiner

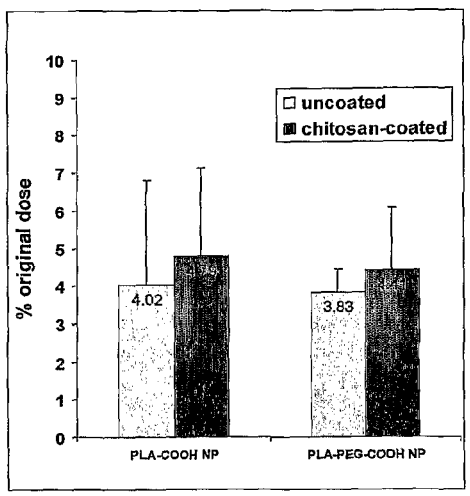
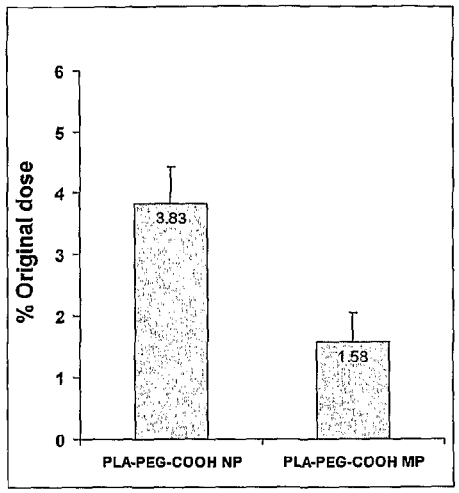
Figure 4A
Figure 4B
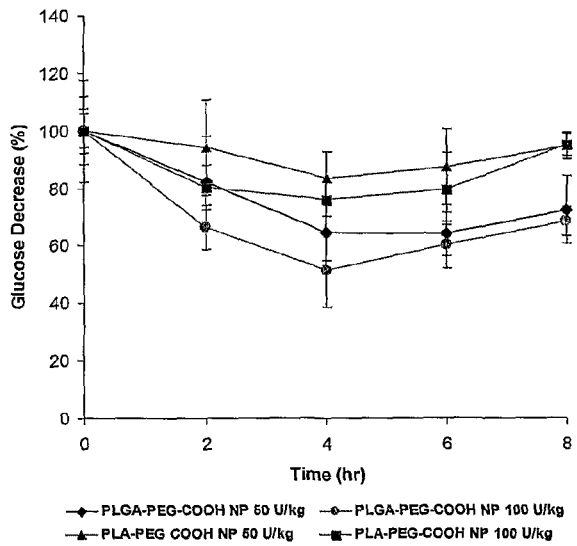
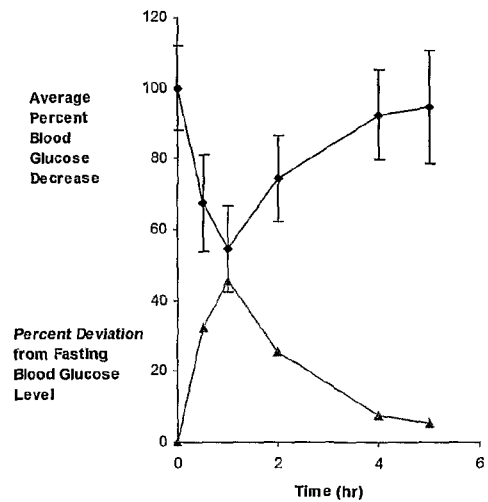
Figure 5
Figure 6
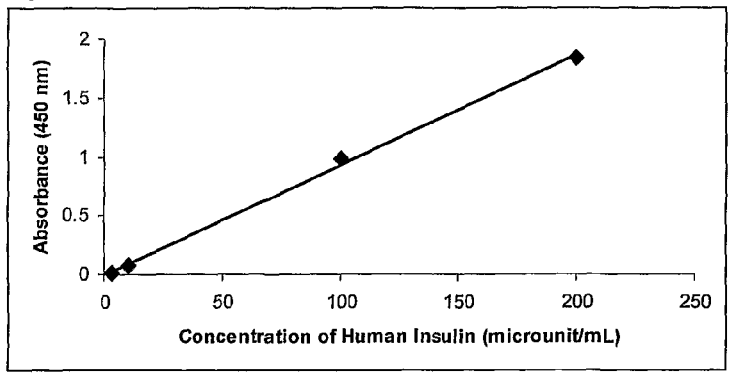
Figure 7

COATED CONTROLLED RELEASE POLYMER PARTICLES AS EFFICIENT ORAL DELIVERY VEHICLES FOR BIOPHARMACEUTICALS

This application claims the priority of U.S. Provisional Application No. 60/625,001, filed Nov. 4, 2004, the entire contents of which are incorporated herein by reference.

FIELD OF THE INVENTION

This invention pertains to drug delivery vehicles, and, more particularly, to controlled release particles coated with a mucoadhesive material.

BACKGROUND OF THE INVENTION

A vast pharmacopeia is available to treat conditions ranging from the annoyance of dry skin to life-threatening diseases. Many of these remedies can be administered orally, either through ingestion or inhalation, or through the skin as a patch or ointment. Others are susceptible to enzymatic degradation by proteases and other chemicals in the gastrointestinal (GI) tract or exhibit poor permeability through the skin or intestinal epithelial cells (enterocytes). Such drugs must be administered through less convenient methods, for example, by injection.

Unless a pharmaceutical is administered continuously, for example, using an intravenous drip, the serum levels of the drug will not be continuous. Serum levels will spike shortly after administration and then tail off in a non-linear fashion. While there may be an optimal serum concentration, a patient will only experience this optimum concentration briefly, as the concentration of the drug decreases from the initial spike. While the average concentration over time may be correct, the actual serum concentration of the drug will practically always be greater or less than optimal.

Another factor that tends to impede a patient's receipt of the proper quantity of a drug is patient compliance. Many patients are unwilling or unable to comply with a physician's instructions describing how often to take a drug. It is inconvenient and confusing to take several drugs at different times during the day and painful to inject protein drugs such as insulin.

The use of controlled-release formulations to provide a consistent dose of a drug to a patient has been an active area of research for decades and has been fueled by the many recent developments in polymer science and the need to deliver more labile pharmaceutical agents such as nucleic acids, proteins, and peptides. Controlled release polymer systems can be designed to provide a drug level in the optimum range over a longer period of time than other drug delivery methods, thus increasing both the efficacy of the drug and patient compliance.

Biodegradable particles have been developed as sustained release vehicles used in the administration of small molecule drugs as well as protein and peptide drugs and nucleic acids (Langer, *Science,* 249:1527-1533, 1990; Mulligan, *Science,* 260:926-932, 1993; Eldridge, *Mol. Immunol.,* 28:287-294, 1991; the entire teaching of each of the foregoing references is incorporated herein by reference). The drugs are typically encapsulated in a polymer matrix which is biodegradable and biocompatible. As the polymer is degraded or dissolved and/or as the drug diffuses out of the polymer, the drug is released into the body. Typically, polymers used in preparing these particles are polyesters such as poly(glycolide-co-lactide) (PLGA), polyglycolic acid, poly-β-hydroxybutyrate, and polyacrylic acid ester. These particles have the additional advantage of protecting the drug from degradation by the body.

Still, it is desirable to have controlled-release system that can be used for oral administration of substances that are not normally stable in the gastrointestinal tract or that are difficult to transport across the intestinal mucosa into the bloodstream. Oral delivery is expected to result in enhanced patient compliance, resulting in improved clinical outcomes, largely due to ease of drug administration as compared to subcutaneous or intravenous injection. An appropriate delivery system that can 1) encapsulate protein and other labile drugs, 2) protect the drugs while in transit through the gastrointestinal (GI) tract, 3) efficiently transport the drugs across the intestinal mucosa, and 4) efficiently release the drugs in the systemic circulation may result in high bioavailability of protein drugs after oral administration. Even for drugs that are stable in the GI tract, a delivery system that can transport them across the intestinal mucosa and release them directly into the bloodstream can enhance bioavailability.

SUMMARY OF THE INVENTION

In one aspect, the invention is a composition for delivering an active agent to a patient. The composition includes a polymer core encapsulating a predetermined amount of the active agent and a mucoadhesive coating disposed about the core to form a coated particle. The polymer includes covalently linked poly(alkylene glycol) chains. The mucoadhesive coating is retained on the core through one or more of covalent interactions, electrostatic interactions, affinity interactions, metal coordination, physical adsorption, host-guest interactions, and hydrogen bonding interactions. A molecular weight and cross-link density of the biodegradable polymer is selected such that the polymer core will decompose over a predetermined time interval. The mucoadhesive coating is selected to facilitate transfer of the particle through the intestinal mucosa. The fraction of the predetermined amount entering the systemic circulation during the predetermined time interval is between about 0.25% and about 25%, for example, between about 5% and about 20% or between about 10% and about 15%.

The composition may further include a targeting agent disposed under the mucoadhesive coating and, optionally, an intermediate layer disposed between the targeting agent and the mucoadhesive coating. The intermediate layer may include a first material while the mucoadhesive coating includes a second material, and the first material and the second material may have opposing electrostatic charges at pH 2, but not at pH 7.4. The intermediate layer may include a biodegradable polymer, and the targeting agent may be disposed at a surface portion of the polymer core, an interior portion of the polymer core, or both. The targeting agent may be one or more of nucleic acid aptamers, growth factors, hormones, cytokines, interleukins, antibodies, integrins, fibronectin receptors, p-glycoprotein receptors, and cell binding sequences, for example, RGD.

The core may include PEGylated poly (lactic acid). The coating may be a block co-polymer having a mucoadhesive block and a block that is adapted to participate in an interaction selected from electrostatic interactions, affinity interactions, metal coordination, physical adsorption, host-guest interactions, and hydrogen bonding interactions. The active agent may be a biomolecule, bioactive agent, small molecule, drug, protein, vaccine, or polynucleotide.

The poly(alkylene glycol) may be carboxylated and may be selected from poly(ethylene glycol) and poly(propylene glycol). The poly(alkylene glycol) may have a molecular weight between about 100 and about 7000 Daltons, for example, between about 100 and about 1000 Daltons, between about 1000 Daltons and 3500 Daltons, between 3500 Daltons and about 7000 Daltons, or more.

The coating may include one or more of chitosan, poly(lysine), poly(ethylene imine), lecithin, lectin, polycarboxylic acids, poly(acrylic acids), polysaccharides, hydrogels, monosaccharides, oligosaccharides, oligopeptides, polypeptides, and co-polymers of these.

In another aspect, the invention is a composition for administering an active agent to a patient. The composition includes a plurality of particles, each particle including a polymer core encapsulating the active agent and a mucoadhesive coating disposed about the core to form a coated particle, and a pharmaceutically acceptable carrier combined with the plurality of particles. The pharmaceutically acceptable carrier is edible or inhalable.

In another aspect, the invention is a method for administering an active agent to a patient. The method includes orally administering to the patient a composition comprising a plurality of particles. Each particle includes a polymer core encapsulating the active agent and a mucoadhesive coating disposed about the core to form a coated particle. The composition further includes a pharmaceutically acceptable edible carrier.

DEFINITIONS

"Bioavailability": The term "bioavailability", as used herein, refers to the rate at which and extent to which an active agent is absorbed or is otherwise available to a treatment site in the body. For active agents that are encapsulated in a biodegradable polymer or pharmaceutically acceptable carrier, or both, bioavailability also depends on the extent to which the active agent is released from the polymer and/or carrier into the bloodstream.

"Biomolecules": The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

"Biocompatible": The term "biocompatible", as used herein is intended to describe compounds that are not toxic to cells. Compounds are "biocompatible" if their addition to cells in vitro results in less than or equal to 20% cell death, and their administration in vivo does not induce significant inflammation or other such significant adverse effects.

"Biodegradable": As used herein, "biodegradable" polymers are polymers that degrade fully (i.e., down to monomeric species) under physiological or endosomal conditions. In preferred embodiments, the polymers and polymer biodegradation byproducts are biocompatible. Biodegradable polymers are not necessarily hydrolytically degradable and may require enzymatic action to fully degrade.

"Decomposition": As used herein, "decomposition" is the process by which a material is broken down under physiological conditions into components that may be metabolized by the body. For example, biodegradable polymers are degraded to monomeric species. Non-biodegradable polymers may be dissolved and removed from the bloodstream by the kidneys. Alternatively, the material or its components may be metabolized by the liver.

"Endosomal conditions": The phrase "endosomal conditions", as used herein, relates to the range of chemical (e.g., pH, ionic strength) and biochemical (e.g., enzyme concentrations) conditions likely to be encountered within endosomal vesicles. For most endosomal vesicles, the endosomal pH ranges from about 5.0 to 6.5.

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

"Polynucleotide", "nucleic acid", or "oligonucleotide": The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least two nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5 bromouridine, C5 fluorouridine, C5 iodouridine, C5 methylcytidine, 7 deazaadenosine, 7 deazaguanosine, 8 oxoadenosine, 8 oxoguanosine, O(6) methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N phosphoramidite linkages). Enantiomers of natural or modified nucleosides may also be used. Nucleic acids also include nucleic acid-based therapeutic agents, for example, nucleic acid ligands, siRNA, short hairpin RNA, antisense oligonucleotides, ribozymes, aptamers, and SPIEGELMERS™, oligonucleotide ligands described in Wlotzka, et al., Proc. Nat'l. Acad. Sci. USA, 2002, 99(13):8898, the entire contents of which are incorporated herein by reference.

"Polypeptide", "peptide", or "protein": According to the present invention, a "polypeptide", "peptide", or "protein" comprises a string of at least three amino acids linked together by peptide bonds. The terms "polypeptide", "peptide", and "protein", may be used interchangeably. Peptide may refer to an individual peptide or a collection of peptides. Inventive peptides preferably contain only natural amino acids, although non natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polysaccharide", "carbohydrate" or "oligosaccharide": The terms "polysaccharide", "carbohydrate", or "oligosaccharide" refer to a polymer of sugars. The terms "polysaccharide", "carbohydrate", and "oligosaccharide", may be used interchangeably. Typically, a polysaccharide comprises at least two sugars. The polymer may include natural sugars (e.g., glucose, fructose, galactose, mannose, arabinose, ribose, and xylose) and/or modified sugars (e.g., 2'-fluororibose, 2'-deoxyribose, and hexose).

"Mucoadhesive": As used herein, the term "mucoadhesive" is used to indicate that a moiety has an affinity for a component of the intestinal wall. The affinity may be specific, for example, a specific affinity for a protein or sugar found in the membrane of a cell, for example, an M cell or intestinal epithelial cell, or non-specific, for example, a tendency to non-covalently bind to the mucosa.

"Small molecule": As used herein, the term "small molecule" is used to refer to molecules, whether naturally-occurring or artificially created (e.g., via chemical synthesis) that have a relatively low molecular weight. In some embodiments, small molecules are monomeric and have a molecular weight of less than about 1500 g/mol. Preferred small molecules are biologically active in that they produce a local or systemic effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered acceptable for use in accordance with the present invention. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

"Bioactive agents": As used herein, "bioactive agents" is used to refer to compounds or entities that alter, inhibit, activate, or otherwise affect biological or chemical events. For example, bioactive agents may include, but are not limited to, anti-AIDS substances, anti-cancer substances, antibiotics, immunosuppressants, anti-viral substances, enzyme inhibitors, including but not limited to protease and reverse transcriptase inhibitors, fusion inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, and imaging agents. In a certain embodiment, the bioactive agent is a drug.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, and the United States Pharmacopeia-25/National Formulary-20, published by the United States Pharmcopeial Convention, Inc., Rockville Md., 2001, all of which are incorporated herein by reference.

As used herein, the term "pharmaceutically active agent" refers collectively to biomolecules, small molecules, and bioactive agents.

BRIEF DESCRIPTION OF THE DRAWING

The invention is described with reference to the several figures of the drawing, in which.

FIG. 4A is a graph showing the whole blood absorption of $^{125}$I-insulin delivered to balb/C mice by PEGylated and non-PEGylated PLA nanoparticles.

FIG. 4B is a graph comparing the whole blood absorption of $^{125}$I-insulin delivered to balb/C mice by PEGylated PLA nanoparticles and microparticles FIG. 5 is a graph illustrating the decrease in plasma glucose over time after administration of insulin encapsulated in PLA-PEG-COOH and PLGA-PEG-COOH nanoparticles.

FIG. 6 is a graph illustrating the reduction in plasma glucose after intravenous administration of Humulin R (0.5 U/kg)

FIG. 7 is a graph illustrating the linear relationship between absorbance and plasma insulin concentration

DETAILED DESCRIPTION OF CERTAIN PREFERRED EMBODIMENTS

A delivery device for biopharmaceuticals and other substances that are not easily transported from the gastrointestinal tract to the circulatory system or that are not stable in the gastrointestinal tract includes a polymer encapsulating an active agent and a mucoadhesive surface.

Figure 1:
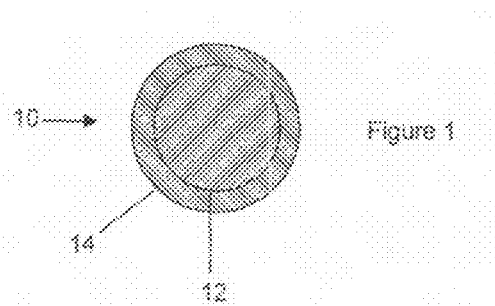
FIG. 1 is a schematic diagram of a particle according to an embodiment of the invention.

In one embodiment, the device is a plurality of microparticles or nanoparticles 10 having a core 12 in which a pharmaceutical is encapsulated by a controlled-release polymer and a mucoadhesive coating 14 disposed about the core (FIG. 1). The controlled-release polymer may be biodegradable, and the coating may be biodegradable as well. The coating is affixed to the core by covalent or non-covalent interactions. The coating may remain in place as the core material decomposes. Such particles may be ingested by a patient. The particles may be nanoparticles, having a size between about 10 and about 1000 nm, for example, between about 10 and about 100 nm, between about 100 and about 500 nm, or between about 500 and about 1000 nm. Alternatively, the particles may be microparticles having a size between about 1 and about 100 micrometers, for example, between about 1 and about 10 micrometers, between about 10 and about 50 micrometers, or between about 50 and about 100 micrometers. The particles adhere to the intestinal lining and gradually pass through the lining into the circulatory system, where they gradually release the active agent at a rate determined by the decomposition rate of the core. Alternatively, the core material may also include a mucoadhesive, obviating a coating.

Encapsulation Materials

Materials for use in encapsulating pharmaceuticals for use with the invention may be biodegradable. A variety of biodegradable polymers are well known to those skilled in the art. Exemplary synthetic polymers suitable for use with the invention include but are not limited to poly(arylates), poly(anhydrides), poly(hydroxy acids), polyesters, poly(ortho esters), polycarbonates, poly(propylene fumerates), poly(caprolactones), polyamides, polyphosphazenes, polyamino acids, polyethers, polyacetals, polylactides, polyhydroxyalkanoates, polyglycolides, polyketals, polyesteramides, poly(dioxanones), polyhydroxybutyrates, polyhydroxyvalyrates, polycarbonates, polyorthocarbonates, poly(vinyl pyrrolidone), biodegradable polycyanoacrylates, polyalkylene oxalates, polyalkylene succinates, poly(malic acid), poly(methyl vinyl ether), poly(ethylene imine), poly(acrylic acid), poly(maleic anhydride), biodegradable polyurethanes and polysaccharides. U.S. patents that describe the use of polyanhydrides for controlled delivery of substances include U.S. Pat. No. 4,857,311 to Domb and Langer, U.S. Pat. No. 4,888,176 to Langer, et al., and U.S. Pat. No. 4,789,724 to Domb and Langer.

Naturally-occurring polymers, such as polysaccharides and proteins, may also be employed. Exemplary polysaccharides include alginate, starches, dextrans, celluloses, chitin, chitosan, hyaluronic acid and its derivatives; exemplary proteins include collagen, albumin, and gelatin. Polysaccharides such as starches, dextrans, and celluloses may be unmodified or may be modified physically or chemically to affect one or more of their properties such as their characteristics in the hydrated state, their solubility, or their half-life in vivo.

In other embodiments, the polymer includes polyhydroxy acids such as polylactic acid (PLA), polyglycolic acid (PGA), their copolymers poly(lactic-co-glycolic acid) (PLGA), and mixtures of any of these. These polymers are among the synthetic polymers approved for human clinical use as surgical suture materials and in controlled release devices. They are degraded by hydrolysis to products that can be metabolized and excreted. Furthermore, copolymerization of PLA and PGA offers the advantage of a large spectrum of degradation rates from a few days to several years by simply varying the copolymer ratio of glycolic acid to lactic acid, which is more hydrophobic and less crystalline than PGA and degrades at a slower rate.

Non-biodegradable polymers may also be employed for use with the invention. Exemplary non-biodegradable, yet biocompatible polymers include polystyrene, polyesters, non-biodegradable polyurethanes, polyureas, poly(vinyl alcohol), polyamides, poly(tetrafluoroethylene), poly(ethylene vinyl acetate), polypropylene, polyacrylate, non-biodegradable polycyanoacrylates, non-biodegradable polyurethanes, polymethacrylate, poly(methyl methacrylate), polyethylene, polypyrrole, polyanilines, polythiophene, and poly(ethylene oxide).

Any of the above polymers may be functionalized with a poly(alkylene glycol), for example, poly(ethylene glycol) (PEG) or poly (propyleneglycol) (PPG), or may have a particular terminal functional group, e.g., poly(lactic acid) modified to have a terminal carboxyl group. Exemplary PEGylated polymers include but are not limited to PEGylated poly(lactic acid), PEGylated poly(lactic-co-glycolic acid), PEGylated poly(caprolactone), PEGylated poly(ortho esters), PEGylated polylysine, and PEGylated poly(ethylene imine). Poly(alkylene glycols) are known to increase the bioavailability of many pharmacologically useful compounds, partly by increasing the gastrointestinal stability of derivatized compounds. Poly(alkylene glycols) chains may be as short as about 100 Daltons or have a molecular weight of about 1000, about 3000, about 5000, about 7000 Daltons, or more. The poly(alkylene glycol) chain may also be modified to have a charged endgroup or other group selected to engage in a particular interaction with the coating material. For example, carboxylated PEG will engage in electrostatic interactions with positively charged coating materials such as chitosan.

Co-polymers, mixtures, and adducts of any of the above modified and unmodified polymers may also be employed. For example, amphiphilic block co-polymers having hydrophobic regions and anionic or otherwise hydrophilic regions may be employed. Block co-polymers having regions that engage in different types of non-covalent or covalent interactions may also be employed. For example, a block co-polymer may have one block that is optimized to interact with an active agent being encapsulated and another block optimized to interact with the bioadhesive coating (see below). Alternatively or in addition, polymers may be chemically modified to have particular functional groups. For example, polymers may be functionalized with hydroxyl, amine, carboxy, maleimide, thiol, N-hydroxysuccinimide (NHS) esters, or azide groups. These groups may be used to render the polymer hydrophilic or to achieve particular interactions with coating materials as described below.

One skilled in the art will recognize that the molecular weight and the degree of cross-linking may be adjusted to control the decomposition rate of the polymer and thus the release rate of the pharmaceutical. Methods of controlling molecular weight and cross-linking to adjust release rates are well known to those skilled in the art.

A variety of methods of making particles in which active agents are encapsulated are well known to those skilled in the art. For example, a double emulsion technique may be used to combine a polymer and active agent in particles. Alternatively, particles may be prepared by spray-drying.

Coating Materials

Positively charged biocompatible materials such as chitosan, poly(L-lysine), and poly(ethylene imines) are suitable for coating particles for use with the invention. Lectins may also be used to coat particles. Lectins may particularly target M cells in Peyer's patches in the intestine, enhancing the affinity of the particles for the intestinal wall. Lectins are produced by a wide variety of plants; one skilled in the art will recognize that not all lectins are appropriate for use in pharmaceutical compositions. A wide variety of lectins are available from Sigma-Aldrich, which also provides information on the toxicity and mutagenicity of commercially available lectins. One skilled in the art will recognize that lectins that are found in commonly eaten foods are more likely to be suitable for use with embodiments of the invention. Negatively charged materials may also be employed. Exemplary bioadhesive materials also include, without limitation, lecithin, polycarboxylic acids, poly(acrylic acids), polysaccharides, monosaccharides, oligosaccharides, oligopeptides, polypeptides, and co-polymers of two or more mucoadhesive materials. Alternatively or in addition, mucoadhesive or non-mucoadhesive polymers may be modified with mucoadhesive materials. For example, sugars may be covalently linked to polyacrylates. Polymers having regions adapted to bind the coating to the core material and regions adapted to be mucoadhesive may also be employed. For example, a block co-polymer of a polycation and a hydrogen bond donor can be used to coat a core containing a polymer that acts as a hydrogen bond receptor. Additional bioadhesive molecules that may be used with the invention include but are not limited to hydrophilic and amphiphilic polymers, hydrogels, and the polymers disclosed in U.S. Pat. Nos. 6,217,908, 6,297,337; 6,514,535; and 6,284,235 the contents of which are incorporated herein by reference. Bioadhesive molecules may be PEGylated or otherwise modified as described above.

One skilled in the art will recognize that excessive cross-linking of the coating material may hinder release of the active agent from the core of the particle. The skilled artisan will also recognize that the effect of cross-linking may be easily tested by measuring the release of an active agent or a labeled analog from particles coated with materials having different degrees of cross-linking.

In another embodiment, the particles are provided with a double coating. For example, the particles may include a targeting agent that helps direct the particles to a specific tissue once they enter the blood stream. Exemplary targeting agents include nucleic acid aptamers, growth factors, hormones, cytokines, interleukins, antibodies, integrins, fibronectin receptors, p-glycoprotein receptors, and cell binding sequences such as RGD. Nucleic acid aptamers selective for a particular target may be known from the literature or may be identified using any method known to those skilled in the art, for example, the methods disclosed in U.S. Pat. Nos. 5,270,163, 5,475,096, and 6,114,120, the contents of which are incorporated herein by reference. Aptamers for certain tissues may also be obtained commercially, for example, from Archemix Corp. These targeting agents may be attached to the surface of the particle or may be attached to the polymer itself before the particles are formed. The particles are then coated with a negatively charged material, e.g., a negatively charged polymer. Exemplary polymers include carboxymethylcellulose, polyacrylic acid, polymethacrylic acid, polystyrenesulfonate, and polymers including carboxylate, sulfonate, sulfate, phosphate, or nitrate groups. A positively charged mucoadhesive material is then coated over the negatively charged material.

After the particle crosses the intestinal wall into the bloodstream, the environmental pH increases from about 2-3 to about 7.4. Depending on the pKa of the negative coating, it may become neutrally charged, reducing its affinity for the positively charged mucoadhesive coating. As a result, the mucoadhesive coating becomes dislodged from the particle. The negatively charged coating may also be biodegradable, for example, through hydrolysis or enzymatic mechanisms. In this embodiment, whether the pKa of the negatively charged coating is such that it will become neutrally charged after entering the bloodstream, the degradation of the coating will dislodge the outer mucoadhesive coating from the particle. In any of these embodiments, the two coatings protect both the agent being delivered and the targeting agent from degradation in the digestive system while allowing the targeting agent to be exposed at the surface of the particles after they enter the bloodstream.

Pharmaceutical Compositions

The active agents to be incorporated in the controlled release polymer system of the present invention may be therapeutic, diagnostic, prophylactic or prognostic agents. Any chemical compound to be administered to an individual may be delivered using the conjugates of the invention. The active agent may be a small molecule, organometallic compound, nucleic acid, protein, peptide, metal, an isotopically labeled chemical compound, drug, vaccine, immunological agent, etc. Exemplary active agents include small molecules, biomolecules, and bioactive agents as defined herein.

In one embodiment, the agents are organic compounds with pharmaceutical activity. In another embodiment of the invention, the agent is a small molecule that is a clinically used drug. In exemplary embodiments, the drug is an antibiotic, anti-viral agent, anesthetic, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, adrenergic blocking agent, diuretic, cardiovascular active agent, vasoactive agent, non-steroidal anti-inflammatory agent, nutritional agent, etc. While many small molecule drugs are already available for oral administration, some are not sufficiently soluble to be orally administered and may benefit from the techniques described herein.

In another embodiment, the agent is a protein drug, such as an antibody, an antibody fragment, a recombinant antibody, a recombinant protein, a purified protein, a peptide, an amino acid and combinations thereof. Exemplary protein drugs include but are not limited to biologically active macromolecules such as enzyme inhibitors, colony-stimulating factors, plasminogen activators, polypeptide hormones, insulin, myelin basic protein, collagen S antigen, calcitonin, angiotensin, vasopressin, desmopressin, LH-RH (luteinizing hormone-releasing hormone), somatostatin, glucagon, somatomedin, oxytocin, gastrin, secretin, h-ANP (human atrial natriuretic polypeptide), ACTH (adrenocorticotropic hormone), MSH (melanocyte stimulating hormone), beta-endorphin, muramyl dipeptide, enkephalin, neurotensin, bombesin, VIP (vasoactive intestinal peptide), CCK-8 (cholecystokinin), PTH (parathyroid hormone), CGRP (calcitonin gene related peptide), endothelin, TRH (thyroid releasing hormone), interferons, cytokines, streptokinase, urokinase, and growth factors. Exemplary growth factors include but are not limited to activin A (ACT), retinoic acid (RA), epidermal growth factor, bone morphogenetic protein, platelet derived growth factor, hepatocyte growth factor, insulin-like growth factors (IGF) I and II, hematopoietic growth factors, peptide growth factors, erythropoietin, angiogenic factors, anti-angiogenic factors, interleukins, tumor necrosis factors, interferons, colony stimulating factors, t-PA (tissue plasminogen activator), G-CSF (granulocyte colony stimulating factor), heparin binding growth factor (HBGF), alpha or beta transforming growth factor ($\alpha$- or $\beta$-TGF), fibroblastic growth factors, epidermal growth factor (EGF), vascular endothelium growth factor (VEGF), nerve growth factor (NGF) and muscle morphogenic factor (MMP). Also suitable for use with the invention are recombinantly-produced derivatives of therapeutically useful proteins, including deletion, insertion and substitution variants, which on the whole have similar or comparable pharmacological properties.

Gene therapy technology may also benefit from the techniques of the invention. Genetic material is typically not stable in the GI tract. Polymer encapsulation can protect genetic material and "escort" it through the GI tract and into the bloodstream. In one embodiment, the active agent delivered using the techniques of the invention is a nucleic acid based drug, such as DNA, RNA, modified DNA, modified RNA, antisense oligonucleotides, expression plasmid systems, nucleotides, modified nucleotides, nucleosides, modified nucleosides, nucleic acid ligands (e.g. aptamers), intact genes, a promoter complementary region, a repressor complementary region, an enhancer complementary region, and combinations thereof. A promoter complementary region, a repressor complementary region, or an enhancer complementary region can be fully complementary or partially complementary to the DNA promoter region, repressor region, an enhancer region of a gene for which it is desirable to modulate expression. For example, it may be at least 50% complementary, at least 60% complementary, at least 70% complementary, at least 80% complementary, at least 90% complementary, or at least 95% complementary.

Genetic material is acidic and will form electrostatic bonds with cationic polymers. If it is desirable to avoid strong ionic interactions, nucleic acid based drugs can be encapsulated with anionic polymers or other hydrophilic polymers that do not have cationic groups. For example, polymers modified with short poly(cytosine) tags may be used to encapsulate genetic material. Other examples include but are not limited to polysebacic anhydride (PSA) and poly(lactic acid). These polymers may be modified to carry a more negative charge, for example, a terminal carboxylic acid group can be added to poly(lactic acid).

In another embodiment, the controlled release polymer systems may deliver a diagnostic or prognostic agent used for long term diagnosis of a patient's health. For example, kidney function is determined by delivering an agent, such as creatinine, to the bloodstream that is cleared solely by the glomerulus and then measuring the concentration of the agent in the blood or urine over time. The controlled release particles of the invention can be used to provide a steady state concentration of the clearance agent in the bloodstream for an extended period of time, and periodic assays of the concentration of the agent in the patient's urine can be used to determine the rate of clearance of the agent by the kidneys. Alternative clearance agents, for example, agents that are cleared from the body through other mechanisms, e.g, by the liver or through other metabolic processes, may also be encapsulated and delivered using the controlled release polymer systems described herein.

Prophylactic agents that can be delivered to a patient by exploiting the invention include, but are not limited to, antibiotics and nutritional supplements. For example, the techniques of the invention may be used to deliver nutrients to patients experiencing a deficiency or who are unable to produce or store such substances themselves. For example, vitamin D may be delivered to patients who are unable to synthesize it.

Vaccines and antigens are additional prophylactic agents that may be administered to a patient using the techniques of the invention. Some vaccines require extended exposure to the immune system to stimulate the desired immune response. Micro- or nanoparticles containing a vaccine or antigen may be suspended in a fluid or charged into a capsule and ingested, allowing patients to receive their vaccine orally instead of as an injection. A single administration of a dose of particles produced according to the invention may substitute for multiple injections or reduce the number of administrations. Of course, fast-decomposing particles may be fabricated to encapsulate vaccines that do not require extended exposure. Formulation of the vaccine as a capsule, pill, or ingestible liquid may also improve the shelf life of the vaccine, easing delivery of vaccines to rural or impoverished areas.

Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant, etc. Prophylactic agents include antigens of such bacterial organisms as *Streptococcus pneumoniae, Haemophilus influenzae, Staphylococcus aureus, Streptococcus pyogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

While practically any bioactive agent, small molecule, or drug may benefit from the teachings herein, certain pharmaceutical compositions will find particular utility in the inventive compositions. Proteins such as insulin that are not generally stable in the gastrointestinal system may be encapsulated using the techniques of the invention. For example, diabetics could swallow a capsule containing microparticles or nanoparticles having encapsulated insulin. The particles would adhere to the mucosa and pass through the mucosal layer into the blood stream, where they would gradually release insulin. Peptides and small molecules may be delivered in the same manner. Other biomolecules involved in metabolic disorders may also be delivered using the techniques of the invention. For example, phenylalanine hydroxylase and/or tyrosine may be administered to phenylketonurics. Nutritional and enzymatic supplements may be provided to patients with maple syrup urine disease. The techniques of the invention may be exploited to provided enzyme replacement therapy to treat a host of metabolic diseases including but not limited to Gaucher disease, Fabry disease, Niemann-Pick disease, cystic fibrosis, mucopolysaccharidosis, Tay-Sachs disease, Hurler syndrome, many forms of muscular dystrophy, including Pompe disease, and lysosomal storage disorders (see, for example, Sly, "Enzyme replacement therapy for lysosomal storage disorders: successful transition from concept to clinical practice," *Mo Med.* 2004 March-April; 101(2):100-4; Desnick, et al., "Enzyme replacement and enhancement therapies: lessons from lysosomal disorders," *Nat Rev Genet.* 2003 February; 4(2):157).

For patients who take a drug every day, the compositions of the invention can reduce the frequency with which patients have to take the drug. For example, a patient could take a pill once a week or once a month instead of daily. In one embodiment, controlled release particles produced using the invention may be used to deliver contraceptive drugs to patients. Instead of taking a pill every day, the formulations of the invention may be used to provide a weekly or monthly dose regimen. Estrogen replacement therapy may be administered in the same manner. For example, female reproductive hormones, for example, estrogen and progesterone, may be formulated as particles using the techniques of the invention.

In one embodiment of the present invention, the agent to be delivered may be a mixture of agents. For example, an antibiotic may be combined with an inhibitor of the enzyme commonly produced by bacteria to inactivate the antibiotic (e.g., penicillin and clavulanic acid). In one embodiment, different active agents may be compounded into particles, and then mixtures of different particles may be combined with a delivery vehicle in specific ratios using the techniques described below to provide different combinations of active agents to patients. For example, cyclic contraceptives work by providing a different ratio of reproductive hormones to patients over the course of three weeks, simulating the manner in which the ratio of estrogen and other hormones vary over the course of a menstrual cycle. Rather than preparing particles with different ratios of estrogen and progesterone, different ratios of particles encapsulating estrogen and progesterone may be compounded into single dosage units.

The techniques of the invention provide improved bioavailability to the compounds delivered thereby. Less of the compound will be lost in the digestive tract than if it were delivered without the protection of the encapsulating material and the PEG tag. The mucoadhesive facilitates increased transfer of the active agent across the intestinal mucosa. Using the techniques of the invention, between 0.25 and 25%, for example, between 10 and 15%, of the active agent delivered in a dosage unit can be made available to the patient through release in the bloodstream. The bioavailability of the active agent may be determined using standard pharmacokinetic techniques known to those skilled in the art. For example, the concentration of the active agent in the bloodstream or of the agent or its derivatives in urine may be measured periodically and used to calculate AUC (area under the curve).

Formation of a Coated Particle

Coatings may be immobilized on the particles using a variety of chemical interactions. For example, positively charged coatings such as chitosan will form electrostatic bonds with negatively charged PLA or PLGA. This interaction prevents the coating from being stripped off the particle as it passes into the bloodstream. Likewise, negatively charged coatings may be employed with positively charged cores.

The electrostatic interaction allows for easy fabrication of the particles and facilitates release of the active agent. Layer-by-layer deposition techniques may be used to coat the particles. For example, particles may be suspended in a solution containing the coating material, which then simply adsorbs onto the surface of the particles. The coating is not a thick or tight layer but rather allows the active agent to diffuse from the polymer core into the bloodstream. In addition, where enzymatic action is needed to decompose the core, the coating allows enzymes to diffuse from the blood into the particle. Even though the coating can remain intact as the active agent is released, it is itself susceptible to decomposition, and the particle can be fully metabolized.

In addition to electrostatic interactions, other non-covalent interactions may also be used to immobilize a coating. Exemplary non-covalent interactions include but are not limited to the following:

1) Affinity Interactions: For example, biotin may be attached to the surface of the controlled release polymer core and streptavidin may be attached to the coating material; or conversely, biotin may be attached to the coating material and the streptavidin may be attached to the surface of the controlled release polymer core. The biotin group and streptavidin are typically attached to the controlled release polymer system or to the coating via a linker, such as an alkylene linker or a polyether linker. Biotin and streptavidin bind via affinity interactions, thereby retaining the coating on the controlled release polymer core.

2) Metal Coordination: For example, a polyhistidine may be attached to the coating material, and a nitrilotriacetic acid can be attached to the surface of the controlled release polymer core. A metal, such as $Ni^{+2}$, will chelate the polyhistidine and the nitrilotriacetic acid, thereby binding the coating to the controlled release polymer core.

3) Physical Adsorption: For example, a hydrophobic tail, such as polymethacrylate or an alkyl group having at least about 10 carbons, may be attached to the coating material. The hydrophobic tail will adsorb onto the surface of a hydrophobic controlled release polymer, such as a polyorthoester, polysebacic anhydride, unmodified poly(lactic acid), or polycaprolactone, thereby binding the coating to the controlled release polymer core.

4) Host-Guest Interactions: For example, a macrocyclic host, such as cucurbituril or cyclodextrin, may be attached to the controlled release polymer or the surface of the controlled release polymer core and a guest group, such as an alkyl group, a polyethylene glycol, or a diaminoalkyl group, may be attached to the coating material; or conversely, the host group may be attached to the coating material and the guest group may be included in the controlled release polymer core. In one embodiment, the host and/or the guest molecule may be attached to the coating material or the controlled release polymer system via a linker, such as an alkylene linker or a polyether linker.

5) Hydrogen Bonding Interactions: For example, an oligonucleotide having a particular sequence may be attached to the surface of the controlled release polymer core, and an essentially complementary sequence may be attached to the coating material. The coating material will then bind to the controlled release polymer core via complementary base pairing with the oligonucleotide attached to the controlled release polymer system. Two oligonucleotides are essentially complimentary if about 80% of the nucleic acid bases on one oligonucleotide form hydrogen bonds via an oligonucleotide base pairing system, such as Watson-Crick base pairing, reverse Watson-Crick base pairing, Hoogsten base pairing, etc., with a base on the second oligonucleotide. Typically, it is desirable for an oligonucleotide sequence attached to the controlled release polymer system to form at least about 6 complementary base pairs with a complementary oligonucleotide attached to the nucleic acid ligand. For example, a poly(cytosine) tag may be attached to the controlled release polymer core and a poly(guanine) tag may be attached to the coating material. Indeed, it is not necessary to only surface treat the controlled release polymer; the entire polymer may be so modified. Some of the poly-C tags will end up on the surface of the core, and others will remain in the interior portions of the particle. In another embodiment, sugars may be used as a mucoadhesive coating. The hydroxyl groups on sugars such as glucose and galactose will hydrogen bond with polar moieties on polymers such as poly(vinyl alcohol). Sugar dimers or oligomers may be used as well.

The core and the coating may also be linked via covalent interactions. For example, PLGA may be modified with a carboxylate group and employed as a core material. Chitosan or another aminated coating material can be coupled to the core using a coupling reagent such as EDC or DCC. Alternatively, PLGA may be modified to have an activated NHS ester which can then be reacted with an amine group on the coating material. Either coating or core materials may be modified to include reactive groups such as hydroxyl, amine, carboxyl, maleimide, thiol, NHS ester, azide, or alkyne. Standard coupling reactions may then be used to couple the modified material to a second material having a complementary group (e.g., a carboxyl modified core coupled to an aminated coating material).

Administration of Inventive Compositions

Once the inventive particles have been prepared, they may be combined with pharmaceutical acceptable carriers to form a pharmaceutical composition. While the composition may be injectable or administrable as a suppository, it is preferable that the composition be orally administrable, either through ingestion or as an inhalant. To this end, the particles produced using the techniques described herein may be sufficiently small to traverse the intestinal mucosa or the alveolar wall. Enhanced uptake may be achieved for larger particles by the use of mucoadhesive coatings, as described herein. The size of the particle may be optimized for stability and increased uptake. One skilled in the art will recognize that the optimum particle size may vary depending on the nature of the drug being delivered. The studies described below may be used to determine the optimal particle size.

As used herein, the term "pharmaceutically acceptable carrier" means a non-toxic, inert solid, semi-solid or liquid filler, diluent, encapsulating material or formulation auxiliary of any type. *Remington's Pharmaceutical Sciences* Ed. by Gennaro, Mack Publishing, Easton, Pa., 1995, discloses various carriers used in formulating pharmaceutical compositions and known techniques for the preparation thereof. Some examples of materials which can serve as pharmaceutically acceptable carriers include, but are not limited to, sugars such as lactose, glucose, and sucrose; starches such as coin starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN™ 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate. Coloring agents, releasing agents, coating agents, sweetening, flavoring and perfuming agents, preservatives and/or antioxidants can also be present in the composition, according to the judgment of the formulator.

The pharmaceutical compositions of the invention can be administered to a patient by any means known in the art including oral and parenteral routes. The term "patient", as used herein, refers to humans as well as non-humans, including, for example, mammals, birds, reptiles, amphibians, and fish. Preferably, the non-humans are mammals (e.g., a rodent, a mouse, a rat, a rabbit, a monkey, a dog, a cat, a primate, or a pig). Non-edible compositions may be administered by injection (e.g., intravenous, subcutaneous or intramuscular, intraperitoneal injection), rectally, vaginally, topically (as by powders, creams, ointments, or drops), or by inhalation (as by sprays).

Powders and sprays can contain, in addition to the inventive particles of this invention, excipients such as lactose, talc, silicic acid, aluminum hydroxide, calcium silicates, and polyamide powder, or mixtures thereof. Sprays can additionally contain customary propellants such as chlorofluorohydrocarbons.

Pharmaceutical compositions for oral administration can be liquid or solid. Liquid dosage forms suitable for oral administration of inventive particles include pharmaceutically acceptable emulsions, microemulsions, solutions, suspensions, syrups, and elixirs. In addition to an encapsulated or unencapsulated particle, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants, wetting agents, emulsifying and suspending agents, sweetening, flavoring, and perfuming agents. As used herein, the term "adjuvant" refers to any compound which is a nonspecific modulator of the immune response. In certain preferred embodiments, the adjuvant stimulates the immune response. Any adjuvant may be used in accordance with the present invention. A large number of adjuvant compounds is known in the art (Allison *Dev. Biol. Stand.* 92:3-11, 1998; Unkeless et al. *Annu. Rev. Immunol.* 6:251-281, 1998; and Phillips et al. Vaccine 10:151-158, 1992).

Solid dosage forms for oral administration include capsules, tablets, pills, powders, and granules. In such solid dosage forms, the encapsulated or unencapsulated particle is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art.

It will be appreciated that the exact dosage of the inventive particle is chosen by the individual physician in view of the patient to be treated. In general, dosage and administration are adjusted to provide an effective amount of the desired active agent to the patient being treated. As used herein, the "effective amount" of a substance refers to the amount necessary to elicit the desired biological response. As will be appreciated by those of ordinary skill in the art, the effective amount of encapsulated active agent may vary depending on such factors as the desired biological endpoint, the active agent to be delivered, the target tissue, the route of administration, etc. For example, the effective amount of inventive particles containing an anti-cancer drug might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

The particles of the invention are preferably compounded with a carrier in dosage unit form for ease of administration and uniformity of dosage. The expression "dosage unit form" as used herein refers to a physically discrete unit of conjugate appropriate for the patient to be treated. It will be understood, however, that the total daily usage of the compositions of the present invention will be decided by the attending physician within the scope of sound medical judgment. For any particle composition, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of particle materials and the drugs delivered thereby can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices are preferred. The data obtained from cell culture assays and animal studies is used in formulating a range of dosage for human use.

EXAMPLES

Example 1

In Vitro and In Vivo Evaluation of Insulin Release from Nano- or Microspheres with or without Bioadhesive Polymer Coats Encapsulation of Insulin in Nano- or Microspheres Poly(D,L-lactic acid) containing carboxylic end group (PLA-COOH, inherent viscosity=0.15-0.25 corresponding to 11 k-25 k in molecular weight) was purchased from Birmingham Polymers, Inc. (Birmingham, Ala.). OH-PEG$_{3400}$-COOH was custom synthesized by Nektar Therapeutics (San Carlos, Calif., USA). $^{125}$I-labeled insulin was purchased from Amersham Bioscience (Piscataway, N.J., USA). Chitosan (minimum 85% deacetylated), poly (vinylalcohol) (PVA), and D(+)-trehalose were also obtained from Sigma.

Poly(D,L-lactic acid)-block-poly(ethylene glycol)-COOH(PLA-PEG$_{3400}$-COOH) was synthesized by ring opening polymerization with minor modifications in anhydrous toluene using stannous octoate as catalyst. D,L-Lactide (1.6 g, 11.1 mmol) and COOH-PEG$_{3400}$-OH (290 mg, 0.085 mmol) in anhydrous toluene (10 mL) containing anhydrous Na$_2$SO$_4$ (200 mg) were heated to reflux temperature at 120° C., after which the polymerization was initiated by adding tin(II) 2-ethylhexanoate (20 mg, 0.049 mmol). After stirring for 6 h with reflux, the reaction mixture was cooled to room temperature. To this solution was added cold water (10 mL), and the resulting suspension was stirred vigorously at room temperature for 30 min to hydrolyze unreacted lactide monomers. The resulting mixture was transferred to a separation funnel containing CHCl$_3$ (50 mL) and water (30 mL). After layer separation, the organic layer was collected, dried using anhydrous MgSO$_4$, filtered, and concentrated under reduced vacuum. Hexane was then added to the concentrated solution to precipitate the polymer product. Pure PLA-PEG$_{3400}$-COOH was collected as a white solid. PLA-PEG$_{3400}$-COOH: $^1$H-NMR (400 MHz), $\delta$=5.28-5.11 (br, —OC— CH(CH$_3$)O— in PLA), 3.62 (s, —CH$_2$CH$_2$O— in PEG), 1.57-1.45 (br, —OC— CHCH$_3$O— in PLA); molecular weight (GPC): M$_n$=10500 with M$_w$/M$_n$=1.54 relative to monodisperse polystyrene standards. $^1$H NMR (400 MHz) spectra were recorded on a Bruker instrument (Avance DPX 400). Aqueous phase GPC was performed by American Polymer Standards (Mentor, Ohio) using Ultrahydrogels L and 120A columns in series (Waters Corporation, Milford, Mass.). Water (1% acetic acid, 0.3 M NaCl) was used as the eluent at a flow rate of 1.0 mL/min. Data were collected using a Knauer differential refractometer and processed using an IBM/PC GPC-PRO 3.13 software package (Viscotek Corporation, Houston, Tex.).

Drug encapsulated nanoparticles were prepared using the water-in-oil-in-water (W/O/W) solvent evaporation procedure (double emulsion method) employed elsewhere. In brief, 50 μl of the $^{125}$I-labeled Insulin solution (1 mg/mL in aqueous 2 wt % trehalose) was emulsified in a 1 mL solution of the polymer (PLA-COOH or PLA-PEG-COOH) (50 mg) in dichloromethane using a probe sonicator (10 W for 15-20 s). To this emulsion was then added 3 mL of aqueous PVA (1% w/v), and the mixture was sonicated again for 20 s (10 W) using the same probe sonicator. The resulting emulsion was poured into 50 mL of aqueous PVA (0.3% w/v) with gentle stirring, after which organic solvent was rapidly removed using rotary evaporator. Finally, the $^{125}$I-Insulin encapsulated nanoparticles were isolated by centrifugation at 10,000 rpm for 10 min, washed 2 times with water, and preserved at −15° C. as emulsion form in aqueous trehalose (2% w/v, 2 mL).

Chitosan-coated nanoparticles were prepared as follows. The $^{125}$I-Insulin encapsulated nanoparticles (1 mL, ca. 10 mg) were added dropwise to chitosan solution (10 mL, 0.2 wt % in distilled water, pH 5.5) with gentle stirring. After 10 min, the resulting suspension was then centrifuged at 10,000 rpm for 10 min. The remained nanoparticles were washed with aqueous trehalose (2% w/v, 20 mL) and finally suspended in aqueous trehalose (2% w/v, 2 mL).

Characterization of Particles

Nanoparticles encapsulating $^{125}$I-labeled were prepared by the procedure above, centrifuged, and then the radioactivity in the supernatant was measured by liquid scintillation analyzer (Packard Instrument Company, Downers Grove, Ill.). The encapsulation efficiency was calculated by the difference between the total amount of radioactivity in the initial solution and the remained amount in the supernatant.

The nanoparticles before and after chitosan coating were characterized using several standard analytical means. The size of the particles and zeta-potential (surface charge) were measured by Quasi-elastic laser light scattering (QELS) using a ZetaPALS dynamic light scattering detector (Brookhaven Instruments Corporation, 15 mW laser, incident beam=676 nm). Samples (0.1 mL, ca. 1 mg) were diluted with 3 mL of distilled water. Particle sizes were measured at 25° C. Correlation functions were collected at a scattering angle of 90°, and particle sizes were calculated using the MAS option of the company's particle sizing software (version 2.30) under the viscosity and refractive index of pure water at 25° C. Particle sizes expressed as effective diameters assuming a log-normal distribution. Three measurements were made on each sample and results are reported as mean diameters. Electrophoretic mobilities were measured at 25° C. using BIC PALS zeta potential analysis software, and zeta potentials were calculated using the Smoluchowsky model. Surface morphology and size were characterized by high-resolution scanning electron microscopy (JEOL 6320FV). All samples were coated with 75 Å Au/Pd prior to analysis. Atom composition of the nanoparticles was analyzed using a Kratos AXIS Ultra Imaging X-ray Photoelectron Spectrometer with a monochromatized Al K X-ray source and a 160 mm concentric hemispherical energy analyzer for acquisition of spectra and scanned images, lateral resolution down to 20 µm. The spot size was 300 by 700 µm.

Table 1 summarizes the size, zeta potential, and drug encapsulation efficiency of the nanoparticles. As a model protein drug, $^{125}$Iodine-labeled insulin was encapsulated by PLA-COOH and PLA-PEG-COOH polymer system with efficiency of 65% and 71%, respectively. Both polymer particles showed large negative zeta potentials, indicating the presence of the negatively charged carboxylic acid group on the particle surface. In particular, a much larger negative charge was developed on the surface of PEGylated particles compared to PLA particles. This may be attributed to the presence of the hydrophilic PEG block interposed between PLA and COOH. Upon exposure to aqueous media, COOH is sequestered at the particle surface. Chitosan coating was carried out by simply adding the negatively charged particles to chitosan solution at pH 5.5. Highly positive zeta potential values are observed after chitosan coating, suggesting successful coating of the cationic chitosan onto the negatively charged nanoparticles. As expected, there were slight increases in particle sizes after chitosan coating.

TABLE 1

Particle size, zeta potential, and drag encapsulation efficiency of PLA-COOH and PLA-PEG-COOH based nanoparticles encapsulating insulin

| Polymer particles | Mean Size (nm)$^a$ | Zeta Potential (mV)$^a$ | Encapsulation efficiency (%)$^a$ |
|---|---|---|---|
| PLA-COOH | 275 ± 16 | −35 ± 3 | 65 ± 7 |
| PLA-COOH/Chitosan | 310 ± 19 | +55 ± 7 | |
| PLA-PEG-COOH | 249 ± 12 | −50 ± 3 | 71 ± 8 |
| PLA-PEG-COOH/ Chitosan | 265 ± 22 | +59 ± 5 | |

$^a$Mean ± SD (n = 3).

The scanning electron microscopic images of the particles are shown in FIG. 1. A majority of the PLA-COOH and PLA-PEG-COOH nanoparticles are approximately 200 to 300 nm, and there was no distinct discrepancy before and after chitosan coating, in agreement with the quasi-elastic laser scattering (QELS) data.

The presence of a chitosan layer on the particle surface was further confirmed by X-ray photoelectron spectroscopy (XPS). We compared high resolution carbon (1s) intensity. PLA contains three different types of carbons, namely, —C(═O)O carbonyl, C—O ether, and C—C carbons, whereas the PEG chain contains only C—O ether carbons. Very similarly, chitosan is also composed of mostly C—O ether carbon. Therefore, it is expected that after chitosan coating, the ratio of C—O to —C(═O)O carbons should increase. As shown in Table 2, the value increased by approximately 35% for PLA particles and 20% for PEGylated particles, respectively. These data also indicate that chitosan is coated onto the particle surface.

TABLE 2

High resolution XPS C(1s) composition of nanoparticles$^a$

| | Composition (%)$^b$ | | | |
|---|---|---|---|---|
| Nanoparticles | C—C | C(═O)O | C—O | C—O/ C(═O)O |
| PLA-COOH | 31.1 ± 0.7 | 32.8 ± 0.3 | 36.1 ± 0.5 | 1.10 |
| PLA-COOH$^c$ | 30.5 ± 0.4 | 28.0 ± 0.5 | 41.5 ± 0.2 | 1.48 |
| PLA-PEG-COOH | 42.2 ± 0.8 | 26.5 ± 0.6 | 31.2 ± 0.7 | 1.18 |
| PLA-PEG-COOH$^c$ | 40.5 ± 0.4 | 24.6 ± 0.3 | 35.0 ± 0.2 | 1.42 |

$^a$55 take-off angle was taken from surface normal.
$^b$Mean ± SD.
$^c$Chitosan-coated equivalent.

Evaluation of Particles in Simulated Digestive Fluid

Simulated gastric fluid (pH 1.2, pepsin 0.32% w/v, sodium chloride 0.2% w/v) and intestinal fluid (pH 7.5, pancreatin 1% w/v, monobasic potassium phosphate 0.68% w/v) were prepared by referring to US Pharmacopoeia (23$^{rd}$ edition, 1995). Pepsin from porcine stomach mucosa and pancreatin from porcine pancreases were purchased from Sigma (St Louis, USA). Chitosan-coated and uncoated nanoparticles were incubated in each digestive solution for 4 h. Degradation of PLA was determined by measuring lactate concentration in the suspension using a lactate detection kit. Briefly, each nanoparticle (5 mg) encapsulating FITC-labeled insulin (as a model protein) was incubated at 37° C. in simulated digestive fluid (5 mL) with gentle stirring using a magnetic bar. Aliquots (33 µL) were removed at appropriate time intervals and mixed with 967 µL of lactate detection kit (0.5 mL lactate dehydrogenase, 2 vials nicotinamide adenine dinucleotide, 12 mL glycine buffer). After incubation at 37° C. for 15 min, the absorbance of the solution was measured at 340 nm.

Particle stability was determined by measuring lactate concentration in solution after neutralization using a lactate detection kit. As shown in Table 3, in gastric fluid, 3% and 2% of the PLA in PLA-COOH and PLA-PEG-COOH particles, respectively, degraded. In intestinal fluid, the degradation percentage was ca. 15% and 10%, respectively. As expected, the presence of PEG increased stability as compared to simple PLA, presumably due to the enzyme repelling properties of PEG. The chitosan coating rendered the corresponding nanoparticles more stable than the uncoated equivalents in intestinal fluid (15% versus 9% degradation for PLA-COOH and 10% versus 6% degradation for PLA-PEG-COOH nanoparticles, respectively). In addition, when the chitosan-coated PLA-PEG-COOH nanoparticles were collected and analyzed after 4 h incubation in gastric fluid, the size and zeta potential of collected nanoparticles were unchanged, suggesting the chitosan coating layer remained stable on the particle surface (data not shown). Consequently, coexistence of PEG and chitosan coating layers largely increased particle stability over PLA nanoparticles in digestive fluids.

TABLE 3

Stability of the nanoparticles in simulated gastric and intestinal fluids

| Nanoparticles | PLA converted to lactate (%)[a] | |
|---|---|---|
| | Gastric fluid (4 h) | Intestinal fluid (4 h) |
| PLA-COOH | 3 ± 0.9 | 15 ± 1.3 |
| PLA-COOH[b] | 2 ± 0.5 | 9 ± 2.2 |
| PLA-PEG-COOH | 2 ± 0.3 | 10 ± 1.5 |
| PLA-PEG-COOH[b] | 2 ± 1.1 | 6 ± 0.8 |

[a]Mean ± SD.
[b]Chitosan-coated equivalent.

In Vitro Model: Determination of Uptake Efficiency of Chitosan-Coated Controlled Release Polymer Particles Across Human Intestinal Epithelial Cells (Caco-2)

All manipulations involving live cells or sterile materials were performed in a laminar flow hood using standard sterile technique. The Caco-2 cell line was purchased from the American Type Culture Collection (Manassas, Va.) and grown at 37° C., 5% $CO_2$ in Dulbecco's modified Eagle's medium (DMEM), 90%; fetal bovine serum, 10%; penicillin, 100 units/mL; streptomycin, 100 μg/mL; apo-transferrin, 10 μg/mL. Costar transwells (12 well/plate) were obtained from Corning, Inc. (Acton, Mass.).

Figure 2A:
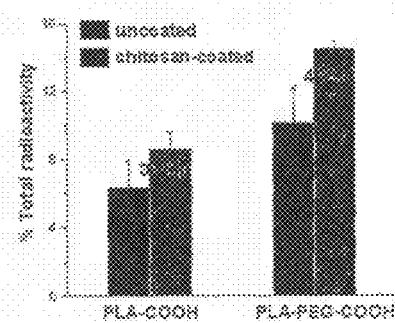
FIGS. 2A&B are graphs showing the transport yields of nanoparticles (A) and micorparticles (B) across monolayers of Caco-2 cells with and without a mucoadhesive coating.
Figure 2B:
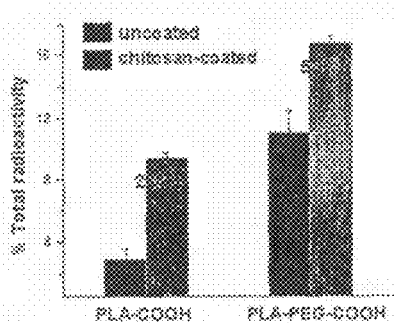

The Caco-2 cells were seeded at $1.7 \times 10^5$ cells/mL in 12 well/plate transwells (Costar, pore size of 3 μm) and grown for 12-24 days. Costar transwells had a membrane insert size of 12 mm and a pore size of 3 μm, with an apical chamber volume of 0.75 mL and a basal chamber volume of 2 mL. Cells generally reached confluence within 10 days. Transepithelial resistance measurements were made of monolayers and only cultures with greater than 250 ohms/cm$^2$ were used for experiments representing a "tight monolayer" with closed gap junctions. 100 μL of each nanoparticle from stock solution (ca. 10 mg/mL in aqueous 2% w/v trehalose) was mixed with 400 μL of cell culture medium and then, the mixture was loaded to each apical chamber. After 12 h, the radioactivity in the basal chamber was measured using a liquid scintillation analyzer to measure the transport efficiency of the particles across the Caco-2 monolayers. The transport efficiency was denoted as % total radioactivity obtained in the basal chamber. The results are summarized in FIG. 2.

First, in terms of chitosan coating effect, both non-PEGylated and PEGylated nanoparticles showed approximately 40% increased transport after chitosan coating. Enhanced transport by chitosan coating may be attributed to either increased interaction of positively charged chitosan with partially negatively charged epithelial cell layers or chitosan-facilitated paracellular transport. Although the mechanism by which chitosan can open tight junctions is not clearly demonstrated to date, it is currently accepted that it opens the junction reversibly so as to facilitate paracellular transport of macromolecules. Secondly, PEGylated polymer particles exhibited much higher (at least 60%) transport than non-PEGylated systems with and without chitosan coating. Therefore, the chitosan-coated PEGylated nanoparticle appears to have the most satisfactory transport profile in this experimental model.

In Vivo: Absorption and Biodistribution of Nanoparticles in Mice

Nanoparticles (0.2 mL) encapsulating $^{125}$I-labeled insulin were fed to mice (n=8) by a gavage method. Male BALA/c mice (10 weeks old, 22-25 g weight) were obtained from Taconic (Germantown, N.Y.) and allowed access to food and water. At 1 h after oral administration, half of the mice (n=4) were sacrificed, then samples of blood (0.2 mL) were taken by cardiac puncture. The remaining mice (n=4) were sacrificed at 6 h post oral administration and samples of blood were taken. Some organs and tissues were harvested by necropsy. The radioactivity in blood or in tissues was measured to calculate absorption yield into the body.

Figure 3A:
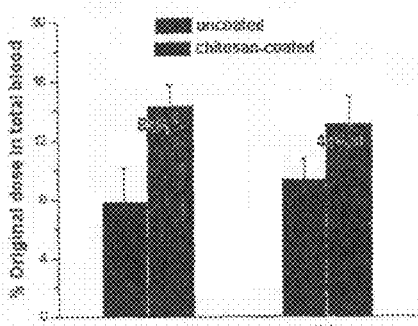
FIGS. 3A&B are graphs showing the absorption yields of nanoparticles (A) and micorparticles (B) into mice.
Figure 3B:
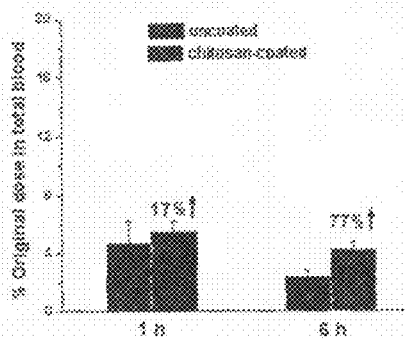

The results are summarized in FIG. 3. The absorption yield of insulin into blood was denoted as % original dose. The chitosan-coated particles exhibited approximately 80% increased insulin-absorption at 1 h and 40% increased absorption when measured at 6 h with respect to their uncoated equivalent. Much less absorption was observed for microparticles than for nanoparticles, but they both still exhibited enhanced insulin uptake after chitosan coating. Chitosan coating of nanoparticles resulted in at least 2 times higher absorption of insulin into the blood than corresponding microparticles. The absorption yield of chitosan-coated nanoparticles (14%) indicates an efficiency several times higher than reported literature values of 2-3%.

Example 2

In Vivo Absorption of $^{125}$I-Insulin and Humulin R

General

Human insulin (Humulin R, 100 U/mL and 500 U/mL, 100 unit=3.5 mg Humulin R) was purchased from www.drugstore.com and used as the stock solution. Bovine zinc insulin was purchased from Sigma. A number of different polymers used in these studies were obtained from Absorbable Polymers International (Pelham, Ala.): low molecular-weight (LMW) poly(DL-lactic acid) with acid terminal groups (LMW PLA-COOH, inherent viscosity (IV) 0.20 dL/g,), high molecular-weight (HMW) poly(DL-lactic acid) with acid terminal groups (HMW PLA-COOH, IV 0.45 dL/g), LMW 50/50 poly(DL-lactide-co-glycolide) with acid terminal groups (LMW PLGA-COOH, IV 0.18 dL/g), HMW 50/50 poly(DL-lactide-co-glycolide) with acid terminal groups (HMW PLGA-COOH, IV 0.76 dL/g). $NH_2$-$PEG_{5000}$-COOH and HO-$PEG_{5000}$-COOH were purchased from Nektar Therapeutics. $^{125}$I-labeled insulin was purchased from Amersham Bioscience (Piscataway, N.J., USA). Chemicals purchased from Sigma/Aldrich Chemical Co include Chitosan (minimum 85% deacetylated), poly (vinylalcohol) (PVA), and D(+)-trehalose tin(II) 2-ethylhexanoate, D,L-lactide, toluene (99.8%, anhydrous), and lectin from Bandeiraea Simpliciforia BS-1.

Synthesis of PLA-PEG-COOH Via Ring-Opening Polymerization

PLA-PEG-COOH was synthesized through ring opening polymerization of DL-lactide in anhydrous toluene using stannous octoate as catalyst. DL-Lactide was recrystallized with ethyl acetate prior to polymerization (using approximately 250 mL ethyl acetate to recrystallize 50 g DL-lactide). DL-lactide (15 mmol) and COOH-$PEG_{3400}$-OH (0.1 mmol) in anhydrous toluene (10 mL) were heated to 120° C. under $N_2$. Tin(II) 2-ethylhexanoate (30 mg) was added to the solution to initiate polymerization. After stirring for 6-8 h under $N_2$ at 120° C., the reaction mixture was cooled to room temperature and poured to cold methanol (60 mL). The precipitate was washed with methanol and dried under vacuum (yield 62%). $^1$H NMR (400 MHz) δ=5.20 (m, —OC—CH(CH$_3$)O—), 3.55 (s, —CH$_2$CH$_2$O—), 1.57-1.45 (br, —OC—CHCH$_3$O—).

Synthesis of PLGA-PEG-COOH (or PLA-PEG-COOH) Via Conjugation Methods

HMW DL-PLGA-COOH (0.99 g) was dissolved in anhydrous methylene chloride (5 mL). N-Hydroxysuccinimide (NHS) (23 mg) and 1-Ethyl-3-(3-dimethylaminopropyl)-carbodiimide (EDC) (42 mg) were added to the solution. After 3 h solution was poured into 25 mL cold MeOH. The precipitate was washed with 3×25 mL MeOH and dried under vacuum (yield 100%). The white solid (335 mg) obtained was re-dissolved in chloroform (3.35 mL). A chloroform solution of NH$_2$—PEG$_{5000}$-COOH (32.5 mg in 320 µL chloroform) was added dropwisely to the activated PLGA solution. Diisopropylethylamine (DIEA, 3 eq., 2.52 mg) was added the mixtures. The solution was stirred under $N_2$ overnight. The resulting PLGA-PEG-COOH was precipitated with cold MeOH and dried under vacuum (yield 95%). $^1$H NMR (400 MHz) δ=5.18 (m, —OC—CH(CH$_3$)O—), 4.79 (m, —OC—CH$_2$O—), 3.61 (s, —CH$_2$CH$_2$O—), 3.41 (s, —CH$_2$CH$_2$O—), 1.56 (br, —OC—CHCH$_3$O—).

Preparation of $^{125}$I-Insulin-Encapsulated Nanoparticles (NPs)

Drug encapsulated NPs were prepared using the water-in-oil-in-water (W/O/W) solvent evaporation procedure (double emulsion method). A 50 µl solution of the $^{125}$I-Insulin solution (1-10 µCi/mL reconstituted in pH 7.4 PBS) was emulsified in a 1 mL dichloromethane solution of 50 mg corresponding polymer (PLA-COOH, PLA-PEG-COOH) in using a probe sonicator (Sonic & Materials Inc, Danbury, Conn., USA) at 10 W for 30 s. To this emulsion was then added 3 mL of aqueous PVA (MW=30-70 kDa, 1% w/v) and the mixture was sonicated for 30 s using the same probe sonicator at 10 W. The resulting emulsion was immediately poured into 50 mL of aqueous PVA (MW=30-70 kDa, 0.3% w/v) with gentle stirring. Organic solvent was either rapidly removed using rotary evaporator or by stirring at room temperature for 2.5 h. The NPs were isolated by centrifugation at 10000 rpm for 10 min at 10° C., washed once with double-distilled water, and used for study immediately. The yield of NPs was between 20 and 30%.

Preparation of $^{125}$I-Insulin-Encapsulated Microparticles (MPs)

Drug encapsulated MPs were prepared using the water-in-oil-in-water (W/O/W) solvent evaporation procedure (double emulsion method). 50 µl of the $^{125}$I-Insulin solution (1-10 µCi/mL in pH 7.4 PBS) was emulsified in a 1 mL dichloromethane solution of 50 mg corresponding polymer (PLA-COOH, PLA-PEG-COOH) using a probe sonicator at 10 W for 30 s. The first emulsion was transferred to 50 mL of aqueous PVA (MW=30-70 kDa, 1% w/v) and homogenized at 8000 rpm for 1 minute. The resulting emulsion was immediately poured into 200 mL of aqueous PVA solution (MW=30-70 kDa, 0.3% w/v) with gentle stirring. Organic solvent was removed using rotary evaporator or by stirring at room temperature for 2.5 h. The MPs were isolated by centrifugation at 10000 rpm for 10 min at 10° C., washed once with double-distilled water, and lyophilized. The yield of MPs was between 60-80%.

Preparation of Humulin R-Encapsulated NPs and MPs

The procedures for making Humulin R-encapsulated NPs and MPs are same as that for making $^{125}$I-insulin-encapsulated NPs and MPs (see above) except that 50 µL of 500 U/mL Humulin R was used instead of $^{125}$I-insulin PBS solution.

Chitosan Coating of NP and MPs

To a suspension of NPs (or MPs) (15-30 mg in 1 mL water) was added a chitosan solution (20 mL, 0.2 wt % in distilled water, pH 5). After the suspension is allowed to stand for 10 min, the resulting suspension was centrifuged at 10000 rpm for 10 min. The NP (or MPs) were washed with 2% trehalose solution, centrifuged, and stored at −20° C. The chitosan-coated NP and MPs prepared for in vivo glucose reduction were washed with water instead of trehalose solution and used immediately.

NP Modified with Lectin

Lectin from Bandeiraea simplicifolia (Sigma) was reconstituted with DI water. LMW PLGA-COOH NP (20 mg) was activated with EDC/NHS and then reacted with lectin (0.2 mg) in the presence of excess DIEA (1 mg). The suspension was stirred for 4 h at room temperature. The resulting NPs were washed with water, centrifuged twice, and stored in 2 mL water at −15° C.

Characterization of the NPs and MPs

The size of the NPs and the zeta-potential of NPs and MPs were measured by Quasi-elastic laser light scattering (QELS) using a ZetaPALS dynamic light scattering detector (Brookhaven Instruments Corporation, 15 mW laser, incident beam=676 nm). Particle sizes were measured at room temperature at a concentration of 0.5-1 mg/mL water. Three to five measurements were made on each sample. Results are reported as mean diameters. Electrophoretic mobilities were measured at 25° C. using BIC PALS zeta potential analysis software, and zeta potentials were calculated using the Smoluchowsky model. Surface morphology and size were characterized by scanning electron microscopy.

Determination of Drug Loading

The loading of $^{125}$I-insulin in NPs and MPs was determined by analyzing the solution of known amount of NPs or MPs (2 mg NPs or MPs dissolved in 1 mL acetonitrile/water with 5 mL added Hionic-Fluoro cocktail) using a Liquid Scintillation Analyzer (Packard Instrument Company, Downers grove, IL). The loading of Humulin R was determined by measuring the actual amount of Humulin R using a BCA protein assay (Pierce Chemical Co., Rockford, Ill.). Briefly, aliquots containing known amounts of particles (5-10 mg) dissolved in 2 ml of $CH_2Cl_2$ were extracted with 2 ml buffer (1× phosphate-buffered saline (PBS) and 0.05% sodium dodecyl sulfate (SDS)). Humulin R in buffer solution was quantified using BCA assay (Pierce) in triplicate.

In-Vivo Absorption of $^{125}$I-Insulin Encapsulated PLA-Based NPs and MPs

The $^{125}$I-labelled insulin was encapsulated into NPs/MPs using carboxylate terminated poly(lactic acid) (PLA-COOH) or poly(lactic acid)-co-poly(ethylene glycol) (PLA-PEG-COOH) by the double emulsion method. The surface of the resulting NPs/MPs were negatively charged, which facilitates use of a positively charged mucoadhesive material (e.g., chitosan) coating. NPs were typically in a range of 300-400 nm, while MPs were in a range of 1-10 µm. Details for the synthesis of PLA-PEG-COOH and for the preparation and characterization NPs/MPs are given above.

$^{125}$I-Insulin encapsulated PLA or PLA-PEG NPs and MPs (Table 3) were administered to mice (n=4) orally by gavage. Each animal received 0.2 mL of the NP or MP suspension (approximately 0.2-0.5 µCi). Mice were euthanized at 6 h by $CO_2$ inhalation. Blood (200 µL) from each mouse was collected immediately in a glass scintillation vial by cardiac puncture. The blood was treated with 0.4 mL Solvable for 1 h at 55° C. Sample color turned into green. EDTA-di-sodium salt solution (0.04 mL) was added, followed by dropwise addition of 30% hydrogen peroxide (0.15 mL). The solution was allowed to stand for 15 to 30 minutes at room temperature to complete the reaction. The vial was incubated again at 55-60° C. for one hour. The color changed from green to pale yellow. After solution was cooled to room temperature for about 1 h, Hionic-Fluor (5 mL) was added to the mixture. The solution was then analyzed on a Liquid Scintillation Counter (Packard, Ill.).

TABLE 3

Nanoparticle and Microparticle Characterization

| $^{125}$I-Insulin Encapsulated Nanoparticles (NP) and Microparticles (MP) | Particle size (nm) | Zeta Potential |
| --- | --- | --- |
| PLA-COOH NP | 332 ± 2.5 | −28.42 ± 2.21 |
| PLA-PEG-COOH NP | 375 ± 6.2 | −37.49 ± 1.73 |
| PLA-COOH NP/Chitosan | 405 ± 18.6 | 53.06 ± 0.77 |
| PLA-PEG-COOH NP/Chitosan | 415 ± 13.8 | 57.33 ± 0.90 |
| PLA-PEG-COOH MP | 1-5 µm | −35.70 ± 1.07 |

NPs/MPs (Table 3) were administered to Balb/C mice (average 25 g, N=4) by oral gavage at 0.2-0.5 µCi per mouse. Mice blood (200 µL) was collected and de-colored 6 h after administration and analyzed by liquid scintillation counter (Tri-Carb, Packard). PEGylated NPs exhibited a slightly lower systemic absorption with respect to non-PEGylated NPs for both chitosan-coated (4.79% for PLA-COOH NP and 4.41% for PLA-PEG-COOH NP) and uncoated systems (4.02% for PLA-COOH NP and 3.83% for PLA-PEG-COOH NP) (FIG. 4A). The absorption of NPs coated with chitosan was enhanced with respect to equivalent NPs without chitosan. The absorption of PLA-PEG-COOH NPs was increased by 133% as compared to PLA-PEG-COOH MPs (FIG. 4B). This in-vivo absorption study showed that particle size significantly affects the absorption efficiency and smaller particles can be absorbed more efficiently.

Release of Insulin from PLA-PEG-COOH and PLGA-PEG-COOH Particles

In the previous set of experiments we measured the amount of radioactivity ($^{125}$I insulin encapsulated particles) in the plasma. However, we did not differentiate between released insulin and insulin that remained encapsulated. Since only the released insulin is therapeutically effective, it is desirable to evaluate the insulin release rate from particles prepared from various polymers. In this set of studies, we used particles generated from the PLA-PEG-COOH as before, in addition to particles generated from a poly(DL-lactide-co-glycolide)-PEG-COOH(PLGA-PEG-COOH) polymer system (the latter is expected to have a faster release kinetics). We studied the release of insulin from uncoated and chitosan-coated PLA-PEG-COOH or PLGA-PEG-COOH particles in PBS. 68% of insulin was released from uncoated PLGA-PEG-COOH NPs within 4 h, while about 42% of insulin was released from uncoated PLA-PEG-COOH NPs. The insulin release rate from particles with chitosan surface-coatings was reduced by 10-15% in both the PLA-PEG-COOH and PLGA-PEG-COOH systems.

Oral Efficacy of Humulin R Encapsulated PLA-PEG-COOH and PLGA-PEG-COOH Nanoparticles The detected radioactivity in blood is a combined effect of the released (both active and denatured), encapsulated and decomposed insulins. It is desirable to study the availibity of the free, active insulin to evaluate the effectiveness of and to further improve the polymer particles for oral insulin delivery. We determined bioavailability by measuring glucose concentrations and by quantifying released insulin in blood. Plasma glucose levels were obtained by using the Ascensia Breeze Blood Glucose Monitoring System (Bayer) following the manufacturer's protocols. Since NPs show higher in-vivo absorption than MPs (FIG. 4B), we only focused on NPs in this study.

We chose Humulin R because:
1. Humulin R consists of zinc-insulin crystals dissolved in a clear fluid. Humulin R has nothing added to change the speed or length of its action. It takes effect rapidly and has a relatively short duration of activity (about 4 hours) as compared with other insulins. Prolonged hypoglycemia obtained from a sustained release system can be attributed to the effectiveness of drug delivery vehicle.
2. Humulin R in mouse serum can be differentiated from mouse insulin using an appropriate assay, and thus can be accurately quantified.

We first chose to study the response of glucose concentration to the orally administered, Humulin R-encapsulated polymer NPs. BalB/C mice, weighing 23-25 g, were fasted for 12-16 h. The initial glucose level of each mouse was measured. Four mice were assigned to a group such that the mean values of the glucose concentrations of each group were roughly equal. Various amounts of Humulin R NPs or MPs in 200 µL water were administrated orally using gavage needles. Control mice were administered with 200 µL water only. The glucose level of each mouse was monitored at scheduled times. In some experiments and at scheduled times, in addition to measuring blood glucose concentration, we collected blood samples (50 µL) in heparinized tubes.

We found that PLA-PEG NPs generally are not as efficacious as PLGA-PEG-COOH NPs for reducing blood glucose (FIG. 5). PLGA-PEG-COOH NPs administered at 100 U/mg reduced glucose levels by 48.7±12.9%, compared to 24.0±5.93% after administration of the same dose using PLA-PEG-COOH NPs. Administration of PLGA-PEG-COOH and PLA-PEG-COOH NPs at 50 U/kg reduced serum glucose by 36.2±7.5% and 16.7±9.3%, respectively (FIG. 5). The lowest glucose levels were observed 4 hours after administration in all tested groups except for the 50 U/kg dosed PLGA-PEG-COOH NP group, in which the lowest glucose level occurred 6 hours after administration. To determine the bioavailability, we measured the glucose concentrations after tail-vein intravenous (IV) administration of Humulin R alone at 0.5 U/kg (25-50 mL total, n=4) (FIG. 6). A rapid decrease of glucose concentration was observed during the first hour, and the lowest glucose level was detected at t=1 hour with a decrease of 45.4±12.2%. The glucose concentration returned to the original level after 5 hours (FIG. 6). Based on the percent of glucose level deviation from the fasting blood glucose level for the challenged mice (see FIG. 6 for the Humulin IV administration group), we calculated the area under the curve (AUC) for the percent of the decreased blood glucose (%) vs time (hour) using the trapezoidal method for both IV and oral administration groups (Table 4). Glucose bioavailibility after the oral administration of Humulin encapsulated in PLA-PEG-COOH NPs was 0.34±0.43 and 0.58±0.28 for the 50 U/kg and 100 U/kg groups, respectively. Glucose bioavailibility after administration of PLGA-PEG-COOH NPs, however, was 1.86±0.86 and 2.53±0.62 in the 50 U/kg and 100 U/kg groups, respectively. Thus, the bioavailability of glucose delivered using of PLGA-PEG-COOH was 320%-440% higher than after delivery using PLA-PEG-COOH. Without being limited by any particular hypothesis, the increased bioavailability of insulin delivered with PLGA may be due to the accelerated drug release rate compared to PLA groups (Carino, et al., Nanosphere based oral insulin delivery. *Journal of Controlled Release* 2000, 65, 261-269).

Wash Buffer (provided in the kit). The TMB substrate (200 μL) of the kit was added to the well and incubated for 15 min at room temperature. After adding 50 μL Stop Solution, the UV absorbance was measured at 450 nm. Insulin concentration was determined based on a standard curve generated from known concentration of insulin standard.

Figure 8:
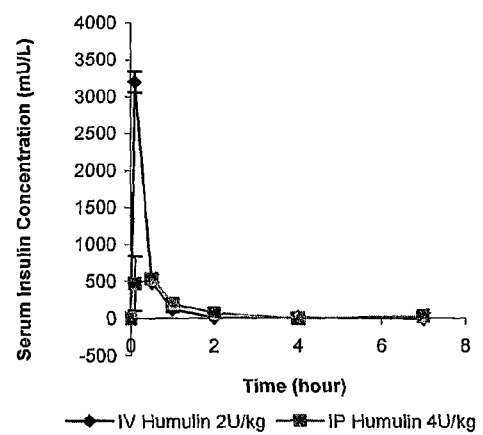
FIG. 8 is a graph illustrating the serum insulin concentration with respect to time after intravenous and intraperitoneal administration of Humulin-R

When serum was administered at 2 U/kg via tail-vein intravenous injection, the serum concentration decreased drastically from 3203.21±143.65 mU/L to 124.18±30.90 mU/L at t=1 h and to 14.17±3.08 mU/L at t=2 h (FIG. 8). Less than 0.5% of administered insulin remained in blood 2 h after administration. The AUC of insulin concentration (mU/kg) vs time (hour) was 1175.89±125.51 mU·hr/L (Table 5).

Since the encapsulation of insulin during double emulsion may denature and thus deactivate the loaded insulin, the bioactivity of some Humulin R encapsulated MPs were tested using intraperitoneal administration before testing for oral activity. Balb/c mice were fasted overnight (about 12-16 h). Humulin R and Humulin R-magnetite-PLGA-MP were injected intraperitoneally to one and three mice, respectively. Blood (1 drop, roughly 3 μL) was collected from tail vein through puncture using 26 G needle and analyzed with Ascensia Breeze Blood Glucose Monitoring System. The serum concentration of the intraperitoneally (IP) administered Humulin (4 U/kg) reached its highest level

TABLE 4

Determination of Bioavailibility of Orally Administered Humulin R Encapsulated PLA-PEG-COOH and PLGA-PEG-COOH Nanoparticles in Mice

| Gp | Route | Substrate | Dose (U/kg) | Avg Weight of Mice (g) | AUC[a] (%) | Bioavailability (f)[b] |
|---|---|---|---|---|---|---|
| 1 | IV | Humulin R | 0.5 | 29.7 | 95.79 ± 50.03 | — |
| 2 | oral | Humulin R-PLA-PEG-COOH NP | 50 | 27.5 | 76.45 ± 94.60 | 0.34 ± 0.43 |
| 3 | oral | Humulin R-PLA-PEG-COOH NP | 100 | 27 | 133.27 ± 64.58 | 0.58 ± 0.28 |
| 4 | oral | Humulin R-PLGA-PEG-COOH NP | 50 | 27.5 | 206.59 ± 94.98 | 1.86 ± 0.86 |
| 5 | oral | Humulin R-PLGA-PEG-COOH NP | 100 | 28 | 276.07 ± 68.59 | 2.53 ± 0.62 |

[a] Calculated based on trapezoidal treatment of the percent of decreased blood glucose (%) vs time (hour) for both IV and oral administration groups.
[b] $f = [AUC_{0-8\ h\ oral} \times (\text{weight of mice/dose})_{oral}]/[AUC_{0-5\ h\ IV} \times (\text{weight of mice/dose})_{IV}]$ Besides determining bioavailability based on the blood glucose concentration, we also studied bioavailability by directly measuring serum Humulin R using an ELISA insulin assay (Mercodic, ALPCO Diagnostics). This assay has very high specificity for the detection of Humulin R in mouse serum and shows no cross-reaction with mouse insulin. As shown in FIG. 7, the concentration of Humulin R measured in mouse plasma is linear over a range typically used for quantification of absorbed Humulin R via oral administration. Blood (approximately 20 μL) samples were collected into Startedt serum gel microtubes and allowed to clot for 30 minutes. The tubes were then centrifuged for 3 min at 10,000×g. Serum (5 μL) was transferred to a microwell and diluted with 20 μL calibrator 0 of the Mercodia insulin ELISA kit (ALPCO Diagnostics, Inc). Enzyme conjugate (100 μL) was added to each well. The mixture was incubated at room temperature for 1 h on a plate shaker. The reaction medium was aspirated and washed with 5×350 μL (541.85±46.92 mU/L) at t=30 minutes, and decreased to 36.32±6.92 mU/L at t=7 h (FIG. 8). The AUC of insulin concentration (mU/kg) vs time (hour) of the IP administered insulin was 692.29±272.70 mU·hr/L. The bioavailability of IP administered insulin was 29.46±11.60%.

Figure 9:
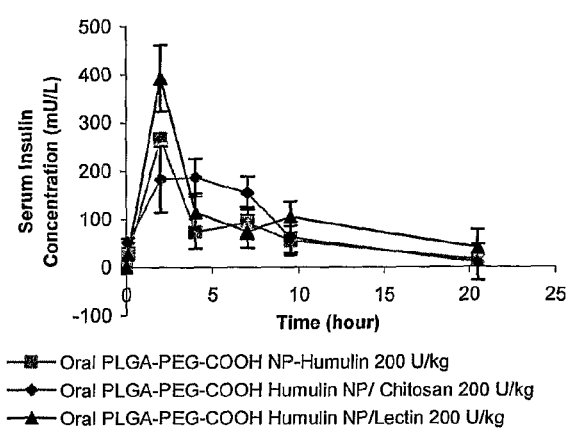
FIG. 9 is a graph illustrating the serum insulin concentration with respect to time after administration of encapsulated Humulin with various surface coatings.

After oral administration of insulin-PLGA-PEG-COOH NP, chitosan-coated, insulin-PLGA-PEG-COOH NP, and insulin-PLGA-PEG-COOH NP-Lectin bioconjugates, the highest insulin concentrations were 267.08±10.07 mU/kg (t=2 h), 188.04±46.75 mU/kg (t=4 h), and 391.87±68.43 mU/kg (t=2 h), respectively (FIG. 9). By t=20.5 h, serum insulin concentrations decreased to 15.21±7.97 mU/kg, 8.05±14.46 mU/kg, 39.48±37.76 mU/kg, respectively. The bioavailabilities of insulin-PLGA-PEG-COOH NP, chitosan-coated insulin-PLGA-PEG-COOH NP, and insulin-PLGA-PEG-COOH NP-Lectin bioconjugates were 1.22±0.38%, 1.49±0.53%, and 1.87±0.65%, respectively. Chitosan coating and lectin conjugation of PLGA-PEG- COOH NP enhanced the bioavailability by 22% and 53%, respectively. The bioavailability of the insulin-PLGA-PEG-COOH NP (1.22%) obtained by measuring insulin concentration was 54-107% lower than that determined by measuring glucose concentrations (compared to bioavailability of 1.86% and 2.53% in Table 4).

TABLE 5

Determination of Bioavailibility of Orally Administered Humulin R Encapsulated PLGA-PEG-COOH Nanoparticles with Various Surface Modifications

| Gp | Route | Substrate | Dose (U/kg) | $AUC^a$ (mU · hr/L) | Bioavailibility $(f)^b$ |
|---|---|---|---|---|---|
| 6 | IV | Humulin R | 2 | 1175.89 ± 125.51 | — |
| 7 | IP | Humulin R | 4 | 692.29 ± 272.70 | 29.43 ± 11.60 |
| 8 | oral | Humulin R-PLGA-PEG-COOH NP | 200 | 1435.63 ± 445.84 | 1.22 ± 0.38 |
| 9 | oral | Humulin R-PLGA-PEG-COOH NP/Chitosan | 200 | 1754.87 ± 629.15 | 1.49 ± 0.54 |
| 10 | oral | Humulin R-PLGA-PEG-COOH NP-Lectin Conjugate | 200 | 2194.26 ± 759.69 | 1.87 ± 0.65 |

$^a$Calculated based on trapezoidal treatment of the serum Humulin R concentration (mU/L) vs time (hour) for both IV, IP and oral administration groups.
$^b f_{oral} = (AUC_{0-20.5\ h\ oral}/dose_{oral})/(AUC_{0-7\ h\ IV}/dose_{IV})$. $f_{IP} = (AUC_{0-7\ h\ IP}/dose_{IP})/(AUC_{0-7\ h\ IV}/dose_{IV})$. Mice were grouped to make average body weight to be 30 g in each group.

Humulin R Release Study

The release of Humulin from NPs and MPs was measured by incubating aliquots containing 2-5 mg of Humulin R-containing particles in 1.0 mL of 1×??? PBS at 37°. Measurements were conducted in triplicate. The supernatant was collected after centrifugation of the particle suspension at 14000 g for 5 min and analyzed with a BCA protein assay. The amount of Humulin R was calculated based on a standard curve generated with Humulin R stock solution.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A composition comprising
   (i) a plurality of nanoparticles having a diameter between about 10 nm and 1000 nm, the nanoparticles comprising
      (a) an amphiphilic block co-polymer core encapsulating an active agent,
      (b) a mucoadhesive coating comprising a material selected from the group consisting of lectins and positively charged polymers, the coating being present on the core and interacting through electrostatic interactions with the amphiphilic block co-polymer to form a coated nanoparticle, and
      (c) a targeting agent; and
   (ii) a pharmaceutically acceptable carrier.

2. The composition of claim 1, wherein the amphiphilic block co-polymer is functionalized with one or more groups selected from the group consisting of hydroxyl, amine, carboxy, maleimide, thiol, N-hydroxy-succinimide (NHS) esters, and azide groups.

3. The composition of claim 2, wherein the amphiphilic block co-polymer is functionalized with carboxy groups.

4. The composition of claim 1, wherein the targeting agent is disposed at a surface portion of the polymer core.

5. The composition of claim 1, wherein the targeting agent is disposed on the surface portion of the polymer core and within the interior of the polymer core.

6. The composition of claim 1, wherein the targeting agent is selected from the group consisting of nucleic acid aptamers, growth factors, hormones, cytokines, interleukins, antibodies, integrins, fibronectin receptors, p-glycoprotein receptors, and cell binding sequences.

7. The composition of claim 1, providing controlled release of the active agent.

8. The composition of claim 1, wherein the mucoadhesive coating is dislodged from the particle core at pH of about 7.4.

9. The composition of claim 1, wherein the amphiphilic block co-polymer comprises a poly(alkylene glycol) block.

10. The composition of claim 9, wherein the poly(alkylene glycol) is poly(ethylene glycol) or poly(propylene glycol).

11. The composition of claim 1, wherein the amphiphilic block co-polymer core comprises PEGylated poly(lactic acid).

12. The composition of claim 9, wherein the poly(alkylene glycol) is carboxylated.

13. The composition of claim 9, wherein the poly(alkylene glycol) has a molecular weight between about 100 and about 7000 Daltons.

14. The composition of claim 13, wherein the poly(alkylene glycol) has a molecular weight between about 100 and about 1000 Daltons.

15. The composition of claim 13, wherein the poly(alkylene glycol) has a molecular weight between about 1000 and about 3500 Daltons.

16. The composition of claim 13, wherein the poly(alkylene glycol) has a molecular weight between about 3500 and 7000 Daltons.

17. The composition of claim 1, wherein the amphiphilic block co-polymer comprises a biodegradable polymer block.

18. The composition of claim 17, wherein the biodegradable polymer block is selected from the group consisting of poly(arylates), poly(anhydrides), poly(hydroxy acids), polyesters, poly(ortho esters), polycarbonates, poly(propylene fumerates), poly(caprolactones), polyamides, polyphosphazenes, polyamino acids, polyethers, polyacetals, polylactides, polyhydroxyalkanoates, polyglycolides, polyketals, polyesteramides, poly(dioxanones), polyhydroxybutyrates, polyhydroxyvalyrates, polycarbonates, polyorthocarbonates, poly(vinyl pyrrolidone), biodegradable polycyanoacrylates, polyalkylene oxalates, polyalkylene succinates, poly(malic acid), poly(methyl vinyl ether), poly(ethylene imine), poly(acrylic acid), poly(maleic anhydride), biodegradable polyurethanes, polysaccharides, and mixtures of the above.

19. The composition of claim 1, wherein the amphiphilic block co-polymer comprises a non-biodegradable polymer block selected from the group consisting of polystyrene, polyesters, non-biodegradable polyurethanes, polyureas, poly(vinyl alcohol), polyamides, poly(tetrafluoroethylene), poly(ethylene vinyl acetate), polypropylene, polyacrylate, non-biodegradable polycyanoacrylates, polymethacrylate, poly(methyl methacrylate), polyethylene, polypyrrole, polyanilines, polythiophene, poly(ethylene oxide), co-polymers of the above, and mixtures of the above.

20. The composition of claim 1, wherein the material positively charged polymers are selected from the group consisting of chitosan, poly(lysine), poly(ethylene imine), and combinations thereof.

21. The composition of claim 20, wherein the coating comprises chitosan, lectin, or both.

22. The composition of claim 1, wherein the coating is a block co-polymer having a mucoadhesive block and a block that is adapted to participate in an interaction selected from the group consisting of electrostatic interactions, affinity interactions, metal coordination, physical adsorption, host-guest interactions, and hydrogen bonding interactions.

23. The composition of claim 1, wherein the active agent is selected from the group consisting of a drug, vaccine, and polynucleotide.

24. The composition of claim 23, wherein the active agent is a vaccine.

25. The composition of claim 1, wherein the active agent is a protein.

26. The composition of claim 25, wherein the active agent is insulin.

27. A method for administering an active agent to an individual, comprising:
orally or nasally administering to the patient a composition comprising:
(i) a plurality of nanoparticles having a size between about 10 nm and 1000 nm, the nanoparticles comprising
(a) an amphiphilic block co-polymer core encapsulating active agent;
(b) a mucoadhesive coating comprising a material selected from the group consisting of lectins and positively charged polymers, the coating present on the amphiphilic block co-polymer core and interacting through electrostatic interactions with the amphiphilic polymer to form a coated nanoparticle, and
(c) a targeting agent; and
(ii) a pharmaceutically acceptable carrier.

28. The method of claim 27, wherein the amphiphilic block co-polymer is functionalized with one or more groups selected from hydroxyl, amine, carboxy, maleimide, thiol, N-hydroxy-succinimide (NHS) esters, and azide groups.

29. The method of claim 27, wherein the amphiphilic block co-polymer is functionalized with carboxy groups.

30. The method of claim 27, wherein the targeting agent is disposed at a surface portion of the polymer core.

31. The method of claim 27, wherein the targeting agent is disposed at a surface portion of the polymer core and within the interior portion of the polymer core.

32. The method of claim 27, wherein the targeting agent is selected from the group consisting of nucleic acid aptamers, growth factors, hormones, cytokines, interleukins, antibodies, integrins, fibronectin receptors, p-glycoprotein receptors, and cell binding sequences.

33. The method of claim 27, wherein the amphiphilic block co-polymer comprises a poly(alkylene glycol) block.

34. The method of claim 33, wherein the poly(alkylene glycol) is poly(ethylene glycol) or poly(propylene glycol).

35. The method of claim 33, wherein the core comprises PEGylated poly(lactic acid).

36. The method of claim 33, wherein the poly(alkylene glycol) is carboxylated.

37. The method of claim 33, wherein the poly(alkylene glycol) has a molecular weight between about 100 and about 7000 Daltons.

38. The method of claim 33, wherein the poly(alkylene glycol) has a molecular weight between about 100 and about 1000 Daltons.

39. The method of claim 33, wherein the poly(alkylene glycol) has a molecular weight between about 1000 and about 3500 Daltons.

40. The method of claim 33, wherein the poly(alkylene glycol) has a molecular weight between about 3500 and 7000 Daltons.

41. The method of claim 27, wherein the mucoadhesive coating is retained on the core though through electrostatic interactions.

42. The method of claim 27, wherein the core comprises PEGylated poly(lactic acid).

43. The method of claim 27, wherein the polymer is a biodegradable polymer.

44. The method of claim 43, wherein the biodegradable polymer is selected from the group consisting of poly (arylates), poly(anhydrides), poly(hydroxy acids), polyesters, poly(ortho esters), polycarbonates, poly(propylene fumerates), poly(caprolactones), polyamides, polyphosphazenes, polyamino acids, polyethers, polyacetals, polylactides, polyhydroxyalkanoates, polyglycolides, polyketals, polyesteramides, poly(dioxanones), polyhydroxybutyrates, polyhydroxyvalyrates, polycarbonates, polyorthocarbonates, poly(vinyl pyrrolidone), biodegradable polycyanoacrylates, polyalkylene oxalates, polyalkylene succinates, poly (malic acid), poly(methyl vinyl ether), poly(ethylene imine), poly(acrylic acid), poly(maleic anhydride), biodegradable polyurethanes, polysaccharides, co-polymers of the above, and mixtures of the above.

45. The method of claim 27 comprising a non-biodegradable polymer selected from the group consisting of polystyrene, polyesters, non-biodegradable polyurethanes, polyureas, poly(vinyl alcohol), polyamides, poly (tetrafluoroethylene), poly(ethylene vinyl acetate), polypropylene, polyacrylate, non-biodegradable polycyanoacrylates, polymethacrylate, poly(methyl methacrylate), polyethylene, polypyrrole, polyanilines, polythiophene, poly(ethylene oxide), co-polymers of the above, and mixtures of the above.

46. The method of claim 27, wherein the coating comprises lectin, chitosan, or both.

47. The method of claim 27, wherein the coating is a block co-polymer having a mucoadhesive block and a block that is adapted to participate in an interaction selected from the group consisting of electrostatic interactions, affinity interactions, metal coordination, physical adsorption, host-guest interactions, and hydrogen bonding interactions.

48. The method of claim 27, wherein the active agent is selected from the group consisting of a drug, vaccine, and polynucleotide.

49. The method of claim 48, wherein the active agent is a vaccine.

50. The method of claim 27, wherein the active agent is a protein.

51. The method of claim 48, herein the active agent is insulin.

52. The composition of claim 20, wherein the coating comprises a combination or a co-polymer of two materials selected from the group consisting of chitosan, poly(lysine), poly(ethylene imine), and lectin.

* * * * *